(12) United States Patent
Milstein et al.

(10) Patent No.: US 6,413,550 B1
(45) Date of Patent: **\*Jul. 2, 2002**

(54) PROTEINOID CARRIERS AND METHODS FOR PREPARATION AND USE THEREOF

(75) Inventors: Sam J. Milstein, Larchmont; Martin L. Kantor, Mamaroneck, both of NY (US)

(73) Assignee: Emisphere Technologies, Inc., Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/197,899

(22) Filed: Nov. 23, 1998

Related U.S. Application Data

(63) Continuation of application No. 08/705,808, filed on Aug. 30, 1996, now Pat. No. 5,840,340, which is a division of application No. 08/076,803, filed on Jun. 14, 1993, now Pat. No. 5,578,323, which is a continuation-in-part of application No. 07/920,346, filed on Jul. 27, 1992, now Pat. No. 5,443,841, which is a continuation-in-part of application No. 07/898,909, filed on Jun. 15, 1992, now abandoned.

(51) Int. Cl.[7] .................... A61K 9/16; A61K 47/42
(52) U.S. Cl. .................. 424/499; 514/773; 514/952
(58) Field of Search ................ 424/499, 491, 424/451; 514/952, 773

(56) References Cited

U.S. PATENT DOCUMENTS

| | | | |
|---|---|---|---|
| 2,671,451 A | 3/1954 | Bolger | 128/260 |
| 2,828,206 A | 3/1958 | Rosenberg | 99/2 |
| 2,862,918 A | 12/1958 | Meyer et al. | 260/123.5 |
| 2,868,740 A | 1/1959 | Luce | 260/8 |
| RE24,899 E | 11/1960 | Green | |
| 2,971,916 A | 2/1961 | Schleicher et al. | 252/62.5 |
| 3,016,308 A | 1/1962 | Macaulay | 177/37 |
| 3,052,655 A | 9/1962 | Fox et al. | 260/78 |
| 3,057,344 A | 10/1962 | Abella et al. | 128/2 |
| 3,076,790 A | 2/1963 | Fox et al. | 260/78 |
| 3,170,802 A | 2/1965 | Fukushima | 99/145 |
| 3,190,837 A | 6/1965 | Brynko et al. | 252/316 |
| 3,474,777 A | 10/1969 | Figge et al. | 128/2 |
| 3,491,093 A | 1/1970 | Pachter et al. | 260/247.5 |
| 3,565,559 A | 2/1971 | Sato | 424/37 |
| 3,567,650 A | 3/1971 | Bakan | 252/316 |

(List continued on next page.)

FOREIGN PATENT DOCUMENTS

| | | | |
|---|---|---|---|
| CA | 1077842 | 8/1976 | A61K/9/50 |
| DE | 2 424 169 | 12/1974 | A61K/9/00 |

(List continued on next page.)

OTHER PUBLICATIONS

Airaudo, C. B. et al. (1987) *Journal of Food Science*, vol. 52(6), pp. 1750–1752.

(List continued on next page.)

*Primary Examiner*—Edward J. Webman
(74) *Attorney, Agent, or Firm*—Darby & Darby

(57) ABSTRACT

Improved proteinoid carriers and methods for their preparation and use as oral delivery systems for pharmaceutical agents are described. The proteinoid carriers are soluble within selected pH ranges within the gastrointestinal tract and display enhanced stability towards at least one of photolysis or decomposition over time. The proteinoid carriers are prepared from proteinoids having between 2 and 20 amino acids and having a molecular weight of between about 250 and 2400 daltons.

21 Claims, 23 Drawing Sheets

U.S. PATENT DOCUMENTS

| | | | |
|---|---|---|---|
| 3,574,832 A | 4/1971 | Engel et al. ................. 424/183 |
| 3,576,758 A | 4/1971 | Emrick ....................... 252/316 |
| 3,687,926 A | 8/1972 | Arima et al. ............. 260/112.5 |
| 3,725,113 A | 4/1973 | Chang .......................... 117/82 |
| 3,748,277 A | 7/1973 | Wagner ...................... 252/316 |
| 3,794,561 A | 2/1974 | Matsukawa et al. ...... 195/29 R |
| 3,795,739 A | 3/1974 | Birkmayer et al. .......... 424/274 |
| 3,816,404 A | 6/1974 | Kablaoui et al. ........ 260/239.3 |
| 3,822,348 A | 7/1974 | Higashi et al. ............... 424/95 |
| 3,849,550 A | 11/1974 | Teitelbaum .................. 424/78 |
| 3,933,873 A | 1/1976 | Love et al. ............... 260/239.3 |
| 3,937,668 A | 2/1976 | Zolle ........................... 252/316 |
| 3,939,253 A | 2/1976 | Bodor et al. ................ 424/309 |
| 3,956,172 A | 5/1976 | Saeki et al. ................. 252/316 |
| 3,962,416 A | 6/1976 | Katzen .......................... 424/19 |
| 3,976,773 A | 8/1976 | Curran ........................ 424/250 |
| 4,035,507 A | 7/1977 | Bodor et al. ................ 424/311 |
| 4,048,268 A | 9/1977 | Ludwig ........................ 264/15 |
| 4,061,466 A | 12/1977 | Sjoholm et al. .......... 23/230 B |
| 4,117,801 A | 10/1978 | Dannelly et al. ............. 118/20 |
| 4,147,767 A | 4/1979 | Yapel ........................... 424/22 |
| 4,183,849 A | 1/1980 | Hansen .................... 260/112.7 |
| 4,199,561 A | 4/1980 | Roth et al. .................... 424/32 |
| 4,217,370 A | 8/1980 | Rawlings et al. ............. 426/98 |
| 4,238,506 A | 12/1980 | Stach et al. ................. 424/319 |
| 4,239,635 A | 12/1980 | Rieder ......................... 252/34 |
| 4,239,754 A | 12/1980 | Sache et al. ................ 424/183 |
| 4,272,506 A | 6/1981 | Schwarzberg ................. 424/8 |
| 4,289,759 A | 9/1981 | Heavner et al. ............ 424/177 |
| 4,345,588 A | 8/1982 | Widder et al. ............... 128/1.3 |
| 4,348,384 A | 9/1982 | Horikoshi et al. .......... 424/101 |
| 4,351,337 A | 9/1982 | Sidman ...................... 128/260 |
| 4,352,883 A | 10/1982 | Lim ............................. 435/178 |
| 4,357,259 A | 11/1982 | Senyei et al. ............... 252/316 |
| 4,388,304 A | 6/1983 | Nyeki et al. ................ 424/177 |
| 4,393,192 A | 7/1983 | Curatolo et al. ............ 528/292 |
| 4,402,856 A | 9/1983 | Schnoring et al. ...... 428/402.22 |
| 4,402,968 A | 9/1983 | Martin ........................ 424/273 |
| 4,405,598 A | 9/1983 | Brown .......................... 424/45 |
| 4,442,090 A | 4/1984 | Kakeya et al. .............. 424/178 |
| 4,446,138 A | 5/1984 | Pack ....................... 424/248.57 |
| 4,450,150 A | 5/1984 | Sidman ......................... 424/1.1 |
| 4,457,907 A | 7/1984 | Porter ......................... 424/7.1 |
| 4,460,563 A | 7/1984 | Calanchi ....................... 424/35 |
| 4,462,839 A | 7/1984 | McGinley et al. ........... 106/198 |
| 4,462,991 A | 7/1984 | Higuchi et al. ............. 424/177 |
| 4,473,620 A | 9/1984 | Wu et al. ................ 428/402.24 |
| 4,483,807 A | 11/1984 | Asano .......................... 264/22 |
| 4,492,684 A | 1/1985 | Goosen et al. ................ 424/19 |
| 4,518,433 A | 5/1985 | McGinley et al. ........... 106/180 |
| 4,590,265 A | 5/1986 | Bogan et al. ................. 536/63 |
| 4,608,278 A | 8/1986 | Frank ..................... 427/213.35 |
| 4,613,500 A | 9/1986 | Suzuki et al. ................. 429/85 |
| 4,647,455 A | 3/1987 | De Bold ....................... 424/95 |
| 4,666,641 A | 5/1987 | Fickat et al. ................. 264/4.3 |
| 4,671,954 A | 6/1987 | Goldberg .................... 424/450 |
| 4,673,566 A | 6/1987 | Goosen et al. ................ 424/19 |
| 4,683,092 A | 7/1987 | Tsang ......................... 264/4.3 |
| 4,690,786 A | 9/1987 | Ninomiya et al. ........... 264/4.6 |
| 4,692,284 A | 9/1987 | Braden ....................... 264/4.3 |
| 4,692,433 A | 9/1987 | Hostetler et al. ............. 514/12 |
| 4,703,042 A | 10/1987 | Bodor .......................... 514/56 |
| 4,708,952 A | 11/1987 | Salatinjants ................ 514/158 |
| 4,745,161 A | 5/1988 | Saudek et al. .............. 525/420 |
| 4,753,804 A | 6/1988 | Iaccheri et al. ............. 424/491 |
| 4,757,007 A | 7/1988 | Satoh .......................... 435/69 |
| 4,757,024 A | 7/1988 | Roper ......................... 436/507 |
| 4,757,066 A | 7/1988 | Shiokari et al. ............. 514/210 |
| 4,766,012 A | 8/1988 | Valenti .................. 427/213.36 |
| 4,774,320 A | 9/1988 | Tagliabue et al. ........... 530/328 |
| 4,789,734 A | 12/1988 | Pierschbacher ............. 530/395 |
| 4,835,312 A | 5/1989 | Itoh et al. ................... 564/205 |
| 4,837,381 A | 6/1989 | Steber et al. ............... 424/502 |
| 4,844,904 A | 7/1989 | Hamaguchi et al. ......... 424/450 |
| 4,873,087 A | 10/1989 | Morishita et al. ........... 424/433 |
| 4,878,942 A | 11/1989 | Motegi et al. ................ 71/109 |
| 4,886,663 A | 12/1989 | Houghten ..................... 424/88 |
| 4,895,725 A | 1/1990 | Kantor et al. ............... 424/455 |
| 4,897,444 A | 1/1990 | Brynes et al. .............. 525/54.1 |
| 4,900,730 A | 2/1990 | Miyauchi ...................... 514/12 |
| 4,908,233 A | 3/1990 | Takizawa et al. ...... 427/213.35 |
| 4,919,939 A | 4/1990 | Baker ......................... 424/493 |
| 4,925,673 A | * 5/1990 | Steiner et al. |
| 4,927,928 A | 5/1990 | Shroot et al. ............... 544/154 |
| 4,963,364 A | 10/1990 | Fox et al. .................... 424/455 |
| 4,976,968 A | 12/1990 | Steiner ........................ 424/491 |
| 4,983,402 A | 1/1991 | Steiner ....................... 424/491 |
| 4,996,292 A | 2/1991 | Fox et al. .................... 528/328 |
| 5,019,400 A | 5/1991 | Gombotz et al. ........... 424/497 |
| 5,023,374 A | 6/1991 | Simon ........................ 564/152 |
| 5,039,481 A | 8/1991 | Pacifici et al. ................. 422/4 |
| 5,041,291 A | 8/1991 | Bader et al. ................ 424/426 |
| 5,055,300 A | 10/1991 | Gupta ......................... 424/409 |
| 5,066,487 A | 11/1991 | Morelle et al. ............... 424/68 |
| 5,067,961 A | 11/1991 | Kelman et al. ................ 623/5 |
| 5,069,936 A | 12/1991 | Yen ........................ 427/213.33 |
| 5,077,278 A | 12/1991 | Hafner et al. ................. 514/30 |
| 5,100,669 A | 3/1992 | Hyon et al. ................. 424/426 |
| 5,100,918 A | 3/1992 | Sunshine et al. ........... 514/557 |
| 5,122,367 A | 6/1992 | Ron et al. ..................... 424/80 |
| 5,126,147 A | 6/1992 | Silvestri et al. ............. 424/497 |
| 5,137,892 A | 8/1992 | Chu et al. ................... 514/278 |
| 5,186,947 A | 2/1993 | Goettsche et al. .......... 424/638 |
| 5,204,099 A | 4/1993 | Barbier et al. .............. 424/401 |
| 5,206,384 A | 4/1993 | Shibahara et al. .......... 548/537 |
| 5,216,124 A | 6/1993 | Hansen, Jr. et al. ........ 530/317 |
| 5,244,653 A | 9/1993 | Berke et al. .................. 424/70 |
| 5,250,236 A | 10/1993 | Gasco ......................... 264/4.4 |
| 5,271,934 A | 12/1993 | Goldberg et al. ........... 424/401 |
| 5,271,961 A | 12/1993 | Mathiowitz et al. ... 427/213.31 |
| 5,278,148 A | 1/1994 | Branca et al. ................ 514/19 |
| 5,310,535 A | 5/1994 | Kruper, Jr. et al. ........ 424/1.53 |
| 5,328,992 A | 7/1994 | Peter et al. ................. 534/116 |
| 5,352,461 A | 10/1994 | Feldstein et al. ............ 424/493 |
| 5,384,133 A | 1/1995 | Boyes et al. ................ 424/501 |
| 5,389,377 A | 2/1995 | Chagnon et al. ............ 424/450 |
| 5,389,379 A | 2/1995 | Dirix et al. ................. 424/451 |
| 5,401,516 A | 3/1995 | Milstein et al. ............. 424/491 |
| 5,418,010 A | 5/1995 | Janda et al. ............ 427/213.31 |
| 5,439,686 A | 8/1995 | Desai et al. ................. 424/451 |
| 5,443,841 A | * 8/1995 | Milstein et al. |
| 5,447,728 A | 9/1995 | Milstein et al. ............. 424/490 |
| 5,451,410 A | 9/1995 | Milstein et al. ............. 424/490 |
| 5,474,997 A | 12/1995 | Gray et al. .................. 514/252 |
| 5,536,813 A | 7/1996 | Charpenel et al. .......... 530/324 |
| 5,540,939 A | 7/1996 | Milstein et al. ............. 424/491 |
| 5,541,155 A | 7/1996 | Leone-Bay et al. ............ 514/2 |
| 5,578,323 A | * 11/1996 | Milstein et al. |
| 5,601,846 A | * 2/1997 | Milstein et al. |
| 5,629,020 A | 5/1997 | Leone-Bay et al. ......... 424/489 |
| 5,643,957 A | 7/1997 | Leone-Bay et al. ......... 514/563 |
| 5,650,386 A | 7/1997 | Leone-Bay et al. ............ 514/2 |
| 5,665,700 A | 9/1997 | Cho et al. ...................... 514/2 |
| 5,667,806 A | 9/1997 | Kantor ........................ 424/484 |
| 5,693,338 A | 12/1997 | Milstein ...................... 424/451 |
| 5,705,529 A | 1/1998 | Matyus et al. .............. 514/541 |
| 5,709,861 A | 1/1998 | Santiago et al. ......... 424/184.1 |
| 5,714,167 A | 2/1998 | Milstein et al. ............. 424/490 |
| 5,750,147 A | 5/1998 | Kantor ....................... 424/491 |
| 5,766,633 A | 6/1998 | Milstein et al. ............. 424/489 |
| 5,773,647 A | 6/1998 | Leone-Bay et al. ......... 562/444 |
| 5,776,888 A | 7/1998 | Leone-Bay et al. ............ 514/2 |
| 5,792,451 A | 8/1998 | Sarubbi et al. ............ 424/85.4 |
| 5,804,688 A | 9/1998 | Leone-Bay et al. ......... 562/444 |
| 5,811,127 A | 9/1998 | Milstein et al. ............. 424/490 |
| 5,820,881 A | 10/1998 | Milstein ...................... 424/489 |
| 5,824,345 A | 10/1998 | Milstein ...................... 424/489 |
| 5,840,340 A | 11/1998 | Milstein et al. ............. 424/499 |
| 5,863,944 A | 1/1999 | Leone-Bay et al. ......... 514/559 |
| 5,866,536 A | 2/1999 | Leone-Bay et al. ............ 514/2 |

| | | | | |
|---|---|---|---|---|
| 5,876,710 A | 3/1999 | Leone-Bay et al. ........ 424/85.1 |
| 5,879,681 A | 3/1999 | Leone-Bay et al. ........ 424/85.1 |

FOREIGN PATENT DOCUMENTS

| | | | |
|---|---|---|---|
| DE | 2 343 037 | 3/1975 | |
| DE | 3 202 255 | 10/1982 | .......... C08L/89/00 |
| DE | 3 612 102.9 | 10/1986 | .......... C07K/15/00 |
| EP | 0 000 667 A1 | 2/1979 | ............ A61K/9/50 |
| EP | 0 036 145 A1 | 9/1981 | .......... A61K/31/62 |
| EP | 0 068 314 | 1/1983 | .......... A61K/31/16 |
| EP | 0 105 804 | 4/1984 | ............ C12N/15/00 |
| EP | 0 130 162 A2 | 1/1985 | ............ B01J/13/02 |
| EP | 0 170 540 A1 | 2/1986 | ............ A61K/9/52 |
| EP | 226223 A2 | 6/1987 | ........ C07C/103/46 |
| EP | 0 342 054 A2 | 11/1989 | ............ A61K/7/06 |
| EP | 0 342 056 A2 | 11/1989 | ............ A61K/7/06 |
| EP | 0 365 183 | 4/1990 | ........ C07C/311/21 |
| EP | 0 366 277 | 5/1990 | .......... A61K/9/107 |
| EP | 0 418 642 | 3/1991 | .......... A61K/37/30 |
| EP | 0 448 057 | 9/1991 | ............ C12P/21/08 |
| EP | 0 452 161 | 10/1991 | ............ A61K/7/48 |
| EP | 0 459 795 | 12/1991 | ............ A61K/37/02 |
| EP | 0 467 389 | 1/1992 | ............ A61K/9/52 |
| EP | 0 490 549 A1 | 6/1992 | ............ A61K/47/12 |
| EP | 0 517 211 A1 | 9/1992 | ............ A61K/47/12 |
| EP | 0 616 799 A1 | 9/1994 | ............ A61K/7/00 |
| FR | 1 351 358 | 3/1964 | |
| FR | 1 468 601 | 2/1967 | |
| FR | 2 133 926 | 12/1972 | .......... A61K/27/00 |
| FR | 2 326 934 | 5/1977 | .......... A61K/47/00 |
| FR | 2 565 102 | 12/1985 | ............ A61K/9/52 |
| GB | 929401 | 6/1963 | |
| GB | 1 075 952 | 8/1967 | |
| GB | 1 236 885 | 6/1971 | |
| GB | 1 567 763 | 5/1980 | ............ A61K/9/22 |
| GB | 2 095 994 | 10/1982 | ............ A61K/9/00 |
| IL | 71258/2 | 12/1987 | |
| JP | 48-24246 | 3/1973 | |
| JP | 56-68612 | 6/1981 | .......... A61K/31/19 |
| JP | 58-35111 | 3/1983 | ............ A61K/9/66 |
| JP | 06-107682 | 4/1994 | |
| NL | 280825 | 12/1964 | |
| NL | 280826 | 12/1964 | |
| NO | B-146698 | 11/1982 | .......... A61K/37/26 |
| WO | WO 85/00105 | 1/1985 | ............ A61K/9/52 |
| WO | WO 85/00110 | 1/1985 | .......... A61K/47/00 |
| WO | WO 85/00809 | 2/1985 | ........ C07D/233/64 |
| WO | WO 87/04076 | 7/1987 | .......... A61K/45/02 |
| WO | WO 88/01213 | 2/1988 | ............ B23B/5/16 |
| WO | WO 92/19263 | 12/1992 | ............ A61K/39/00 |
| WO | WO 93/18754 | 9/1993 | ............ A61K/9/16 |
| WO | WO 93/25583 | 12/1993 | ........... C07K/15/00 |
| WO | WO 94/11015 | 5/1994 | ............ A61K/37/00 |
| WO | WO 94/14420 | 7/1994 | ............ A61K/9/16 |
| WO | WO 94/18950 | 9/1994 | ............ A61K/9/127 |
| WO | WO 94/18997 | 9/1994 | ............ A61K/37/00 |
| WO | WO 94/21234 | 9/1994 | ............ A61K/7/00 |
| WO | WO 94/23702 | 10/1994 | ............ A61K/9/16 |
| WO | WO 94/23767 | 10/1994 | ............ A61L/9/16 |
| WO | WO 94/24291 | 10/1994 | ........ A61K/39/015 |
| WO | WO 94/28878 | 12/1994 | ............ A61K/9/14 |
| WO | WO 95/11690 | 5/1995 | .......... A61K/37/00 |
| WO | WO 85/02772 | 7/1995 | .......... A61K/49/00 |
| WO | WO 95/28838 | 11/1995 | .......... A01N/37/46 |
| WO | WO 95/28920 | 11/1995 | .......... A61K/31/19 |
| WO | WO 96/12473 | 5/1996 | ............ A61K/9/16 |
| WO | WO 96/12474 | 5/1996 | ............ A61K/9/16 |
| WO | WO 96/12475 | 5/1996 | ............ A61K/9/16 |
| WO | WO 96/21464 | 7/1996 | .......... A61K/39/00 |
| WO | WO 96/30036 | 10/1996 | .......... A61K/38/00 |
| WO | WO 96/33699 | 10/1996 | ............ A61K/9/16 |
| WO | WO 96/39835 | 12/1996 | ............ A01N/43/50 |
| WO | WO 96/40070 | 12/1996 | ............ A61K/9/14 |
| WO | WO 96/40076 | 12/1996 | ............ A61K/9/16 |
| WO | WO 97/10197 | 3/1997 | ............ C07C/51/10 |
| WO | WO 97/31938 | 9/1997 | ............ C07K/5/00 |
| WO | WO 97/36480 | 10/1997 | .......... A01N/37/12 |
| WO | WO 97/47270 | 12/1997 | |
| WO | WO 97/47288 | 12/1997 | ............ A61K/9/48 |
| WO | WO 98/49135 | 5/1998 | ........ C07C/231/00 |
| WO | WO 98/34632 | 8/1998 | .......... A61K/38/00 |
| WO | WO 98/50341 | 11/1998 | ........ C07C/229/00 |
| WO | WO 99/16427 | 4/1999 | ............ A61K/9/16 |

OTHER PUBLICATIONS

Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits...", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S. W. et al. (1976) *BioSystems*, vol. 8, pp. 40–44.
Fox, S. W. et al., *Molecular Evolution and the Origin of Life*, Maxel Decker, New York (1977).
Fox, S. W. et al. (1968) *Biochim. Biophys. Acta*, vol. 160, pp. 246–249.
Fox, S. W. (1976) *Origins of Life*, vol. 7, pp. 49–68.
Fox, S. W. (1980) *Naturwissenschaften*, vol. 67, pp. 378–383.
Fox, S. W. et al. (1960) *Archives of Biochemistry and Biophysics*, vol. 86, pp. 281–285.
Fox, S. W. et al. (1974) *Origins of Life*, vol. 5, pp. 227–237.
Fox, S. W. (1984) *Origins of Life*, vol. 14, pp. 485–488.
Gol'dovskii, A. M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) BioSystems, vol. 11, pp. 47–53.
Harada et al., (1960) *Archives of Biochemistry and Biophysics*, vol. 86, pp. 274–280.
Hare (1970) *Etude Cenetique De La Polycondensation Thermique D'X–Amino Acides*, vol. 45, pp. 330–339.
Heinrich, M. R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L. L. et al. (1976) *BioSystems*, vol. 8, pp. 89–101.
Hsu, L. L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J. R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345–346.
Krampitz, G. et al. (1966) *Naturwissenschaften*, pp. 7 and 8.
Lacey, Jr., J. C. et al. (1979) *BioSystems*, vol. 11, pp. 9–17.
Lacey, Jr., J. C. et al. (1979) *BioSystems,* vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.

McAlhaney, W. W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V. J. A. (1984) *Origins of Life*, vol. 14, pp. 513–522.
Olafsson, P. G. et al. (1971) *Polymer Letters*, vol. 9, pp. 521–528.
Phillips, R. D. et al. (1974) *Int. J. Peptide Protein Res.*, vol. 6, pp. 309–319.
Przybylski, A. T. et al. (1982) *Die Naturwissenschaften*, vol.. 69, pp. 561–563.
Przybylski, A. T. et al. (1984) *Applied Biochemistry and Biotechnology*, vol. 10, pp. 301–307.
Przybylski, A. T. (1985) *BioSystems*, vol. 17, pp. 281–288.
Rohlfing, D. L. (1975) *Origins of Life*, vol. 6, pp. 203–209.
Rohlfing, D. L. (1970) *Science*, vol. 169, pp. 998–1000.
Rohlfing, D. L. (1967) *Archives of Biochemistry and Biophysics*, vol. 118, pp. 468–474.
Rohlfing, D. L. et al. *Catalytic Activities of Thermal Polyanhydro–α–Amino Acids*, pp. 373–418, 1969.
Rohlfing, D. L. et al. (1976) *BioSystems*, vol. 8, pp. 139–145.
Ryan, J. W. et al. (1973) *BioSystems*, vol. 5, pp. 115–118.
Saunders, M. A. et al. (1974) *BioSystems*, vol. 6, pp. 81–92.
Snyder, W. D. et al. (1975) *BioSystems*, vol. 7, pp. 222–229.
Sokol, P. E. (1974) *Journal of the American Oil Chemists' Society*, vol. 52, pp. 101–102.
Tschager et al. (1988) *Milchwirtschaftiliche Berichte*, vol. 95, pp. 79–83.
Vaughan, G. et al. (1987) *BioSystems*, vol. 20, pp. 219–223.
Vol'kenshtein, M. V. (1989) *Molekulyarnaya Biologiya*, vol. 23(1), pp. 23–37.
Waehneldt, T. V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), vol. 105(1), Abstract No. 12027p.
(1985) *Chemical Abstracts*, vol. No. 102(6), Abstract No. 50870d.
*Chemical Abstract*, vol. 80(9) Abst. No. 52392a.
Bergeron, Raymond J., et al., (1994) "Macromolecular Self–Assembly of Diketopiperazine Tetrapeptides", *Journal of the American Chemical Society*, vol. 116, pp. 8479–8484.
Bergeron, Raymond J., et al. (1993) "A Comparative Study of the Iron–Clearing Properties of Desferrithiocin Analogues With Desferrioxamine B in a *Cebus Monkey* Model", *Blood*, vol. 81, No. 8, pp. 2166–2173.
Bergeron, Raymond J., et al. (1992) "A Comparison of the Iron Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.
Bergeron, Raymond et al. "A Comparative Evaluation of Iron Clearance Models", *Annals New York Academy of Sciences*, pp. 278–393, Mar. 13–15, 1990.
Andriuoli, G., et al. (1990), *Haemostasis* 20 (suppl. 1):154–158.
Caramazza, I., et al. (1991), *Thrombosis Research* 62: 785–789.
Guarini, S., et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research*, vol. 23, No. 4, part 2, p. 540A, col. 1, abstract No. 2209.
Bernstein (1985), *Chest* 87(1):68S–73S.
Damge et al. (1988), *Diabetes* 37:246–251.
*Chemical Abstracts*:83 184360k, (1975).
Amino, Y., et al., *Chem. Pharm. Bull.* 36(11):4426–4434 (1988).
Baughman, R. A. et al., *Proc. of the 6th Inter'l. Symp. on Recent Advs. in Drug Delivery Systems*, Ctr. for Controlled Chem. Delivery, University of Utah, Feb. 22–25, 1993, Salt Lake City, UT, pp. 179–180 "Method for Assessing The Stability of Proteinoid Microspheres".
Haas, S. et al. "Assessment Of Stability Of Proteinoid Microspheres", *Proceed. Intern. Symp. Control. Rel. Bioact. Mater.*, 20 (1993), Controlled Release Society, Inc.
X. Ma, et al., *Proceed. Intern. Symp. Control. rel. Bioact. Mater.*, 20 (1993), Controlled Release Society, Inc. "In Vitro Mechanistic Investigation of the Proteinoid Microsphere Oral Delivery System".
Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.
Presented at "*IBC Rational Drug Design Conference*", San Diego, Cailf.—Dec. 1994.
Leone–Bay et al., Presented at "Winter Conference on Medicinal and Bioorganic Chemistry" Steamboat Springs, Colorado—Feb. 1995 "Microsphere Formation and Drug Delivery in a Series of Derivatized Amino Acids".
Santiago et al., *Pharm. Res.* 11: 1994, p.S–298 "Oral Delivery of Heparin Microspheres made with Modified Amino Acids".
Leone–Bay et al., *Pharm. Res.* 11: 1994, p.S–121 "Oral Delivery of Heparin using Acylated Amino Acids".
Sarubbi et al., *Pharm Res.* 11: 1994, p.S–299 "Oral Calcitonin Delivery using the PODDS Technology".
Leipold et al., *Pharm. Res.* 11: 1994, p.S–298 "Oral Delivery of Interferon in Rats and Primates".
Santiago et al., *Pharm. Res.* 11: 1994, p.S–298 "Evaluation in Rats of Vehicles for the Oral Delivery of Low Molecular Weight Heparin".
X. Ma et al., PDD 7303 *Pharmaceutical Research* 9(10):S–244, 1992 (Oct. Supplement).
Milstein et al., *Symposia Abstracts*. AAPS Annual Meeting, San Antonia, TX, Nov. 15–19, 1993.
Santiago et al. "Initial Studies In The Assessment of Proteinoid Microsphere Activity"*Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater., 19 (1992)*, Controlled Release Society, Inc., pp. 116–117.

Santiago et al. "Proteinoid Microspheres For The Oral Delivery of Heparin" *Proceed. Intern. Symp. Control. Rel. Bioact. Mater., 19 (1992)*, Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater., 19 (1992)*, Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M. S., *Eastern Analytical Symposium*, Nov. 17, 1992 "Solutions for Problems in Bioanalysis".

*AAPS 6TH Ann. Meeting and Expo.*, "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on recent Advances in Drug Delivery Systems*, Ctr. for Controlled Chem. Delivery, University of Utah, Feb. 22–25, 1993, pp. 181–182.

Robert O. Dillman, M.D.,*Annals of Internal Medicine* 1989: 111 pp. 592–600. "Monoclonal Antibodies for Treating Cancer".

Brendan D. Curti, *Critical Reviews in Oncology/Hematology*, 1993: 14 pp. 29–39 "Physical barriers to drug delivery in tumors".

V. Hird et al, *Genes and Cancer*, edited by Desmond Carney & Karol Sikora, pp. 183–189, Immunotherapy with Monoclonal Antibodies.

Michael E. Osband et al.,*Immunology Today*, vol. 11, No.6 1990, pp. 193–195, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science*, Jun. 21, 1991, 252:1657–1662, "Monoclonal Antibodies in Diagnosis and Therapy".

*Chemical Abstracts*, 76(14):72994u, (1971).

*Chemical Abstracts*, 84(7):44660d, (1975).

*Chemical Abstracts*, 86(16):107529g, (1976).

*Chemical Abstracts*, 112(15):134663h, (1989).

*Chemical Abstracts*, 114(22):214519x, (1990).

J. Györe et al., *Thermal Analysis*, vol. 2—Proceeding Fourth ICTA Budapest 1974, pp. 387–394.

*Chemical Abstracts*, 99(19) 158832b, (1982).

*Derwent Abstracts*, JP 67008622, 1(1967).

*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry*, vol. 38, No. 21, pp. 4263–4269, (1995), "N–Acylated α–Amino Acids as Novel Oral Delivery Agents for Proteins".

*The Extra Pharmacopoeia*, Thirtieth Edition, pp. 325–326, (1993).

Stephen J. Douglas et al., *Chemistry and Industry*, vol. 22:748–751, 1985.

C. A. Finch, *Chemistry and Industry*, vol. 22:752–756, 1985.

John A. Butera et al., *J. Med. Chem.*, vol. 34:3212–3228, 1990.

Madeline G. Cimini et al., *Ann. Report in Med Chem.*, vol. 27:89–98., 1992.

Bernadette Earley et al., *Brain Research*, vol. 546–282–286, 1991.

John W. Ellingboe et al., *J. Med Chem.*, vol. 35:705–716, 1992.

William C. Lumma et al., *J. Med Chem.*, vol. 30:758–763, 1987.

Joseph J. Lynch et al., *J. of Pharm. and Exp. Therap.*, vol. 269:541–554, 1994.

Kiyoshi Matsuno et al., *Brain Research*, vol. 575:315–319, 1992.

Thomas K. Morgan et al., *J. Med. Chem.*, vol. 33:1091–1097, 1990.

Hitoshi Oinuma et al., *J. Med. Chem.*, vol. 33:903–905, 1990.

Tadimeti S. Rao et al., *Molecular Pharmacology*, vol. 37:978–982, 1990.

Asaji Kondo, *Microcapsule Processing and Technology*, pp. 154–165, 1979.

G. Pastores et al., *J. Liquid Chromatography*, 18(15):3049–3059, 1995.

D. Sinha et al.,*J. Bio. Chem.*, 260(19):10714–10719. 1985.

E. Franssen et al., *J. Med. Chem.*, 35:1246–1259, 1992.

*Chemical Abstracts*, 99(23):191473h, Dec. 5, 1983.

R. Langer, *Science*, 249:1528, Sep. 28, 1990.

M. Alonso et al., *Vaccine*, 12:299, 1994.

A. Leone–Bay et al., *J. Med. Chem.*, 39:2571–2578, 1996.

R. Thompson, *Biochemistry*, 12:47–51, 1973.

S. Thompson, *J. Med. Chem.*, abstract, 86:174780, 1986.

G. Picciola, II Farmaco, 31:655–664 (1976).

Tanaka et al., Biophysical Chemistry, vol. 50 (1994) 47–61.

Degrado et al., Science, vol. 243, (1989) 622–628.

Lynee Regan et al., Science, vol. 241 (1988), 976–978.

Matouschek et al., Nature, vol. 340, (1989) 122–126.

Parker et al., Peptide Research 347, vol. 4, No. 6 (1991).

Parker et al., Peptide Research 355, vol. 4, No. 6 (1991).

Fedorov et al., J. Mol. Biol. (1992) 225, 927–931.

Ptitsyn et al., Biopolymers, vol. 22, 15–25 (1983) 15–25.

Ptitsyn et al., Protein Engineering vol. 2, No. 6, 443–447, 1989.

J. M. Lehn, Makromol. Chem., Macromol. Symp. (1993) vol. 69, 1–17.

Paolo Scrimin, Chemistry Chimicaoggi (1989).

J. M. Lehn, Angew. Chem. Int. Ed. Engl. 27 (1988) 89–112.

\* cited by examiner

FIG. 6

PURE 9BG5 { 1=2µg  
2=0.0µg  
3=0.25µg

EMPTY SPHERES { 4=sup 25µl  
5=pellet 25µl mAb SPHERES { 6=sup 25µl  
7=pellet 25µl <u>1</u> <u>2</u> <u>3</u> <u>MW</u> <u>X</u> <u>4</u> <u>5</u> <u>6</u> <u>7</u>

98

68

43

28

18

PROTEINOID CARRIERS AND METHODS FOR PREPARATION AND USE THEREOF

This is a continuation, of application Ser. No. 08/705,808 filed Aug. 30, 1996, now U.S. Pat. No. 5,840,340, which in turn is a divisional of Ser. No. 08/076,803 filed Jun. 14, 1993, now U.S. Pat. No. 5,578,323, which in turn is a continuation-in-part of Ser. No. 07/920,346 filed Jul. 27, 1992, now U.S. Pat. No. 5,443,841 which in turn is a continuation-in-part of Ser. No. 07/898,909 filed Jun. 15, 1992, now abandoned. Each of these prior applications is hereby incorporated herein by reference, in its entirety.

FIELD OF THE INVENTION

This invention relates to proteinoids and proteinoid carriers made from them. The proteinoid carriers releasably encapsulate active agents and have extended longer shelf life and/or photostability. Methods for the preparation of such proteinoid carriers are also disclosed.

BACKGROUND OF THE INVENTION

The available modes of delivery of pharmaceutical and therapeutic agents often are severely limited by chemical or physical barriers or both, which are imposed by the body. For example, oral delivery of many such agents would be the route of choice if not for the presence of chemical and physicochemical barriers such as extreme pH in the gut, exposure to powerful digestive enzymes, and impermeability of gastrointestinal membranes to the active ingredient. Among the numerous pharmacological agents which are known to be unsuitable for oral administration are biologically active peptides and proteins, such as insulin. These agents are rapidly destroyed in the gut by acid hydrolysis and/or by proteolytic enzymes.

A great deal of research has been devoted to developing effective oral drug delivery methods and systems for these vulnerable pharmacological agents. The proposed solutions have included:

(a) co-administration of adjuvants (such as resorcinols and non-ionic surfactants polyoxyethylene oleyl ether and n-hexadecyl polyethylene ether to increase the permeability of the intestinal walls; and (b) co-administration of enzymatic inhibitors, such as pancreatic trypsin inhibitor, diisopropylfluorophosphate (DFF) and trasylol to avoid enzymatic degradation.

The use of such substances, in drug delivery systems, is limited however either because of:

(a) their inherent toxicity when employed at effective amounts;

(b) their failure to protect the active ingredient or promote its absorption;

(c) their adverse interaction with the drug.

Liposomes as drug delivery systems have also been described. They provide a layer of lipid around the encapsulated pharmacological agent. The use of liposomes containing heparin is disclosed in U.S. Pat. No. 4,239,754 and several studies have been directed to the use of liposomes containing insulin; e.g., Patel et al. (1976) *FEBS Letters* Vol. 62, page 60 and Hashimoto et al. (1979) *Endocrinol. Japan*, Vol. 26, page 337. The use of liposomes, however, is still in the development stage and there are continuing problems, including:

(a) poor stability;

(b) inadequate shelf life;

(c) limited to low MW (<30,000) cargoes;

(d) difficulty in manufacturing;

(e) adverse interactions with cargoes.

More recently, synthetic amino acid polymers or proteinoids, forming microspheres, have been described for encapsulating pharmaceuticals. For example, U.S. Pat. No. 4,925,673 (the '673 patent), the disclosure which is hereby incorporated by reference in its entirety, describes such microsphere constructs as well as methods for their preparation and use. The '673 patent also describes microspheres which encapsulate pharmaceutical agents for delivery into the gastrointestinal tract or into the blood.

While the proteinoid microspheres described in the '673 patent are useful for their intended purposes, the physicochemical properties of the proteinoid microspheres, such as light sensitivity, shelf life and the selectivity of their solubility in various portions of the gastrointestinal tract, could be improved. Additionally, there is a need in the art for microspheres that can encapsulate a broader range of active agents such as polar drugs.

The method employed in the '673 patent to prepare proteinoids produces a complex mixture of high molecular weight (MW) (>1000 daltons) and low MW ($\leq 1000$ daltons) peptide-like polymers which are difficult to separate. Moreover, the method produces a small amount of the low MW proteinoids which is the microsphere-forming fraction. Hence, an improved method of preparing of the proteinoids is also desired.

Accordingly, there is a need in the art for improved proteinoid carriers as well as improved methods for their preparation.

OBJECTS OF THE INVENTION

It is an object of this invention to provide proteinoids which forms proteinoid carriers as a delivery system with enhanced stability towards at least one of photodegradation and decomposition over time.

It is another object of the invention to provide a proteinoid that forms proteinoid carriers with more selective solubility under various conditions such as pH.

It is yet another object of the invention to provide proteinoid carriers encapsulating biologically active agents which are selectively releasable within particular portions of the gastrointestinal tract.

It is a further object of the invention to provide proteinoid carriers which promote the bioavailability of pharmaceutical agents which otherwise display poor absorption in the gastrointestinal tract.

It is yet a further object of the invention to provide an improved method for producing proteinoid carriers having particular characteristics and for improving yield of the desired proteinoid carriers.

It has been found that these objects and other advantages, which will be apparent from this specification, are achieved by the invention described below.

SUMMARY OF THE INVENTION

The present invention relates to improved proteinoid carriers and methods of making and use thereof.

Proteinoids of a MW ranging between about 250 and about 2400 daltons and of defined amino acids are useful in preparing proteinoid carriers with improved stability against photodegradation and/or decomposition. The proteinoids comprise a peptide polymer selected from the group consisting of:

(i) peptide polymers made from at least one first monomer selected from the group consisting of tyrosine and phenylalanine; and from at least one second monomer selected from the group consisting of glutamic acid, pyroglutamic acid, glutamine, and aspartic acid;

(ii) peptide polymers made from at least one first monomer selected from the group consisting of tyrosine and phenylalanine; and from at least one second monomer selected from the group consisting of glutamic acid, pyroglutamic acid, glutamine, and aspartic acid; and from at least one third monomer selected from the group consisting of lysine, arginine and ornithine, the proteinoid being a microsphere- and/or microcapsule-forming proteinoid and being soluble within a selected pH range.

The proteinoid molecules of the invention contain between about 2 and about 20 amino acid residues, preferably between about 2 and about 8 amino acid residues, and has a molecular weight which ranges between about 250 and about 2400 daltons, preferably between about 250 and about 600, and most preferably between about 250 and 400 daltons.

The proteinoid carriers are useful as delivery systems to releasably encapsulate and carry a broad range of cargoes including pharmaceutical agents, dye reagents and cosmetic ingredients. In particular, the proteinoid carriers are useful as oral delivery systems of sensitive pharmaceutical agents, which normally would not be administrable via the oral route, for selective release at targeted regions of the gastrointestinal tract.

DESCRIPTION OF THE DRAWINGS

FIG. 6 is a photograph of an x-ray film of the western immunoblot analysis, as described in Example 9, of purified murine mAb 9BG5 (2 µg, lane 1; 1 mg, lane 2; and 0.25 µg, lane 3); empty proteinoid carrier supernatant after encapsulating process (no mAb) (lane 4); empty proteinoid carrier pellet (lane 5); proteinoid carrier encapsulated mAb supernatant after encapsulating process (lane 6).; and proteinoid carrier encapsulated mAb pellet. Lane MW contained standard molecular weight markers.

DETAILED DESCRIPTION OF THE INVENTION

Figure 1:
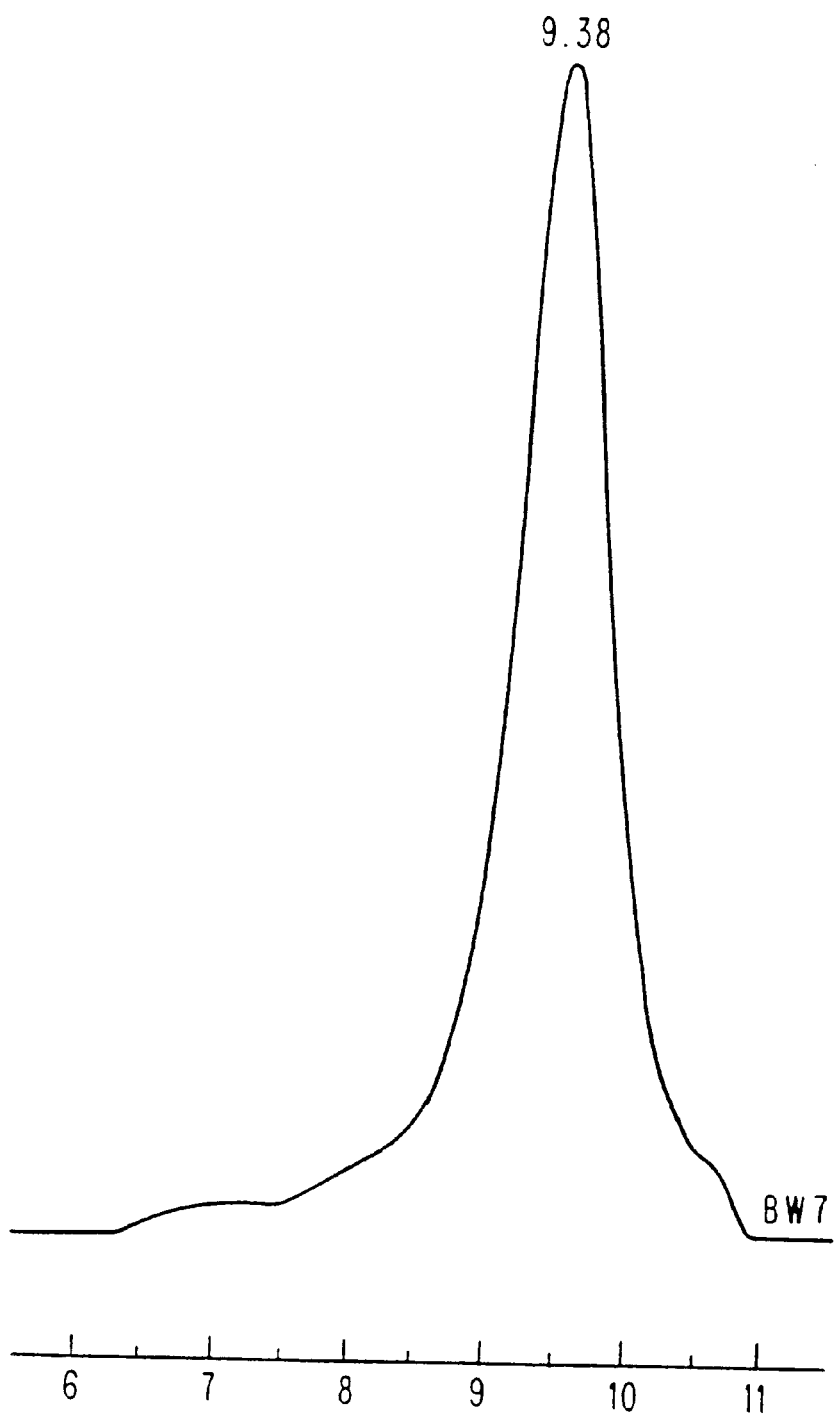
FIG. 1 illustrates the molecular weight distribution as a function of monomer concentration of poly (Asp.Bz-co-Phe) polymer prepared by the NCA method as described in Example 3.

All patents and literature references cited in this specification are hereby incorporated by reference in their entirety. In case of inconsistencies, the present description, including the definitions and interpretations, will prevail.

The instant invention arose from the discovery that proteinoids of a MW of between about 250 and about 2400 daltons and of defined amino acid composition can be obtained by modifying known reactions and selecting starting materials. These proteinoids form proteinoid carriers with surprisingly enhanced stability against at least one of photodegradation and decomposition over time. In addition, proteinoid carriers prepared from such proteinoids carry a broader range of pharmaceutical agents, including labile polypeptides such as insulin, alpha-interferon, calcitonin, antigens, e.g. influenza virus M1-protein, and Factor IX and display a selective releasability within various portions of the gastrointestinal tract, relative to prior art proteinoid microspheres.

The proteinoids of the invention comprise a peptide polymer selected from the group consisting of:
(i) peptide polymers made from at least one first monomer selected from the group consisting of tyrosine and phenylalanine; and from at least one second monomer selected from the group consisting of glutamic acid, pyroglutamic acid, glutamine, and aspartic acid;
(ii) peptide polymers made from at least one first monomer selected from the group consisting of tyrosine and phenylalanine; at least one second monomer selected from the group consisting of glutamic acid, pyroglutamic acid, glutamine, and aspartic acid; and from at least one third monomer selected from the group consisting of lysine, arginine and ornithine, the proteinoid being a microsphere- or microcapsule-forming proteinoid and being soluble within a selected pH range.

The proteinoid molecules of the invention contain between about 2 and about 20 amino acid residues, preferably between about 2 and about 8 amino acid residues, and have a molecular weight which ranges between about 250 and about 2400 daltons, preferably between about 250 and about 600, and most preferably between about 250 and 400 daltons.

Proteinoid carriers prepared from the proteinoid molecules, in accordance with the present invention, display a selective solubility at specific acidic or basic pH ranges, depending on the choice and amount of the second and third monomers in the proteinoid.

Proteinoid carriers which are selectively soluble under alkaline pH environments, such as those found in the distal portion of the intestine, are prepared from base-soluble proteinoids. These proteinoids contain, as starting monomers in the reaction mixture, at least one second monomer selected from the group consisting of glutamic acid, glutamine, pyroglutamic acid, and aspartic acid. At a pH ranging between about 7.2 and about 11.0, the base-soluble proteinoid exists largely as the anion and is soluble. At a pH below about 7.0, the proteinoid is largely protonated and insoluble in water.

Similarly, proteinoid carriers which are selectively soluble under acidic pH environments, such as the stomach, are prepared from acid-soluble proteinoids. In this case, the proteinoid contain, as starting monomers in the proteinoid reaction mixture, at least one second monomer selected from the group consisting of glutamic acid, pyroglutamic acid, glutamine, and aspartic acid and at least one third monomer selected from the group consisting of lysine, arginine, and ornithine. At a pH ranging between about 1 and about 7, the base-soluble proteinoid exists largely as the cation and is soluble. At a pH above about 7.2, the proteinoid is largely unprotonated and insoluble in water.

The pH and the solubility characteristics of the acid-soluble proteinoid depends largely, but not exclusively, upon the pH and solubilty of the last amino acid added during the synthesis of the proteinoid. For instance, the incorporation of a basic amino acid, e.g., a third monomer, selected from the group consisting of lysine, arginine and ornithine in the acid-soluble proteinoid will result in the elevation of the pI (pH at the isoelectric point) of the proteinoid.

The proteinoids of the present invention are preparable by a thermal condensation reaction by heating mixtures of the appropriate amino acids under conditions described in the '673 patent. In contrast with the '673 patent procedures which use as many as eighteen amino acids, mixtures of two to five specific amino acids with at least one selected from each of the aforementioned groups yield proteinoids which form proteinoid carriers with selective solubility at particular pH ranges and at high yields.

In carrying out the thermal condensation reaction, it has now been discovered that inclusion of tetramethylene sulfone, an inert, high boiling, polar solvent, maximizes the yield (>80%) of low MW proteinoids. Omission of solvent does not produce high yields of low MW proteinoids. Presumably this is due to the poor solubility of the amino acid monomers in these solvents and/or unavoidable side reactions between the monomers and the solvent under the reaction conditions.

In general, individual amino acids are added to a reaction flask containing tetramethylene sulfone (sulfolane) which has been heated to a temperature ranging between about 130° C. and about 200° C., preferably about 175° C. to 195° C., under an inert atmosphere of argon or nitrogen gas. After each addition, the solution is stirred for a period of time ranging between about 10 minutes and about 5 hours, depending on the amino acid type and the order of addition.

Upon heating mixtures of amino acids to temperatures of about 190° C. as described above, a reaction takes place and water, ammonia and carbon dioxide are produced as side-products. Water is removed from the reaction as formed and the reaction is terminated when water formation ceases. Thereafter, the proteinoid are precipitated out of the reaction solution by quenching with excess water, under vigorous stirring. After stirring for a period of about 1 hour, the proteinoids are collected by filtration, washed with water and dried under vacuum.

Chemical condensation methods which utilize derivatized amino acids are also useful for making the proteinoids of the present invention as they permit greater control of molecular weight. Such reactions are generally conducted at lower reaction temperature and with initiators. In particular, low MW proteinoids produced by the alpha-amino acid N-carboxyanhydride (NCA) method and the diphenylphosphoryl azide (DPPA) method (N. Nishi et al. (1991) *Makromol. Chem.*, Vol. 192, pages 1789–1798) were found to form proteinoid carriers having selected solubility within a particular pH range.

The NCA method involves the preparation of N-carboxyanhydrides of alpha-amino acid esters and their subsequent polymerization, using low MW amines as initiators. It has been discovered that non-NCA derived amino esters, e.g., α-methyl tyrosine ester, are effective initiators which are stable and soluble in many organic solvents such as tetrahydrofuran (THF). The use of amino acids as initiators, presumably due to their poor solubility in organic solvents and their low stability, are not known. The NCA reaction produces a high yield of proteinoids with high purity.

The DPPA method involves the direct condensation of benzyl esters of alpha-amino acids in the presence of DPPA and a low MW amine, followed by removal of the protective benzyl groups, contained in the proteinoid product, by alkaline hydrolysis. If catalytic hydrogenation is used in place of alkaline hydrolysis, low MW proteinoids of unexpected high purities and yields are obtained.

Proteinoids prepared by any of the above methods can be used immediately to microencapsulate an active pharmacological agent or the proteinoid can be concentrated or dried by conventional means and stored for future use.

The proteinoids of the invention are purified as follows: crude proteinoids are slurried with water at room temperature, e.g. 25° C. While at this temperature, the pH of the slurry is adjusted to about pH 8 using an aqueous alkaline solution, e.g. 40%. sodium hydroxide and 10% sodium bicarbonate solutions for an acid-soluble proteinoid. For a base-soluble proteinoid, the slurry is adjusted to an acidic pH with an aqueous acidic solution, e.g. 10% acetic acid solution. The mixture is then filtered and the filter cake washed with a volume of water. The washes and filtrate are then combined and evaporated to dryness in vacuo to afford proteinoids. If necessary, this process can be repeated until proteinoids of a desired purity level are obtained.

If desired, the proteinoid may be further purified by fractionating on a column containing solid supports which include silica gel or alumina, using methanol or propanol as mobile phase; ion exchange resin using water as the mobile phase; reverse phase column supports using trifluoroacetic acid/acetonitrile mixtures as mobile phase. The proteinoids may also be purified by extraction with a lower alcohol such as propanol or butanol to remove low molecular weight contaminants.

Proteinoid carriers are made from purified proteinoids as follows: proteinoids are dissolved in deionized water at a concentration ranging between about 75 and about 200 mg/ml, preferably about 100 mg/ml, at a temperature between about 25° C. and about 60° C., preferably about 40° C. Particulates remaining in the solution may be filtered out by conventional means such as gravity filtration over filter paper.

Thereafter, the proteinoid solution, maintained at a temperature of about 40°C., is mixed with an aqueous acid solution (also at about 40°C.) having an acid concentration ranging between about 1 N and about 2 N, preferably about 1.7 N. The resulting mixture is further incubated at 40° C. for a period of time effective for microsphere and microcapsule formation as observed by light microscopy. In practicing this invention, the preferred order of addition is adding the proteinoid solution to the aqueous acid solution.

Suitable acids include any acid which does not (a) adversely effect the proteinoid, e.g., chemical decomposition; (b) interfere with microsphere or microcapsule formation; (c) interfere with microsphere or microcapsule encapsulation of cargo; and (d) adversely interact with the cargo. Preferred acids for use in this invention include acetic acid, citric acid, hydrochloric acid, phosphoric acid, malic acid and maleic acid.

In practicing the invention, a proteinoid carrier stabilizing additives are preferably incorporated into the aqueous acid solution or into the proteinoid solution, prior to the microsphere or microcapsule formation process. The presence of such additives promotes the stability and dispersibility of the proteinoid carriers in solution.

The additives may be employed at a concentration ranging between about 0.1 and 5% (W/V), preferably about 0.5% (W/V). Suitable, but non-limiting, examples of stabilizing additives include gum acacia, gelatin, polyethylene glycol, and polylysine.

Thereafter, the proteinoid carriers may be used immediately or may be stored at 4° C. or lyophilized and stored under desiccant at room temperature or below.

Under the aforementioned conditions, the proteinoid molecules form spherical proteinoid carriers comprising proteinoid microcapsules and proteinoid microspheres of less than 10 micron diameter. As defined herein, a "microsphere" is spherical homogeneous mesh work structure having no discrete inner chamber. A "microcapsule" refers to a spherical structure having a proteinoid wall which forms a hollow or chamber. If the proteinoid carriers are formed in the presence of a soluble material, e.g., a pharmaceutical agent in the aforementioned aqueous acid solution, this material is believed to be encapsulated within the hollows of the microcapsules and confined within the proteinoid wall defined by the spherical structure or entrapped within the matrix of proteinoid molecules in the microsphere structure. In this way, one can encapsulate or entrap pharmacologically active materials such as peptides, proteins, and polysaccharides as well as charged organic molecules, e.g., quinolones or antimicrobial agents, having poor bioavailability by the oral route. The amount of pharmaceutical agent which may be encapsulated or entrapped by the proteinoid carrier is dependent on a number of factors which include the concentration of agent in the encapsulating solution.

The proteinoid carriers of the invention are pharmacologically harmless and do not alter the physiological and biological properties of the active agent. Furthermore, the encapsulation process does not alter the pharmacological properties of the active agent. While any suitable pharmacological agent can be encapsulated within proteinoid carriers, it is particularly valuable for delivering agents which otherwise would be destroyed or rendered less effective by conditions encountered in the animal body before it reaches its target zone and which are poorly absorbed in the gastrointestinal tract.

The proteinoid carriers of the invention are particularly useful for the oral administration of certain pharmacological agents, e.g., small peptide hormones, which, by themselves, pass slowly or not at all through the gastro-intestinal mucosa and/or are susceptible to chemical cleavage by acids and enzymes in the gastrointestinal tract. Non-limiting examples of such agents include human or bovine growth hormone, interferon and interleukin-II, calcitonin, atrial natriuretic factor, antigens, monoclonal antibodies, and Factor IX, a vitamin K-dependent blood coagulation proenzyme.

The choice of a particular proteinoid for use in encapsulating or entrapping a pharmacological agent depends on a number of factors which include:

(1) the acidity or basicity of the agent;
(2) the targeted area for release in the gastrointestinal tract;
(3) the solubility of the drug at certain pH ranges;
(4) efficiency of encapsulation;
(5) interaction of drug with proteinoid.

For example, proteinoids made from glutamic acid, aspartic acid, tyrosine, and phenylalanine are especially suitable for encapsulating polysaccharides like heparin.

In addition to selective pH solubility, the particle size of the proteinoid carrier plays an important role in determining release of the active agent in the targeted area of the gastrointestinal tract. Proteinoid carriers having diameters between about $\leq 0.1$ microns and about 10 microns, preferably between about 5.0 microns and about 0.1 microns, and containing encapsulated or entrapped active agents are sufficiently small to effectively release the active agent at the targeted area within the gastrointestinal tract. Large proteinoid carriers (>10 microns) tend to be less effective as oral delivery systems.

The size of the proteinoid carriers formed by contacting proteinoids with water or aqueous solution containing active agents can be controlled by manipulating a variety of physical or chemical parameters, such as the pH, osmolarity or salt content of the encapsulating solution, and the choice of acid used in the encapsulating process.

By tailoring both the solubility characteristics of a proteinoid and the particle size of the proteinoid carriers, active agent bearing proteinoid carriers can be produced from base-soluble proteinoids which are stable in the highly acidic stomach (normal pH of from about 2 to about 6), but which dissolve in the distal portion of the intestines. Such systems are suitable for oral administration of peptide hormones, e.g., insulin, and polysaccharides, e.g., heparin, which otherwise would be quickly destroyed in the GI tract. They also are suitable for protecting the stomach from gastric irritants, such as aspirin. When such aspirin-containing proteinoid carriers are orally administered, they pass through the gastrointestinal mucosa and release the aspirin far more rapidly than conventional enterically coated aspirin, which first must traverse the stomach and then must enter the bloodstream from the intestine after the enteric coating has dissolved.

It also is possible to produce systems from acid-soluble proteinoids which are stable under weakly basic conditions (pH of about 8), but which release active agent under acidic conditions (pH of about 2 to 5). Such systems are suitable for the intravenous administration of pharmacological agents such as calcium regulators and redox carrier systems for dopamine or gamma-aminobutyric acid.

The proteinoid carriers of the invention may be orally administered alone as solids in the form of tablets, pellets, capsules, and granulates suitable for suspension in liquids such as edible oils. Similarly, the proteinoid carriers can be formulated into an orally administrable composition containing one or more physiologically compatible carriers or excipients. These compositions may contain conventional ingredients such as gelatin, polyvinylpyrrolidone and fillers such as starch and methyl cellulose.

The proteinoid carriers of the invention may also be administered by injection.

The following examples are illustrative of the invention but are not intended to limit the scope of the invention.

EXAMPLE 1

Preparation of a Base-soluble Proteinoid by a Thermal Condensation Reaction 750 ml of tetramethylene sulfone was heated to 190° C. in an inert nitrogen atmosphere in a 4 liter flask with stirring. 294 g of glutamic acid was added and the mixture was heated for one-half hour. 266 g of aspartic acid was added and the mixture heated as rapidly as possible to 190° C. and held there for 15 minutes. 362 g of tyrosine was added and the mixture heated at 190° C. for 3 hours. 330 g of phenylalanine was added and the mixture heated at 190° C. for 1.5 hours. The hot melt was then poured into 5 liters of water with vigorous stirring. After stirring for about 1 hour, the mixture was filtered and the filtrate discarded. The cake was reslurried in 5 liters of water, filtered and the cake was again reslurried in 5 liters of water. The pH of the slurry (at 25° C.) was adjusted to 8 using 40% sodium hydroxide solution. The mixture was filtered and the cake washed with a small amount of water. The washes and filtrate are combined and evaporated to dryness in vacuo to give Glu/Asp/Tyr/Phe proteinoid.

Appendices A, B, and C describe examples of other proteinoids prepared by the thermocondensation method.

EXAMPLE 2

Preparation of an Acid-soluble Proteinoid by a Thermal Condensation Reaction 750 ml of tetramethylene sulfone is heated to 190° C. in an inert nitrogen atmosphere in a 4 liter flask with stirring. 294 g of glutamic acid is added and the mixture is heated for one-half hour. 362 g of tyrosine is added and the mixture is heated at 190° C. for 3 hours. 330 g of phenylalanine is added and the mixture is heated at 190° C. for 1.5 hours. 266 g of arginine is added and the mixture is heated for an additional 1.5 hours. The hot melt is then poured into 5 liters of water with vigorous stirring. After stirring for about 1 hour, the mixture is filtered and the filtrate is discarded. The cake is reslurried in 5 liters of water, filtered and the cake is again reslurried in 5 liters of water. The pH of the slurry (at 250° C.) was adjusted to 5 using 10% acetic acid solution. The mixture is filtered and the cake is washed with a small amount of water. The washes and filtrate are combined and evaporated to dryness in vacuo to give proteinoid.

Appendices A, B, and C describe examples of other proteinoids prepared by the thermocondensation method.

EXAMPLE 3

Preparation of Proteinoids by the NCA Method Using Amine Initiator

This example illustrates the NCA method for preparing copolypeptides consisting of Asp.Bz, Glu.Bz, Phe, and Tyr components. The NCA monomers of these amino acids were prepared according to the reported method.

The reactions were carried out in tetrahydrofuran (THF) or in dichloromethane using benzylamine ($BzNH_2$) or 4-methylbenzyl amine ($MeBzNH_2$) as initiator at room temperature ([M]=10%). The characterization of the resulting copolymers was performed by $^1H$ NMR and GPC. The results obtained are listed in Table 1.

As shown in Table 1, proteinoids having Asp and/or Glu as the second monomers and Phe and/or Tyr as the first monomers were obtained in high yield from the polymerization initiated with BzNH$_2$ at the ratio of [M]/[I]=5 (No. 2-1 to 2-7).

The GPC curve (FIG. 1) for poly(Asp.Bz-co-Phe), from which a polydispersity of 1.91 was determined. Similar molecular weight distributions were observed for other copolymers.

Polydispersity is defined herein as the molecular weight distribution of a sample. The distribution is assigned a numerical value derived from the molecular weight (MW) divided by the molecular number (Mn). The polydispersity value for a homopolymer is 1 because the molecular weight is equal to the molecular number. Any polymer with a polydispersity value of 1 is considered to have a very narrow distribution. A polymer with polydispersity value of 1.6 to 1.7 is considered to have medium distribution. A polymer with a polydispersity value of 2.0–2.1 is considered to have a broad distribution.

The homopolymerization of NCA of Asp.Bz and the copolymerizations of NCAs of Asp.Bz, Glu.Bz, Phe, and Tyr were also carried out using MeBzNH$_2$ as initiator (No. 2-11, 2-15, and 2-16). Similar results were obtained for reactions initiated by BzNH$_2$.

TABLE 1

COPOLYMERIZATION OF NCAs INITIATED WITH AMINES STORED AT ROOM TEMPERATURE FOR 4 DAYS

| POLYM. NO. | COMONOMER COMPOSITION | INITIATOR ([M]/[I]) | SOLVENT | YIELD (%) | $M_W$ |
|---|---|---|---|---|---|
| 2-1 | Asp-Glu-Phe-Tyr (1:1:1:1) | BzNH$_2$ (5:1) | THF | 84.1 | 830 |
| 2-2 | Asp-Phe (1:1) | BzNH$_2$ (5:1) | THF | 70.9 | 730 |
| 2-3 | Asp-Tyr (1:1) | BzNH$_2$ (5:1) | THF | 88.6 | 1000 |
| 2-4 | Asp-Tyr (2:1) | BzNH$_2$ (5:1) | THF | 89.3 | 1050 |
| 2-5 | Glu-Tyr (1:1) | BzNH$_2$ (5:1) | THF | 84.9 | 870 |
| 2-6 | Glu-Phe-Tyr (2:1:1) | BzNH$_2$ (5:1) | CH$_2$Cl$_2$ | 68.8 | 790 |
| 2-7 | Glu-Phe-Tyr (1:1:1) | BzNH$_2$ (5:1) | CH$_2$Cl$_2$ | 53.7 | 1000 |
| 2-11 | Asp | MeBzNH$_2$ (5:1) | THF | 88.3 | 870 |
| 2-15 | Asp-Glu-Phe-Tyr (1:1:1:1) | MeBzNH$_2$ (5:1) | THF | 76.4 | — |
| 2-16 | Asp-Glu-Phe-Tyr (1:1:1:1) | MeBzNH$_2$ (5:1) | THF | 76.4 | 630 |

EXAMPLE 4

Preparation of Proteinoids by the NCA Method

Using α-Methyl Tyrosine Ester as Initiator

This example illustrates the method of conducting NCA polymerizations, using α-methyl tyrosine ester (Tyr.Me) as the initiator. The reaction conditions are essentially the same as described in Example 4 except tetrahydrofuan (THF) solvent was used. The results are listed in Table 2.

TABLE 2

PROTEINOID SYNTHESIS BY NCA INITIATED WITH AMINO ACIDS STORED AT ROOM TEMPERATURE FOR 4 DAYS

| POLYM. NO. | COMONOMER COMPOSITION | INITIATOR ([M]/[I]) | SOLVENT | YIELD (%) | $M_W$ |
|---|---|---|---|---|---|
| 2-8 | Asp-Glu-Phe (1:1:1) | Tyr.Me (1:1) | CH$_2$Cl$_2$ | 100 | 450 |
| 2-9 | Asp-Glu-Phe (1:1:1) | Tyr.Me (3:1) | CH$_2$Cl$_2$ | 71.4 | 450 |
| 2-10 | Asp-Glu-Phe (1:1:1) | Tyr.Me (5:1) | CH$_2$Cl$_2$ | 68.0 | 730 |
| 2-12 | Asp | Tyr.Me (1:1) | THF | 100 | 460 |
| 2-13 | Glu-Tyr (1:1) | β-Ala (2:1) Suc.An (2:1) | THF (reflux) | 67.4 | 480 |
| 2-14 | Asp | Tyr.Me (6:1) | THF | 91.8 | 890 |
| 2-17 | Phe | Tyr.Me (1:1) | THF | 73.0 | ND |
| 2-18 | Tyr | Tyr.Me (1:1) | THF | 65.7 | ND |
| 2-19 | Phe | Tyr.Me (5:1) | THF | 78.3 | ND |
| 2-20 | Tyr | Tyr.Me (5:1) | THF | 63.3 | ND |

It was found that the initiation by Tyr.Me is very fast (No. 2-17 to 2-20) and all the NCA has been converted after 2 hours. From GPC data, it was observed that the molecular weight of the polymer increased with increasing ratio of [M]/[Tyr.Me] and the polydispersity is quite narrow. The existence of a Tyr.Me residue in the polymers was confirmed by $^1$H NMR spectra. In conclusion, Tyr.Me is a novel and effective initiator for the polymerization of amino acid NCA's.

Sample No. 2-13 represents a polymerization initiated with β-alanine and terminated with succinic anhydride. As β-alanine is insoluble in most organic solvents, the reaction was carried out in refluxing THF. As a result, the polydispersity of the polymer obtained was broader than that of the polymers initiated by Tyr.Me.

EXAMPLE 5

Preparation of Proteinoids by the DPPA Method (#1)

This is an example of a direct polycondensation of Asp.Bz in the presence of DPPA and triethylamine (TEA) as a base under various polymerization conditions ((a), (b), (c), and (d)). The molecular weight of the polymers, as well as polydispersity, was evaluated in each case by GPC. The polymers were characterized by IR and NMR spectroscopy.

Asp.Bz was prepared by the esterification of L-aspartic acid as follows: L-aspartic acid (26.6 g, 0.2 mole) was suspended in 300 ml of freshly distilled benzyl alcohol in a 500 ml round bottom flask, followed by addition of 45 ml of concentrated hydrochloric acid (12N). The mixture was heated up to 60° C. under vigorous stirring for 30 minutes. Thereafter, the reaction solution cooled to room temperature. Triethyl amine (about 56 ml) was added to neutralize (to a pH of about 7) the solution. The crude product was collected by filtration, washed with ethanol and acetone, dried in vacuo, and crystallized twice from hot water. 18 g of product was obtained (% yield=44%). M.pt=217° C.

Commercial DPPA was used without further purification. TEA was distillated before use. Solvents for polymerization were purified by conventional methods. The direct polycondensation of Asp.Bz was carried out by stirring a dimethyl formamide (DMF) solution of the monomer in the presence of DPPA and TEA. The mixture was stirred for 1 h at 0–10° C. followed by stirring at room temperature for two days. The resulting polymer was precipitated in a large amount of water, collected by filtration, and then dried in vacuo.

a. Effect of Monomer Concentration

Listed in Table 3 are the results for the polymerization of Asp.Bz in DMF at room temperature for two days. Poly(Asp.Bz)s were obtained from these direct polycondensations in high yield.

Figure 2:
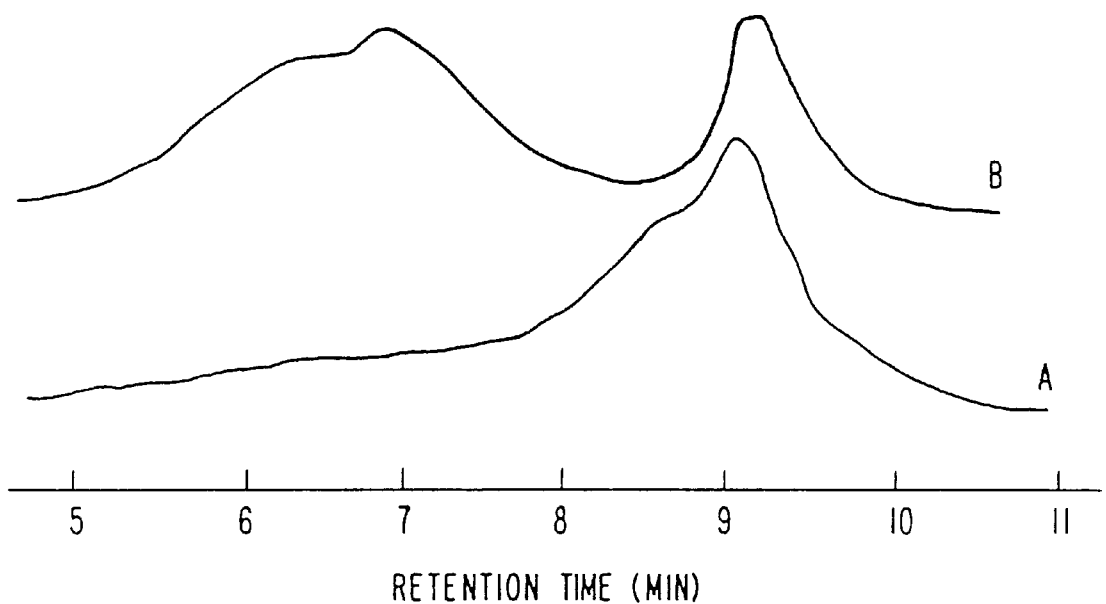
FIG. 2 illustrates the molecular weight distribution of a function of monomer concentration of poly (Asp.Bz) polymer prepared by the DPPA method as described in Example 5.

The molecular weight of the polymers was found to be dependent on the concentration of the monomer [M]. Low molecular weight polymers with broad distribution were obtained from a low [M] (FIG. 2, curve A). On the other hand, when [M] was greater than 0.2 g/mL, a polymer with a bimodal molecular weight distribution was obtained (FIG. 2, curve B). The lower molecular weight oligomers (~1000) may be due to an intramolecular termination between the terminal amino and the β-carboxylic groups. After several reprecipitations from THF/methanol, a polymer with a higher molecular weight ($M_n$=22,000) and narrow polydispersity ($M_w/M_n$=1.68) was successfully isolated from the polymer mixture prepared at [M]=1 g/mL. The separation was also performed using GPC column with Bio-Beads.

TABLE 3

EFFECT OF THE MONOMER CONCENTRATION ON POLYMERIZATION OF Asp.Bz BY DPPA IN DMF AT ROOM TEMPERATURE: [DPPA]/[M] = 1.3; [TEA]/[M] = 2.3

| [M] (g/ml) | YIELD (%) | $M_n \times 10^{-3(c)}$ | $M_w/M_n$ |
|---|---|---|---|
| 0.025 | 71.5[a] | 1.4 | 4.15 |
| 0.033 | 74.7[a] | 1.0 | 3.50 |
| 0.05 | 67.2[a] | 1.1 | 5.11 |
| 0.10 | 63.2[b] | 0.91 | 3.70 |
| 0.20 | 85.4[b] | 16.3 (60.7), 1.0 (39.3) | 1.84, 1.13 |
| 0.50 | 86.5[b] | 11.0 (59.4), 0.92 (40.6) | 2.22, 1.08 |
| 1.0 | 97.6[b] | 15.1 (71.4), 0.88 (28.6) | 1.81, 1.05 |

[a]The polymer was collected by centrifugation after polymerization for 2 days;
[b]The polymer was collected by filtration after polymerization for 2.5 days.
[c]The values in parentheses are molar percentages.

b. Effect of Reaction Time and Temperature

Figure 3:
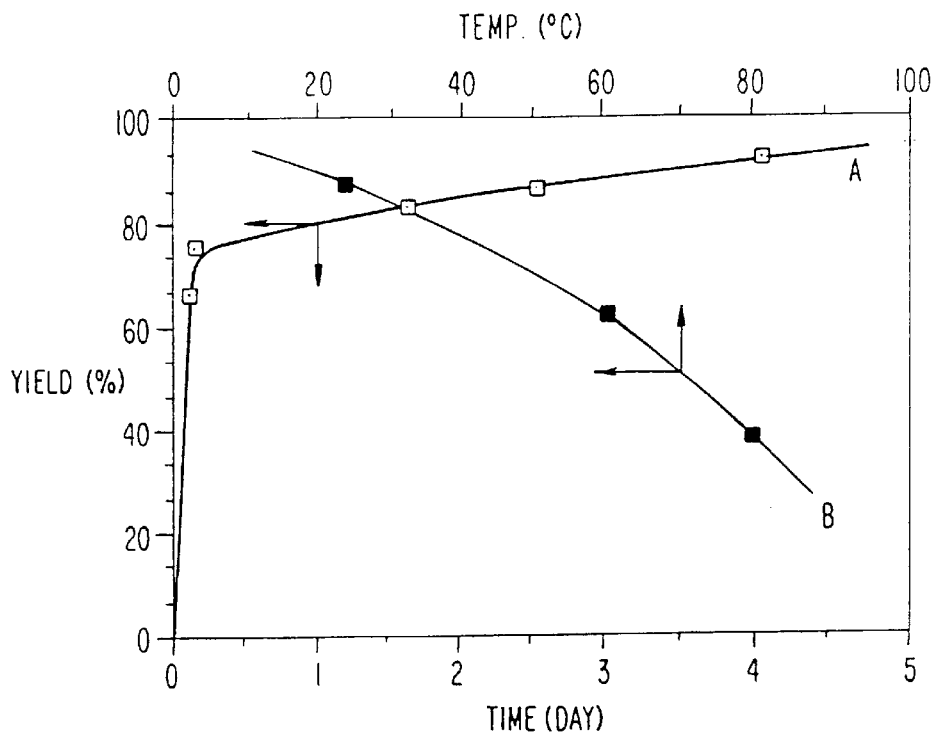
FIG. 3 illustrates the effect of reaction time duration on yields of poly (Asp.Bz) polymer prepared by the DPPA method as described in Example 5.
Figure 4:
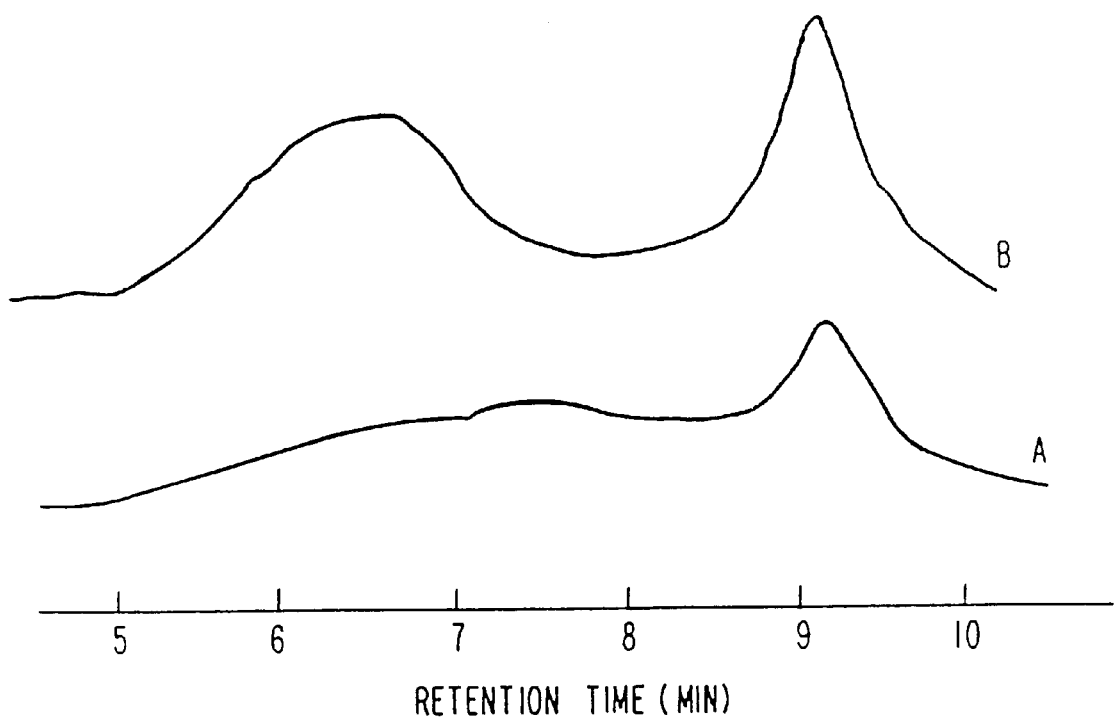
FIG. 4 illustrates the effect of temperature of the molecular weight of poly (Asp.Bz) polymer prepared by the DPPA method as described in Example 5.
Figure 7:
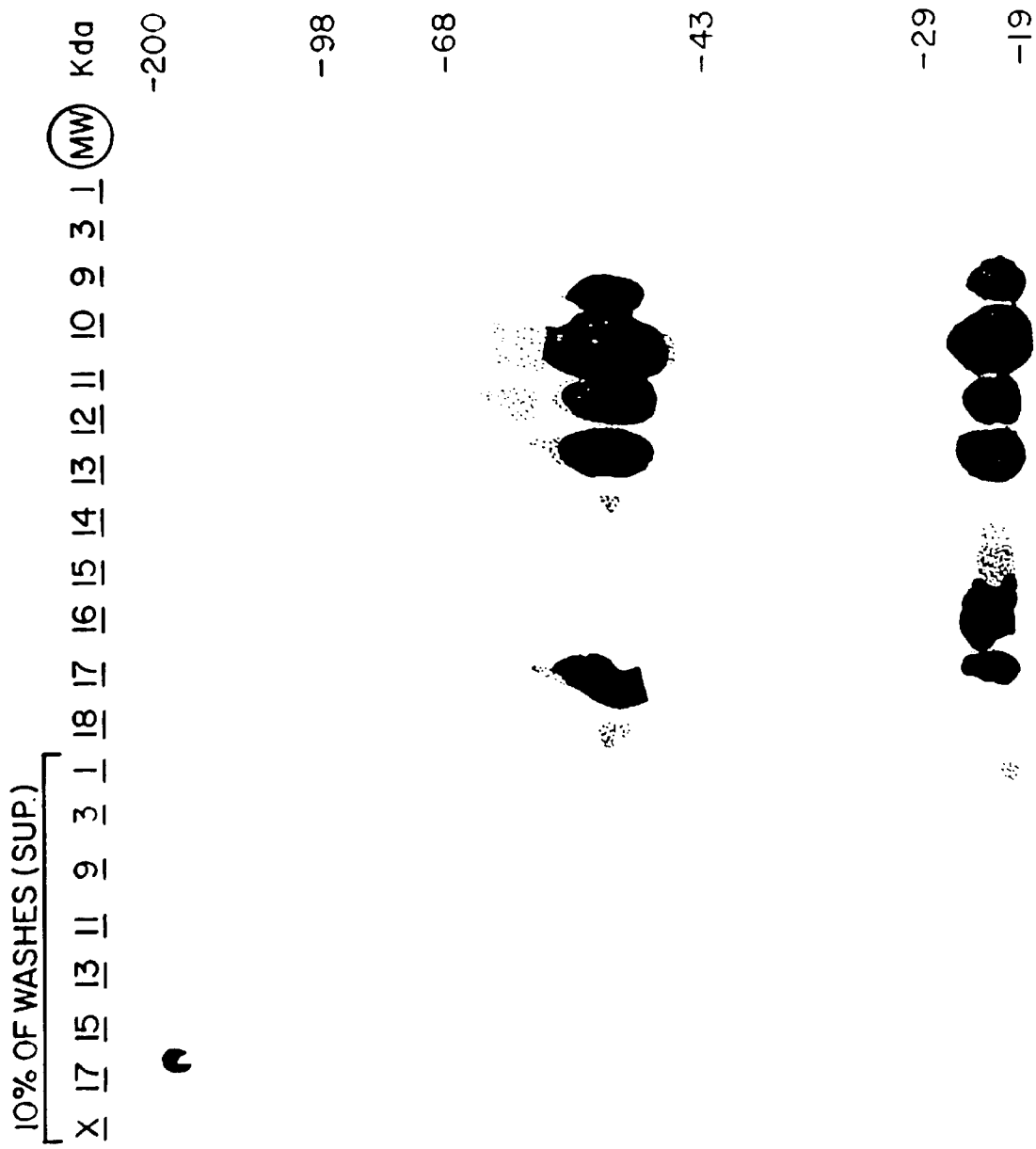
FIG. 7 is a photograph of an x-ray film of a western immunoblot analysis of samples described in Example 10.
Figure 8A:
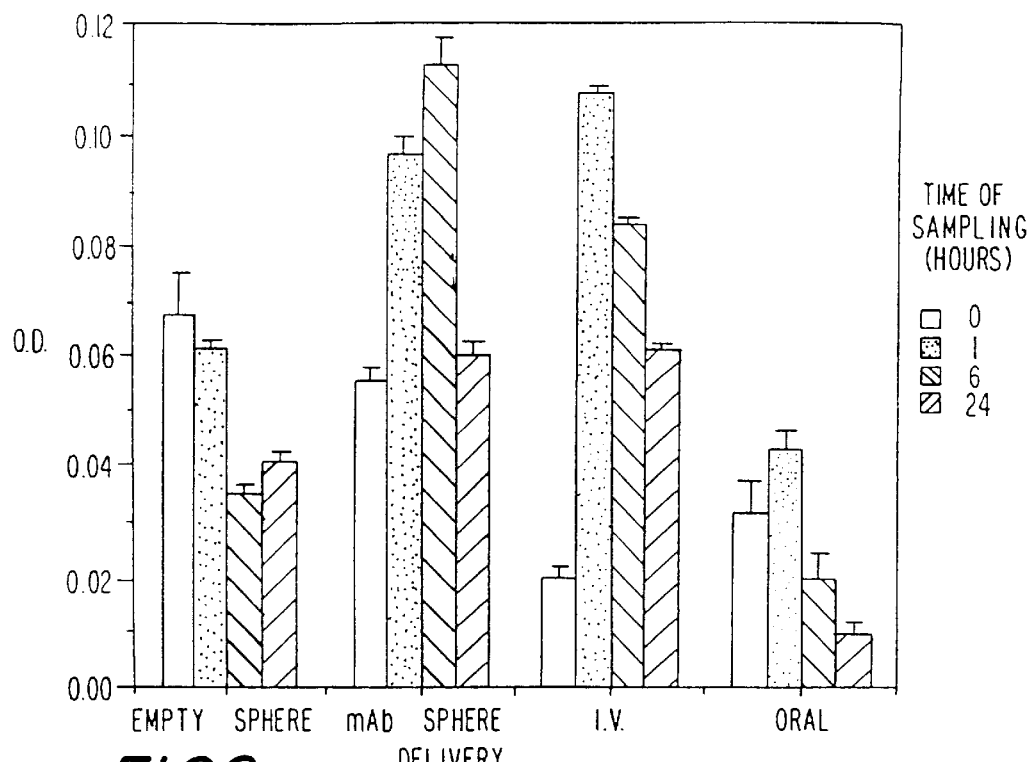
FIGS. 8($a$–$c$) illustrate the levels of serum proteins which bound to immobilized reovirus type 3 and $V_L$SH under ELISA conditions as described in Example 11. "Empty spheres" refers to animals orally administered empty proteinoid carriers (no mAb 9BG5); "mAb spheres" refers to animals orally administered mAb 9BG5 encapsulated proteinoid carriers; "IV" refers to animals intravenously administered unencapsulated mAb 9BG5; and "oral" refers to animals orally administered unencapsulated mAb 9BG5.
Figure 8B:
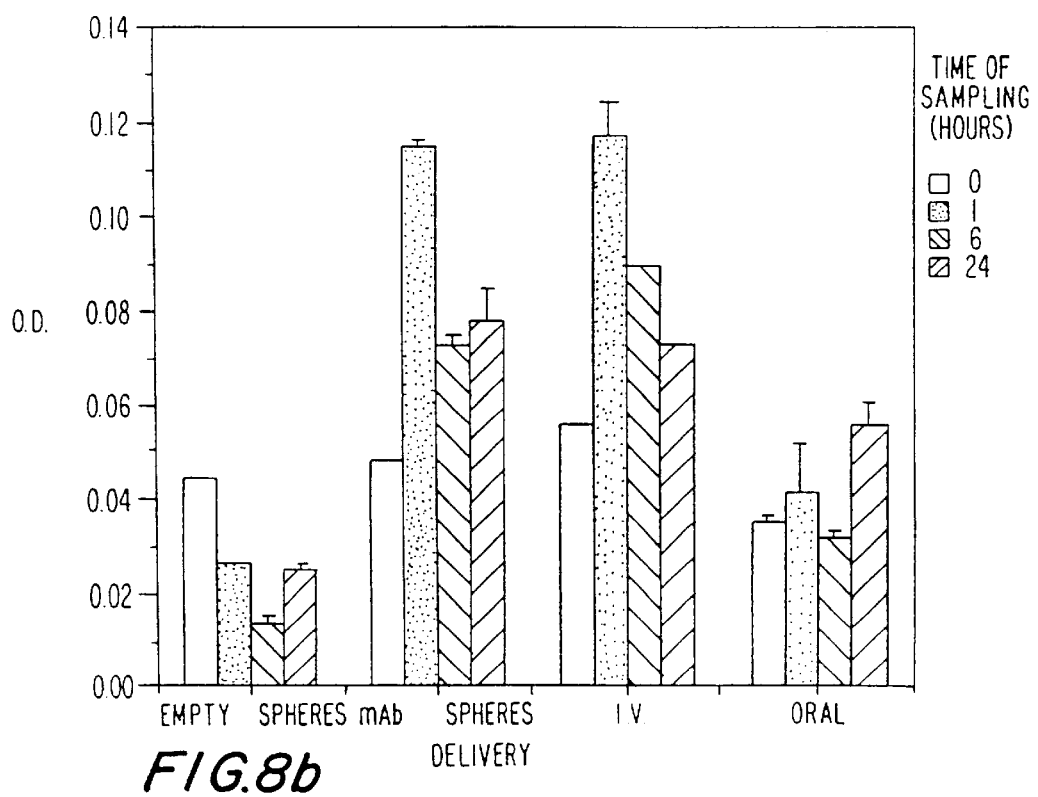
Figure 8C:
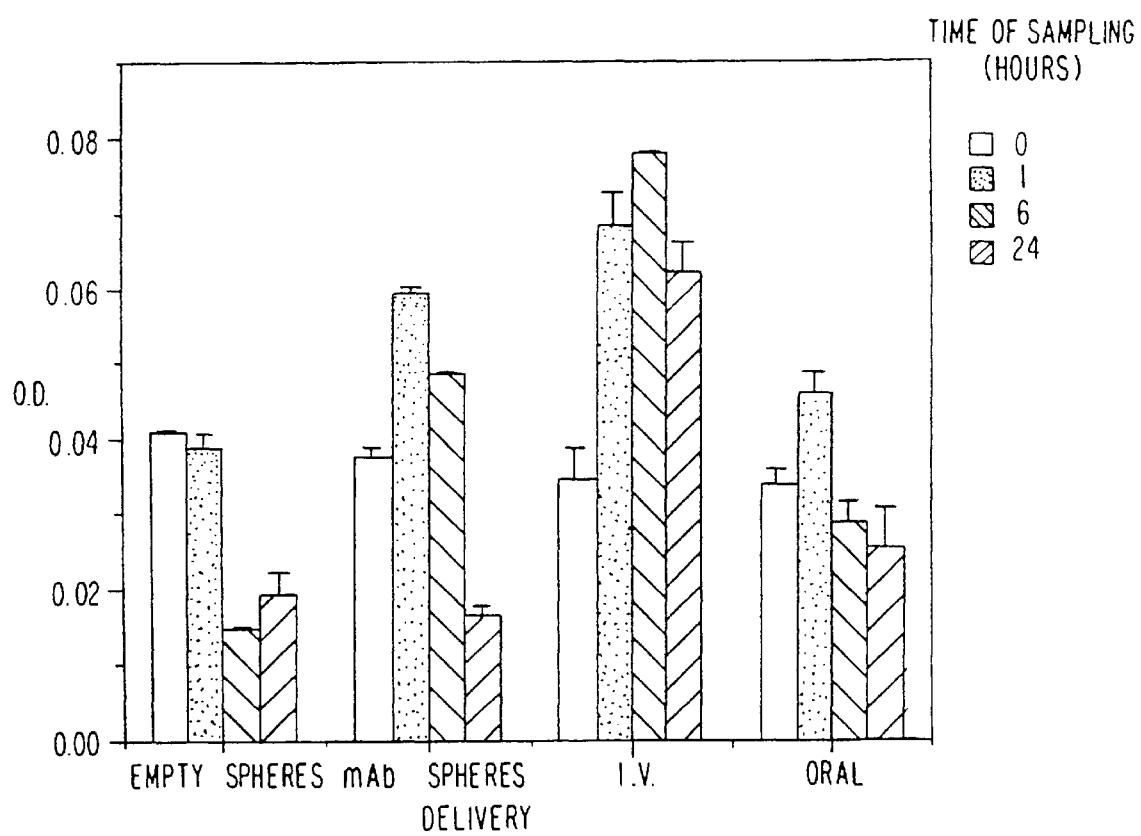

The yield of the resulting polymer increased with the reaction time: 75% conversion in 5 h and 95% in 4 days (FIG. 3, curve A). The molecular weight of the resulting polymer also increased with time in the initial phase (up to 4 h) and then became almost constant (FIG. 4). The polymerization decreased with increasing temperature (FIG. 3, curve B). Polymers obtained at 60 and 80° C. were of yellow color and insoluble in THF but soluble in DMF and DMSO. This may be due to the formation of an imide ring which has been reported to occur during thermal polycondensations of aspartic acid.

c. Effect of Molar Ratios [DPPA]/[M] and [TEA]/[M]

Figure 5:
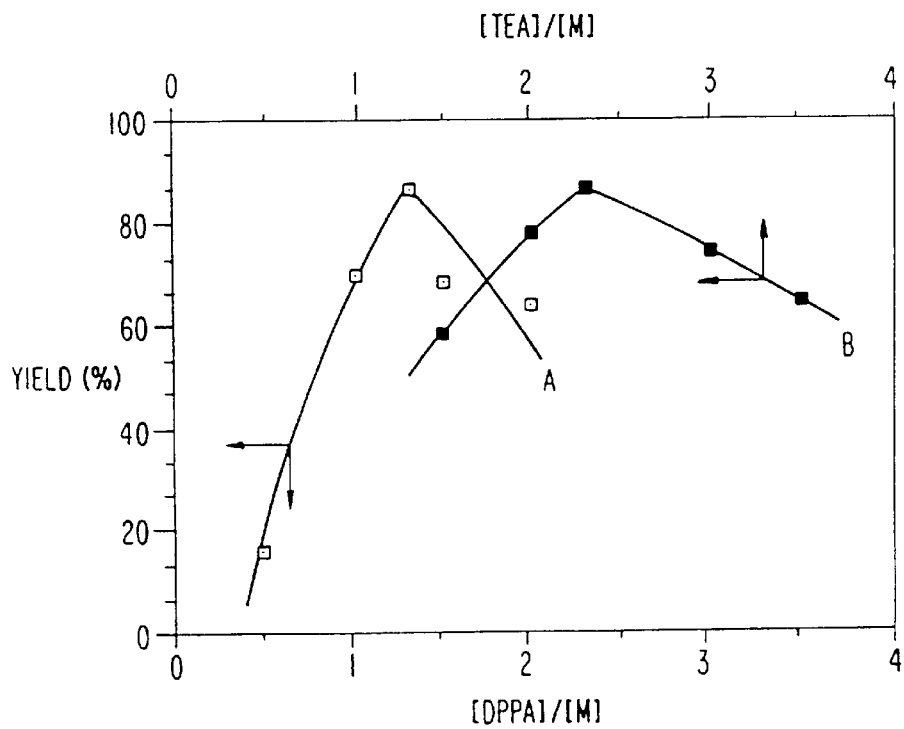
FIG. 5 illustrates the effect of changing the molar ratios of [DPPA]/[M] on the molecular weight of poly (Asp.Bz) polymer by the DPPA method as described in Example 5.

The dependence of the yield and the molecular weight of the polymer on the molar ratios of [DPPA]/[M], as well as [TEA]/[M], was investigated (Table 4). The highest yield was obtained at a [DPPA]/[M] of 1.3 and a [TEA]/[M] of 2.3 (FIG. 5). These observations are in agreement with the results reported by Nishi et al. Higher molecular weight products were obtained in the range of [DPPA]/[M]=1.3–2.0 and [TEA]/[M]=2.0–3.0, respectively.

TABLE 4

EFFECT OF THE MOLAR RATIOS OF DPPA AND TEA ON POLYMERIZATION OF Asp.Bz IN DMF AT ROOM TEMPERATURE: [M] = 0.50 g/ml

| [M]/DPPA | [M]/[TEA] | YIELD (%) | $M_n \times 10^{-3(a)}$ | $M_w/M_n$ |
|---|---|---|---|---|
| 0.5 | 2.3 | 16.3 | 0.81 | 4.09 |
| 1.0 | 2.3 | 69.6 | 3.1 (45.4), 0.39 (54.6) | 2.58, 1.48 |
| 1.3 | 2.3 | 86.5 | 11.0 (59.4), 0.92 (40.6) | 2.22, 1.06 |
| 1.5 | 2.3 | 69.4 | 15.9 (34.2), 0.83 (65.8) | 1.77, 1.21 |
| 2.0 | 2.3 | 64.3 | 13.1 (58.3), 0.89 (41.7) | 1.87, 1.09 |
| 1.3 | 1.5 | 58.4 | 6.0 (39.3), 0.63 (60.7) | 2.43, 1.37 |
| 1.3 | 2.0 | 78.3 | 13.3 (64.3), 0.92 (35.7) | 1.87, 1.19 |
| 1.3 | 3.0 | 74.6 | 13.6 (64.8), 0.83 (35.2) | 1.98, 1.18 |
| 1.3 | 3.5 | 65.0 | 8.3 (60.0), 0.80 (40.0) | 2.70, 1.10 |

[a]The value in parentheses are molar percentage.

d. Effect of Solvent

A comparison of the polymerizations in different solvents is shown in Table 5. It can be seen from this table that the yield and the molecular weight of the polymer are influenced by the solvents used. Higher yields were obtained in DMF while higher molecular weights were obtained in THF and in bulk. On the other hand, the polymerization in dioxane gave a lower molecular weight product, and therefore is preferred.

TABLE 5

EFFECT OF THE SOLVENTS ON POLYMERIZATION OF Asp.Bz AT ROOM TEMPERATURE FOR 2 DAYS [M]/[DPPA] = 1.3, [M]/[TEA] = 2.3, [M] = 0.50 g/ml

| SOLVENT | YIELD (%) | $M_n \times 10^{-3}$ [b] | $M_w/M_n$ |
|---|---|---|---|
| DMF | 86.5 | 11.0 (59.4), 0.92 (40.6) | 2.22, 1.08 |
| DMSO | 70.6 | 11.5 (78.9), 1.05 (21.1) | 1.87, 1.13 |
| THF | 49.9 | 29.6 (74.6), 1.14 (25.4) | 1.31, 1.13 |
| ACETONITRILE | 71.1 | 20.3 (79.3), 1.05 (20.7) | 1.65, 1.14 |
| DIOXANE | 70.5 | 4.7 (68.5), 0.82 (31.5) | 3.80, 1.13 |
| NONE[a] | 61.2 | 29.8 (82.8), 0.86 (17.2) | 1.32, 1.16 |

[a]Bulk polymerization.
[b]The value in parentheses are molar percentage.

EXAMPLE 6

Preparation of Proteinoids by the DPPA Method (#2)

Copolymerizations of Asp.Bz with other amino acid monomers such as γ-benzyl glutamate (Glu.Bz), β-alanine (Ala), Phenylalanine (Phe), and O-benzyl tyrosine (Tyr.OBz) in the presence of DPPA were carried out using the same procedure as that for the homopolymerization of Asp.Bz (Example 5). Random copoly(amino acids) were obtained in high yield (>77%) as shown in Table 6. This indicates that the copolymerization of amino acids using DPPA is a useful approach to copolypeptide synthesis. Bimodal molecular weight distributions were also observed in these cases similarly to the homopolymerization of Asp.Bz.

TABLE 6

COPOLYMERIZATION OF α-AMINO ACIDS IN THE PRESENCE OF DPPA AS CONDENSING AGENT IN DMF AT ROOM TEMPERATURE FOR 2 DAYS

| POLYM. NO. | COMONOMER COMPOSITION | YIELD (%) | $M_w$ | $M_w/M_n$ |
|---|---|---|---|---|
| Co.1DPPA | Asp.Bz-Glu.Bz (1:1) | 97.4 | 15900, 1080 | 1.76, 1.13 |
| Co.2DPPA | Asp.Bz-β-Ala (1:1) | 91.2 | 1590 | 1.18 |
| Co.3DPPA | Asp.Bz-Phe (1:1) | 89.7 | 13700, 800 | 1.89, 1.25 |
| Co.4DPPA | Asp.Bz-Tyr.OBz (1:1) | 87.3 | 9000, 1000 | 1.78, 1.17 |
| Co.5DPPA | Asp.Bz-Glu.Bz-Phe-Tyr.OBz (1:1:1:1) | 92.5 | 16800, 960 | 1.66, 1.14 |

EXAMPLE 7

Reductive Debenzylation of Proteinoids Produced by the DPPA Method

The example illustrates a preferred method for the removal of benzyl protective groups in poly(Asp.Bz) and poly(Glu.Bz) by catalytic hydrogenation.

The hydrogenation of the polymers was carried out according to the following procedure: To a solution of the polymer in THF/methanol (1:1, v/v), Pd on active carbon (10%) was added in the amount of 1/10 of the polymer weight. After the replacement of air by nitrogen, hydrogen gas was introduced into the system and maintained with a balloon. The reaction mixture was stirred at room temperature overnight. After removing the catalyst by filtration and concentrating the solution, the mixture was poured into a large amount of petroleum ether to precipitate the polymer. The polymer obtained was then dried in vacuo.

The completion of the hydrogenation was confirmed by $^1$H NMR of the polymer. In most cases, useful water-soluble polymers were produced. The hydrogenation is an effective and clean procedure for benzyl group removal.

EXAMPLE 8

Preparation of Empty Proteinoid Carriers with Glu, Asp, Tyr, Phe Proteinoid

This Example illustrates a method for the preparation and cleaning of empty proteinoid carriers.

PROCEDURE

1. Reagents:
   a. Proteinoid powder prepared as described in Example 1
   b. Anhydrous citric acid (USP)
   c. Gum acacia NF
   d. Deionized water
   e. Glatial acetic acid
2. Equipment:
   a. Ph meter
   b. Water bath, 40° C.
3. Preparation of Solutions:
   a. Proteinoid solution—Dissolve 100 mg proteinoid in 1 ml deionized water (or multiples thereof). Filter through a Whatman #1 filter paper (if necessary) and keep at 40° C. in a water bath. This is solution A.
   b. 1.7 N citric acid with 0.5% acacia—Dissolve 5 g of acacia and 109 g of citric acid in 1 liter deionized water. Incubate at 40° C. This is solution B.
4. Preparation of Proteinoid carriers:
   a. Add all of solution A to solution B rapidly in one step while swirling solution B by hand, in a 40° C. water bath.

EXAMPLE 9

Preparation of Murine IgG Monoclonal Antibody-containing Proteinoid Carrier

This experiment describes encapsulation of antireovirus monoclonal antibody (mAb)-9BG5, an mAb directed against the sigma-1 gene product (Hemaglutinin, HA3) of the Reovirus Type 3. HA3 binds to the cell surface receptor for Reovirus type 3, and mAb 9GB5 interferes with viral binding to the receptor.

Mouse IgG monoclonal antibody 9BG5 was prepared and purified as described W. V. Williams et al. (1991) *J. Biol. Chem.*, Vol. 266(8), pages 5182–5190, as well as references cited therein, using a purified Reovirus type 3 preparation (W. V. Williams et al. (1988) *Proc. Natl. Acad. Sci.* U.S.A, Vol. 85, pages 6488–6492). The purified 9BG5 used in this Example had a protein concentration of 1.5 mg/ml in phosphate buffered saline (pH 7.2).

Proteinoid carriers encapsulating mAb 9BG5 were prepared having final concentrations of Glu/Asp/Tyr/Phe proteinoid (1:1:1:1) mole ratio of Glu, Asp,Tyr, and Phe in the reaction mixture) 50 mg/ml, mAb 0.7 mg/ml and gum arabic 0.5% in 0.85 N citric acid. Empty proteinoid carriers were prepared to contain the same final concentrations, except mAb was omitted. Aliquots (0.5 ml), in duplicate, of both mAb and empty proteinoid carriers preparations were centrifuged at 5000 RPM. Pellets and supernatants were frozen prior to analysis by Western blotting to determine antibody encapsulation efficiency.

FIG. 6 is an x-ray film of a western blot analysis of purified mAb 9BG5, empty proteinoid carriers (no mAb added), and proteinoid carriers containing 9BG5. The analysis was done by immunoblotting with anti-mouse IgG which specifically reacted with mAb 9BG5. The lanes correspond to the following:

| Lane | Sample |
|---|---|
| 1 | 2 µg 9BG5 mAb |
| 2 | 1 µg 9BG5 |
| 3 | 0.25 µg 9BG5 |
| MW | molecular weight markers |
| 4 | Empty proteinoid carrier supernatant after encapsulation |
| 5 | Empty proteinoid carrier pellet |
| 6 | mAb containing supernatant after encapsulation |
| 7 | mAb containing protein carrier pellet |

The data indicates that the 9BG5 proteinoid carriers contained about 40% of the mAb in the pellet and the remaining 60% did not incorporate in the proteinoid carriers and was left in the supernatant. The empty proteinoid carriers did not contain antibody in the supernatant or the pellet as was expected.

The relative mobility (molecular weight) of the pure mAb is slightly different than the mAb in the proteinoid carriers. This is most likely due to different salt concentrations in the samples, because the encapsulation process employed 0.8 M salt solution.

EXAMPLE 10

Effect of Additives on Stability of Proteinoid Carriers with Encapsulated Murine mAb 9BG5

Various proteinoid carrier formulations were screened, with or without additives, to determine optimal carrier-forming conditions and concentrations of mAb required for carrer formation.

The mAb 9BG5 preparations used to prepare the encapsulated proteinoid carriers had a protein concentration of approximately 2 mg/ml in phosphate buffered saline.

Final proteinoid concentration was 50 mg/ml and 5% (w/w) gum acacia ("gum") or gelatin ("gel"). All proteinoid carriers were prepared in 0.85 N citric acid. Empty carriers were included for use as controls, and they were prepared in the same manner with the omission of mAb. Duplicate (0.5 ml) aliquots of proteinoid carrier suspension were centrifuged at 5000 RPM. Pellets and supernatants were frozen in dry ice prior to analysis.

Table 7 lists samples that were prepared. Numbers in parenthesis indicate amount of mAb added.

TABLE 7

| SAMPLE | PROTEINOID | ADDITIVE | FINAL PROTEIN (MG/ME) |
|---|---|---|---|
| 1 | 326 | Gum | 0 |
| 3 | 326 | Gel | 0 |
| 5 | 334 | Gum | 0 |
| 7 | 334 | Gel | 0 |
| 9, 10 | 326 | Gum | 0.5 |
| 11, 12 | 326 | Gum | 0.25 |
| 13 | 326 | Gel | 0.25 |
| 15, 16 | 334 | Gum | 0.25 |
| 17, 18 | 334 | Gel | 0.25 |

In order to test resistance to freeze and thawing on the integrity of the proteinoid carriers containing mAb, one of each pair of duplicate pellets were washed by gentle resuspension in 0.25 ml of 0.85 N citric acid. The pellets were then analyzed next to the unwashed pellets to test whether any mAb was lost in the washing.

The samples were analyzed by conventional Western blotting as described in Example 9. Pellets were dissolved in sodium dodecyl sulfate with 0.05 N NaOH and analyzed under reducing conditions (breaks up the mAb into 50 kDa and 25 kDa bands). Aliquots (50 μl) of supernatants were analyzed under non-reducing conditions (expected intact 150 kDa mAb). This was done to determine differentially whether the mAb left behind is denatured or intact.

As can be seen from the X-ray film from the Western Blots (FIG. 7), pellets of samples 9 and 10, and 11 and 12 contain between 5 and 10 μg of mAb. The washed samples did not lose any significant amount of mAb, suggesting that the proteinoid carriers remained intact after freeze-thawing.

The supernatants of samples 9 and 11 had no significant amount of mAb, indicating that unincorporated material was lost during preparation.

Sample 17 had some mAb encapsulated which was lost after washing (see number 18). This sphere preparation was not resistant to freeze-thawing. Additionally, a band at a MW of 150 kDa for sample 17 supernatants indicates that a significant amount of mAb is left behind after proteinoid carrier formation.

Based on these results, it appears that the mAb remains intact and therefore the encapsulating procedure does not degrade it. The empty proteinoid carrier controls did not produce any bands, as expected because they have no mAb.

EXAMPLE 11

Efficacy of Encapsulated Murine IgG Monoclonal Antibody

In this Experiment, a mAb 9BG5 proteinoid carrier preparation and unencapsulated mAb 9BG5 were evaluated in rats. The mAb 9BG5 (1 mg/ml), prepared as described in Example 9, was encapsulated in Glu/Asp/Tyr/Phe proteinoid (1:1:1:1 mole ratio of Glu, Asp,Tyr; and Phe in the reaction mixture) protein carrier formulation with gum arabic. The mAb proteinoid carriers suspension contained 0.25 mg/ml mAb and 50 mg/ml proteinoid in 0.85 N citric acid –0.5% gum. Empty proteinoid carriers were prepared similarly, but did not contain mAb. Since 30% of the mAb was found to be encapsulated, the mAb proteinoid carriers were estimated to contain 0.075 mg/ml mAb and this value was used to determine dosages. The mAb proteinoid carriers were examined microscopically and appear to be a fairly homogeneous preparation.

For animal dosing, appropriate aliquots of proteinoid carriers were centrifuged at 5000 RPM for 15 minutes, and pellets were resuspended in 1.0 ml of 0.85 N citric acid –0.5% gum.

A purified mAb solution (0.95 mg/ml mAb in 0.85 N citric acid-0.5% gum) was used for oral gavage. This solution was prewarmed to 40° C. prior to administration. For IV administration, a purified mAb solution (1 mg/ml mAb in phosphate buffer saline) was used.

The amounts and administration routes employed in the experiment are as follows:

1. Empty proteinoid carriers (no mAb): 1 ml aliquot containing 50 mg empty proteinoid carriers by oral gavage (rats #2312 and 2313).
2. mAb 9BG5 proteinoid carriers: 3.7 mg mAb/kg body weight of rat by oral gavage (rat #2287, 2288, 2290, and 2291).
3. unencapsulated mAb 9GB5: 0.73 mg/kg body weight of rat by intravenous administration (rats #2292, 2293, and 2311).
4. unencapsulated mAb 9BG5: 3.7 mg/kg body weight of rat by oral gavage (rats #2314 and 2315).

Baseline blood samples (1 ml aliquots) were withdrawn from each rat just prior to dosing ("0" time). After dosing, blood samples were drawn at 1 h, 6 h and 24 h. The blood samples were processed immediately and sera were stored frozen at –20° C.

Thawed serum taken from the experimental animals were analyzed by conventional ELISA techniques, in triplicate, using purified reovirus type 3 and $V_L$SH dimeric peptides immobilized in multi-well plates (W. V. Williams et al (1991) *J. Biol. Chem.*, Vol. 266(8), pages 5182–5190). Control plates included wells having no immobilized reovirus and $V_L$SH peptides to which mAb (1 mg/ml) was added. VLSH peptide (W. V. Williams et al. ibid, Table 1) is a synthetic variant of VL peptide, the latter which corresponds to a portion of the light chain variable CDR II region of 87.92.6 antibody. The 87.92.6 antibody displays idiotypic and anti-idiotypic behavior towards reovirus type 3 receptor and mAb 9BG5, respectively (W. V. Williams et al. ibid). The bound protein content of each well were measured by standard protein methods, e.g., Lowry method, and the results for each multi-well plate are shown in FIGS. 8(*a–c*), respectively.

FIGS. 8(*a–c*) illustrate the levels of serum proteins which bound to immobilized reovirus type 3 and $V_L$SH as detected by measurement of protein concentration. These Figures show that the serum levels of bound proteins, after 24 hours post-dosing, were highest for animals orally administered mAb proteinoid carriers and animals administered unencapsulated mAb by the IV route. Lower levels of bound serum proteins were found in animals orally adminstered uncapsulated mAb. Serum taken from the animals receiving empty proteinoid carriers (no mAb) showed non-specific serum IgG protein binding, as expected, under the assay conditions.

Figure 9A:
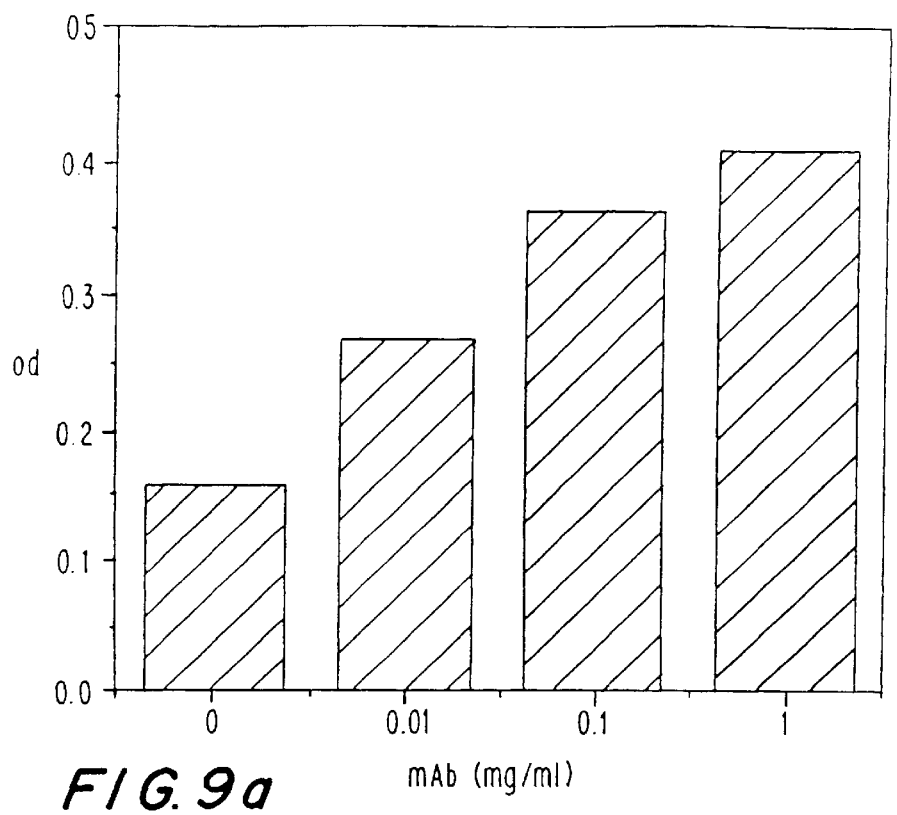
FIG. 9 show mAb binding under conventional ELISA procedures using immobilized reovirus type 3 and $V_L$SH proteins with serial dilutions of purified mAb in 0.85 N citrate –0.5% gum (FIG. 9($a$)) or phosphate buffered saline (FIG. 9($b$)) as described in Example 11.
Figure 9B:
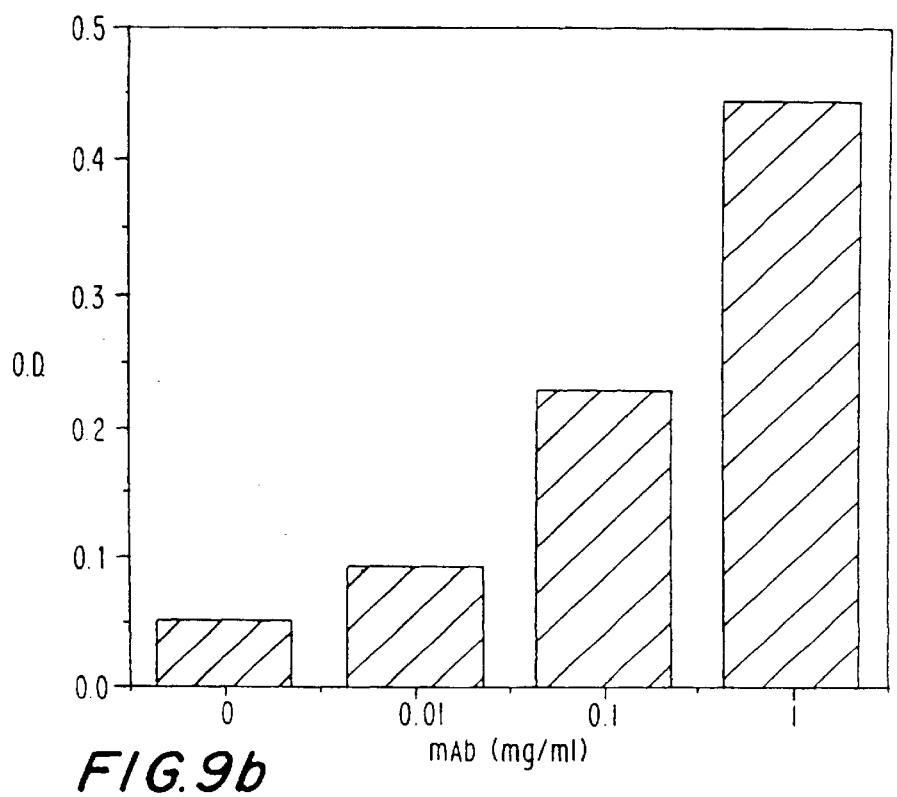

FIG. 9 show mAb binding under conventional ELISA procedures using immobilized reovirus type 3 and $V_L$SH proteins. Serial dilutions of mAb treated with 0.85 N citrate −0.5% gum (FIG. 9(a) or phosphate buffered saline (FIG. 9(b)) were employed. The Figures show that the bound protein levels were higher for mAb in citrate buffer than for mAb in phosphate. Without being bound by any theory of operation for this invention, it is believed that the binding enhancement may be due to changes in the three dimensional conformation resulting from citrate-protein binding.

In summary, serum levels of mAb, as reflected by the absorbance of bound proteins, were greater in animals receiving encapsulated mAb by the oral route or unencapsulated mAb by the IV route, than an animal receiving orally administered unencapsulated mAb.

EXAMPLE 12

Preparation of Proteinoid Carrier Containing Heparin

This Example describes a method for the preparation and cleaning of heparin proteinoid carriers.

PROCEDURE

1. Reagents:
   a. Proteinoid powder prepared as described in Example 1
   b. Heparin
   c. Anhydrous citric acid (USP)
   d. Gum acacia NF
   e. Deionized water
   f. Desiccant
   g. Liquid nitrogen
2. Equipment:
   a. Magnetic stirrer
   b. Buret
   c. Microscope
   d. Clinical centrifuge
   e. Dialysis membrane tubing (Spectrum 6, 10 mm, 50,000 M. W. Cutoff)
   f. pH meter
   g. Lyophilizer (Labconco #75035)
   h. Lyophilizing flasks (150–300 mL)
   i. Rotating shell freezer
   j. Isopropanol/dry ice bath or liquid $N_2$
   k. Mortar and pestle
   l. Storage containers (500 mL)
   m. Eppendorf pipet (0–100 uL)
   n. Plastic closures for dialysis tubing (Spectrum)
   o. 2 mL syringe with 0.45 um Acrodisk
3. Preparation of Solutions:
   a. Proteinoid Solution A* (80 mg/ml):
      Dissolve 160 mg proteinoid in 1 ml of deionized water. Using a 2 ml syringe fitted with a 0.45 um Acrodisk, the proteinoid solution was filtered into a 10 ml test tube and kept at 40° C.
   * or multiples thereof.
   b. Solution B (1.7 N citric acid with 1% gum):
      Dissolve 10 g of gum acacia and 109 g of citric acid in 1 liter of deionized water.
   c. Solution C (Heparin solution):
      Dissolve heparin in Solution B at 150 mg/mL and keep at 40° C.
4. Preparation of Proteinoid carriers:
   a. Add all of solution A to solution C quickly while swirling solution C slowly, by hand, in a 40° C. water bath.
5. Dialysis of Heyarin Proteinoid carriers:
   It has been found the presence of citric acid in the encapsulated proteinoid carriers interferes with a subsequent lyophilization process. Hence, proteinoid carrier encapsulates prepared with citric acid solutions are preferably dialyzed against 5% acetic acid solution for at least two hours with at least four changes of the dialysis solution to remove citric acid by an exchange process. Thus,
   a. Transfer the suspension with a syringe (no needle) to dialysis tubing and seal with plastic closures. Tubing should be no more than 70% full.
   b. Discard any amorphous material sedimented and/or aggregated on the surface.
   c. Dialyze the proteinoid carrier suspension against acetic acid solution (using 20 mL of acetic acid solution per ml of proteinoid carrier suspension) while stirring the acetic acid solution with a magnetic stirrer.
   d. Replace the acetic acid solution every hour. Continue dialyzing for a total of 3 hours.
6. Lyophilization:
   a. Add one part of 50% trehalose (Sigma Chemical Co., St. Louis, Mo., USA) into nine parts of dialyzed proteinoid carrier solution. Flash freeze proteinoid carriers in a freeze-drying flask using the shell freezer adjusted to rotate at ca. 190 rpm and immersed in a liquid nitrogen bath.
   b. Freeze dry for 24 hours or until dry as evidenced by lack of self-cooling.
   c. Record weight of dry proteinoid carriers.
   d. Grind to a fine powder with mortar and pestle.
   e. Transfer proteinoid into an amber container, seal with desiccant, and store at room temperature.
7. Resuspension:
   a. Weigh the lyophilized powder and calculate the amount of proteinoid in the powder.
   b. Add aqueous 0.85 N citric acid into the lyophilized powder at 40° C. The final concentration of proteinoid in solution is 80 mg/ml.

EXAMPLE 13

Preparation of Insulin-containing Proteinoid Carrier

This Example illustrates a method for the preparation of insulin proteinoid carriers.

PROCEDURE

1. Reagents:
   a. Proteinoid powder
   b. Anhydrous citric acid (USP)
   c. Gelatin (USP)
   d. Porcine insulin (Novo Nordisk)
   e. Deionized water (USP)
2. Equipment:
   a. Water bath
   b. 0.2 micron Acrodisk filter
   c. Sterile syringe (10 cc)
   d. Glass or plastic vessel of appropriate volume for desired amount of proteinoid carrier solution.

3. Preparation of Solutions:
   a. 1.7 N citric acid with 5.0% gelatin:
      Dissolve 109 mg anhydrous citric acid and 50 mg gelatin per 1 ml of deionized water at desired volume** and incubate in water bath at 40° C. until gelatin is completely dissolved. This may be prepared and stored at 40° C. for later use.

** Proteinoid and Insulin solutions should each be prepared at one-half the total volume of the final microsphere solution desired.

b. Insulin solution:
      Dissolve 12 mg insulin per 1 ml of 1.7 N citric acid with 5% gelatin at 40° C. at desired volume.
   c. Proteinoid solution:
      Dissolve 100 mg proteinoid per 1 ml deionized water at room temperature and desired volume. Using syringe and 0.2 micron Acrodisk, filter the solution to ensure a clear liquid and incubate in a water bath at 40° C. See Section 5b.

4. Preparation of Proteinoid carriers:
   a. Proteinoid solution and insulin solution are combined at equal volumes sufficient to produce the final desired volume of proteinoid carriers.
   b. Rapidly add the filtered proteinoid solution to the insulin solution at 40° C. while simultaneously and constantly swirling the insulin solution to ensure a thorough mixing.

EXAMPLE 14

Procedure for Preparation of Erythropoietin Containing Proteinoid Carriers

Encapsulation of human erythropoietin (EPO) in proteinoid carriers was performed in the same manner described in Example 13. EPO was obtained from Genetic Institute (Cambridge, Mass., USA, now available from Amgen Corp., Thousand Oaks, Calif., USA). A solution of Gln/Asp/Tyr/Phe (1:1:1:1 mole ratio of Gln, Asp, Tyr, and Phe in the proteinoid reaction mixture) proteinoid and a 150 ug/mL EPO solution in 1.7 N citric acid with 1% gum was used in preparing the EPO-containing proteinoid carrier.

EXAMPLE 15

Evaluation of Erythropoietin-containing Proteinoid Carrier

In this Example, an EPO-containing protein carrier, prepared as described in Example 14, was evaluated in rats. An EPO experimental synopsis is given below.

Rats weighing 150–200 grams are anesthetized with ketamine (8.5 mg/kg) and thorazine 3.75 mg/kg) with intramuscular injection. The rat is then administered either unencapsulated erythropoietin or encapsulated erythropoietin by oral gavage. In brief, an 8 french nelaton catheter is inserted down the esophagus of the rat until the 10 cm mark on the catheter is even with the incisors. The test or control solution is drawn up into a syringe and attached to the catheter. Holding the animal upright, the solution is expressed into the stomach of the rat. The experimental results are summarized in FIGS. 10–12.

| ERYTHROPOIETIN EXPERIMENTAL SYNOPSIS | | | |
|---|---|---|---|
| Batch | Dose | Rats Responding | Comments |
| Control | 15 μg/kg | 0/4 | Fasted 15 hours. |
| 251 < 3K | 15 μg/kg | 0/4 | Access to bedding. |
| 254 < 3K | 15 μg/kg | 2/4 | Gavaged |
| Control | 15 μg/kg | 0/2 | |
| 251 < 3K | 15 μg/kg | 0/2 | Fasted 36 hours. |
| 254 < 3K | 15 μg/kg | 1/4 | 5% sucrose. |
| 270K | 15 μg/kg | 1/3 | No bedding. |
| 270G | 15 μg/kg | 3/3 | Gavaged. |
| Control | 15 μg/kg | 1/5 | Fasted 24 hours. |
| 264CP | 15 μg/kg | 1/4 | Access to bedding. |
| 270G | 15 μg/kg | 1/6 | Gavaged. |
| Control | 10 μg/kg | 0/5 | Fasted 24 hours. |
| 270G | 10 μg/kg | 3*/6 | No bedding. |
| Control | 30 μg/kg | 0/3 | Fasted 24 hours. |
| Control | 60 μg/kg | 1/4 | No bedding. |
| 270G | 30 μg/kg | 1/3 | Direct injection |
| 270G | 60 μg/kg | 1/4 | into the stomach. |
| Control | 50 μg/kg | 0/3 | |
| Control + Pepsin | 50 μg/kg | 0/4 2/4 | Direct injection into the intestine. |
| 270G | 50 μg/kg | | |
| 270G + Pepsin | 50 μg/kg | 0/4 | |
| Control | 100 μg/kg | 1/5 | Multiple Dosing |
| 270G | 100 μg/kg | 1/5 | (5 dosing intervals |
| I.V. | 50 μg/kg | 2/2 | at t 1/2) |
| S.C. | 50 μg/kg | 2/2 | Gavage by stomach tube. |

*Rats were foaming at nostrils.

Figure 10:
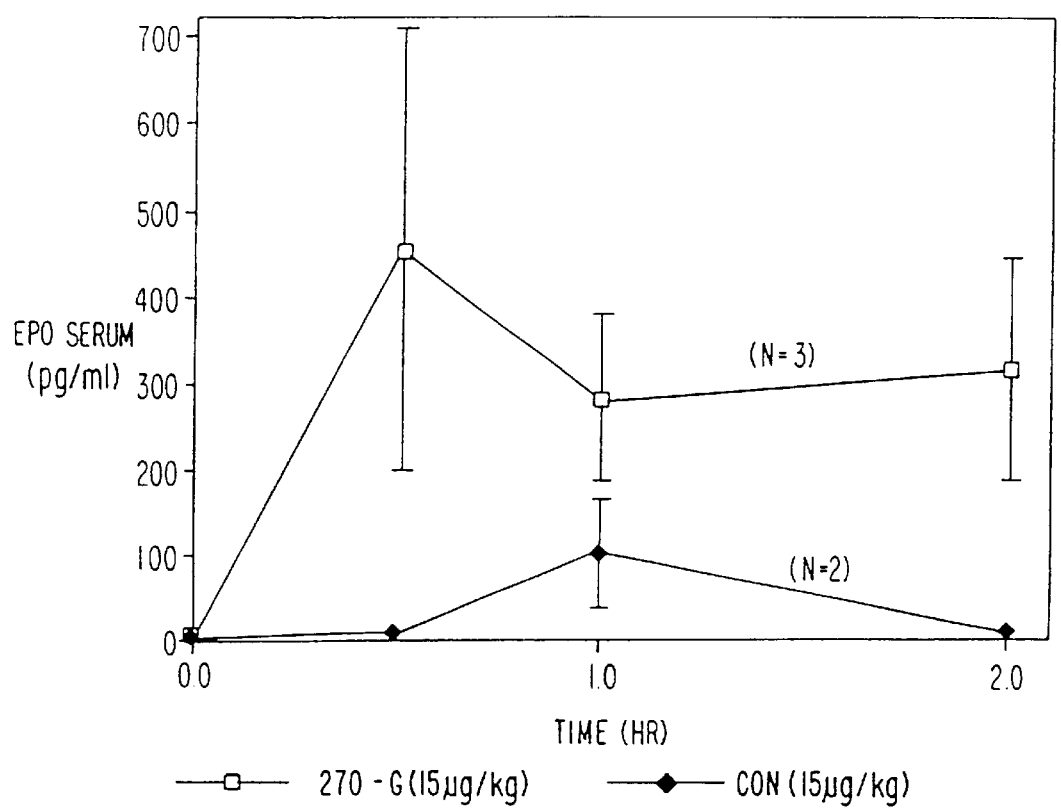
FIG. 10 illustrates levels of erythropoietin (EPO) detected in rat serum taken from rats administered proteinoid carrier encapsulated EPO (15 µg EPO/kg body weight) and encapsulated EPO (15 µg EPO/kg body weight) as described in Example 15.

FIG. 10 illustrates levels of erythropoietin (EPO) detected in rat serum taken from rats administered Gln/Asp/Tyr/Phe proteinoid carrier encapsulated EPO (15 μg EPO/kg body weight) and encapsulated EPO (15 μg EPO/kg body weight) at t=0.5, 1, and 2 hours. Serum erythropoietin levels were determined over time with an erythropoietin enzyme immunoassay kit (Amgen, Thousand Oaks, Calif., USA). The results show that EPO serum levels in rats administered erythropoietin proteinoid carriers were relatively higher at all time points compared to rats (control) which received unencapsulated material. At t=2 hours, the EPO levels remained at approximately 300 pg/mL serum in rats administered erythropoietin proteinoid carriers while the control rats had undetectable EPO levels.

Figure 11:
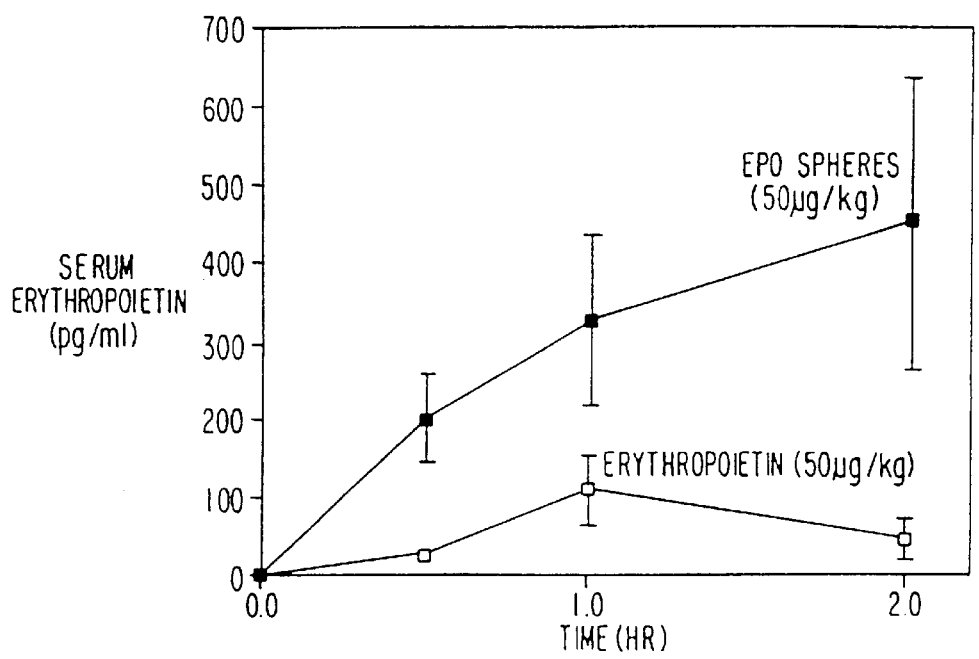
FIG. 11 illustrates EPO serum levels in rats that were administered either erythropoietin (50 µg/kg) or encapsulated erythropoietin (50 µg/kg) directly into the proximal duodenum as described in Example 15. Serum erythropoietin levels were determined over time with a erythropoietin enzyme immunoassay kit.

FIG. 11 illustrates EPO serum levels in rats that were administered either erythropoietin (50 μg/kg) or Gln/Asp/Tyr/Phe proteinoid (1:1:1:1 mole ratio of Gln, Asp, Tyr, and Phe in the reaction mixture) proteinoid carrier encapsulated erythropoietin (50 ug/kg) directly into the proximal duodenum. Serum erythropoietin levels were determined over time with the aforementioned erythropoietin enzyme immunoassay kit. The results show that EPO serum levels in rats administered erythropoietin proteinoid carriers steadily increased at a rate of approximately 50 pg/mL per hour over a range of two hours. In contrast, rats (control) which received unencapsulated EPO had EPO levels peaked at 100 pg/mL at 1 hour following administration and steadily decreased to about 50 pg/mL at the end of 2 hours.

Figure 12:
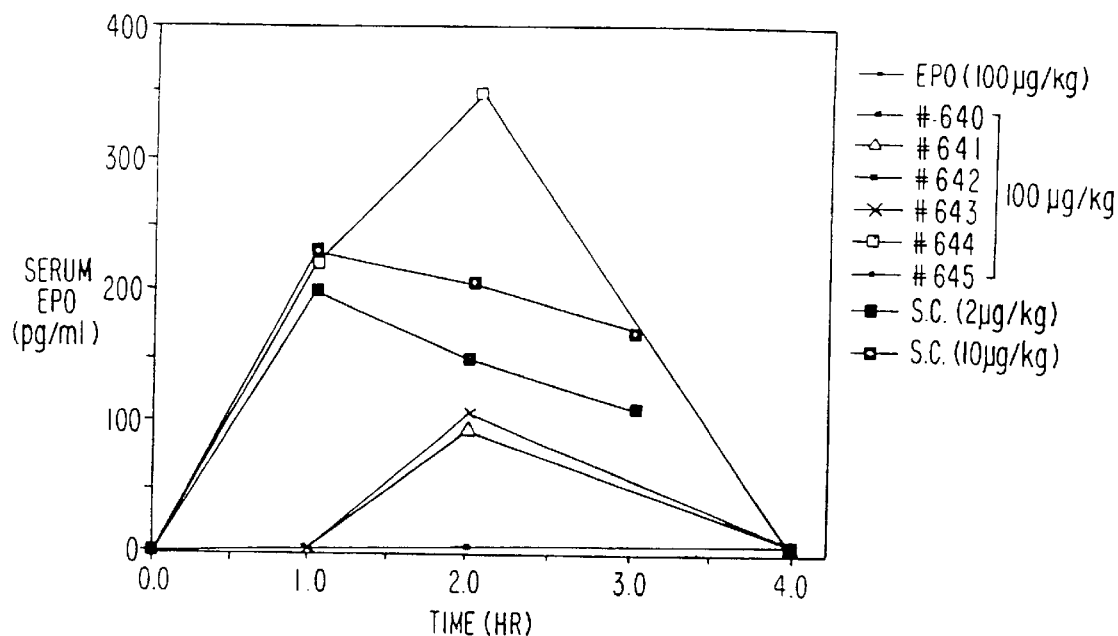
FIG. 12 illustrates EPO serum levels in rats who were orally gavaged with either encapsulated or unencapsulated erythropoietin (100 µg/kg) or received a subcutaneous injection of either 2 µg/kg or 10 µg/kg as described in Example 15. Serum erythropoietin levels were determined over time with an erythropoietin enzyme immunoassay kit.

FIG. 12 illustrates EPO serum levels in rats who were orally gavaged with either Gln/Asp/Tyr/Phe proteinoid (1:1:1:1 mole ratio of Gln, Asp,Tyr, and Phe in the reaction mixture) proteinoid carrier encapsulated or unencapsulated erythropoietin (100 μg/kg); or received a subcutaneous injection of either 2 μg/kg or 10 μg/kg. Serum erythropoietin levels were determined over time with the aforementioned erythropoietin enzyme immunoassay kit. The results show that EPO serum levels in rats (#640–645) orally administered erythropoietin proteinoid carriers were relatively higher up to t=2 hours, compared to rats (EPO) which received unencapsulated material.

The results obtained in this Example provide evidence that proteinoid encapsulation markedly improved the oral bioavailability of EPO.

EXAMPLE 16

Preparation of Calcitonin-containing Proteinoid Carrier

Encapsulation of salmon calcitonin in proteinoid proteinoid carriers was performed in the same manner described in Example 13. Calcitonin, a peptide hormone which acts predominantly on bone to lower serum calcium concentration, was obtained from Sandoz (Basil, Switzerland). Calcitonin proteinoid carriers were prepared by mixing a 1:1 volume ratio of a 100 mg/ml aqueous solution of Gln/Asp/Tyr/Phe proteinoid (1:1:1:1 mole ratio of Gln, Asp, Tyr, and Phe used in the proteinoid reaction mixture) and a 150 µg/mL calcitonin solution in 1.7 N citric acid solution with 1% gum acacia, as described in Example 13. The efficiency of calcitonin encapsulation was approximately 40%. Calcitonin concentration was determined directly by HPLC after dissolving the calcitonin proteinoid carriers in 60% aqueous acetonitrile.

EXAMPLE 17

Evaluation of Calcitonin-containing Proteinoid Carriers in Monkeys

In this Example, the calcitonin proteinoid carriers, prepared as described in Example 16, were evaluated in cynomolgus monkeys. Male cynomolgus monkeys weighing 4–5 kg were fasted overnight, anesthetized (approximately 10 mg/kg ketamine HCl) and placed into a primate restraint chair for dosing and blood sampling. A single oral dose of calcitonin proteinoid carriers (0.25 mg/kg body weight) was administered to each of four monkeys by nasogastric gavage. The dosage was based on the body weight taken on the morning of dosing. Blood samples were collected from saphenous vein catheters at hourly intervals, starting at t=0 prior to administration of the proteinoid carriers, and hourly, from 1 to 7 hours post-dose for serum calcium determination. The hypocalcemic response following oral calcitonin administration was used as an index of pharmacological response. Serum calcium concentrations were quantitated by a conventional O-cresolphthalein complexone method.

Figure 13:
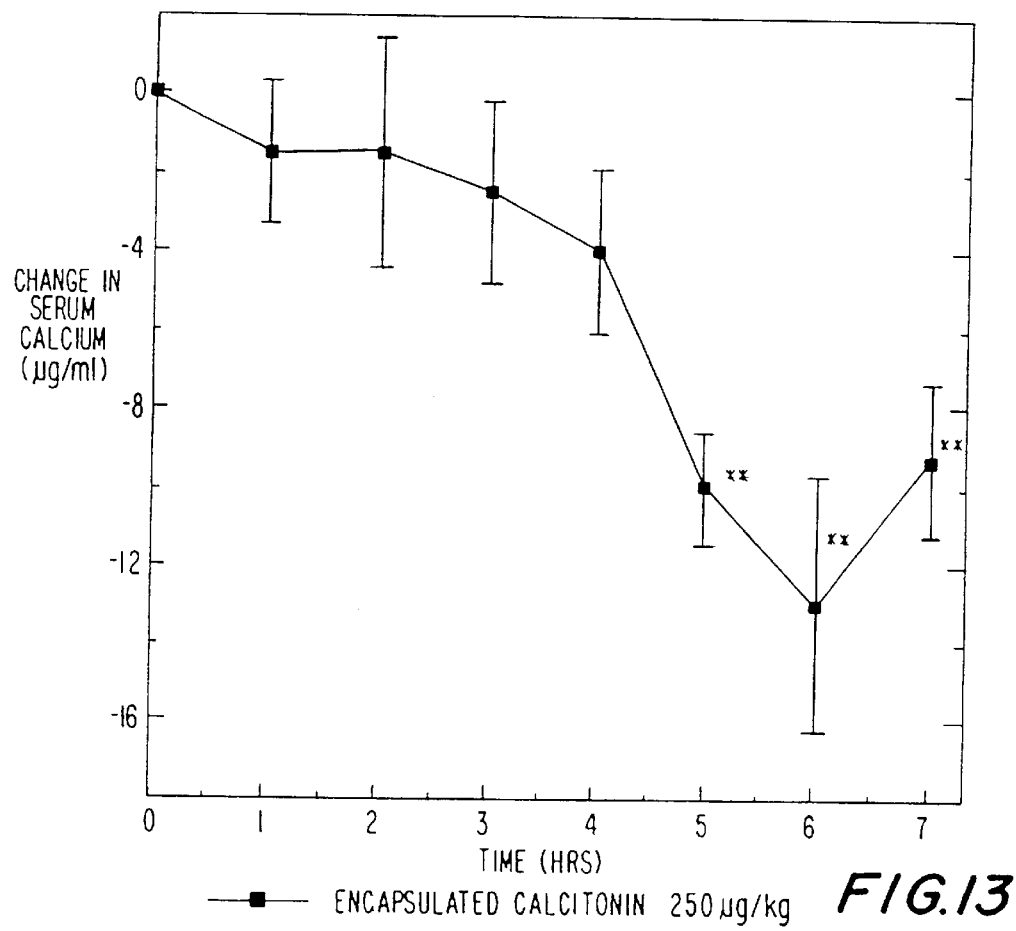
FIG. 13 illustrates serum calcium changes after oral administration of salmon calcitonin proteinoid carriers (0.25 mg calcitonin/kg body weight) in cynomolgus monkeys as described in Example 17. The results are expressed as absolute change in serum calcium from baseline values. The data represents means +/–SEM. ** Serum calcium levels significally different from baseline values.

FIG. 13 demonstrates the response obtained in cynomolgus monkeys following naso-gastric gavage of microencapsulated calcitonin. Significant changes from baseline serum calcium concentration were observed. Six hours following dosing, serum calcium concentrations decreased by 13 µg/ml. A significant pharmacological response was still apparent seven hours. after the administration of calcitonin proteinoid carriers.

EXAMPLE 18

Evaluation of Calcitonin-containing Proteinoid Carriers in Rats

In this Example, the calcitonin proteinoid carriers prepared in accordance with Example 16 are evaluated in fasted male Spraque Dawley rats weighing 100–150 g. Calcitonin proteinoid carriers and calcitonin were administered by either oral gavage or intraduodenal injection. The rats are divided into the following groups:

1. calcitonin proteinoid carriers: 60 ug calcitonin/kg body weight by oral gavage (3 rats);
2. calcitonin proteinoid carriers: 3 ug calcitonin/kg body weight by intraduodenal gavage (3 rats);
3. calcitonin: 60 ug calcitonin/kg body weight by oral gavage (3 rats) (Control).
4. calcitonin: 3 ug calcitonin/kg body weight by intraduodenal gavage (3 rats) (Control).

Oral gavage dosing of rats is performed. Calcitonin proteinoid carriers are prepared immediately prior to dosing and Groups 1 and 2 each receive an appropriate dosage of the proteinoid carrier suspension. Groups 3 and 4 receive the unencapsulated calcitonin (no proteinoid carriers). Approximately 0.5 ml of blood is serially withdrawn from the tail artery of each rat just prior to dosing ("0" time) and 1 h, 2 h and 3 h post-dosing. Serum from the blood samples are stored at −20° C. for serum calcium concentration determination.

Figure 14:
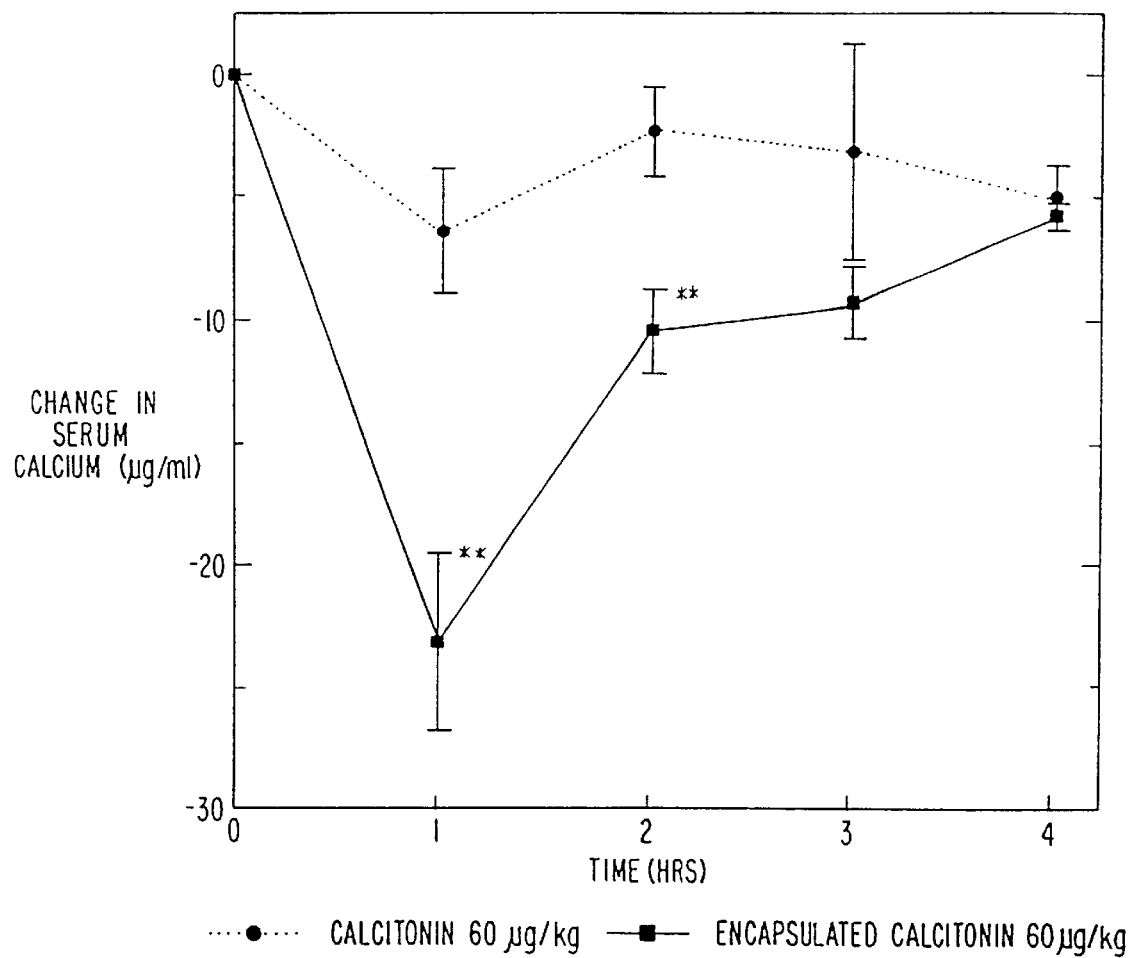
FIG. 14 illustrates serum calcium changes following oral administration of salmon calcitonin proteinoid carriers (0.60 mg/kg body weight) in rats as described in Example 18. The results are expressed as absolute change in serum calcium from baseline values. The data represents means +/–SEM. ** Serum calcium levels significantly different compared to the control group at the corresponding time point.

FIG. 14 is the serum concentration-time curve for orally administered microencapsulated calcitonin and unencapsulated calcitohin in rats. Experimental results in rats demonstrate a significant increase in pharmacological response (i.e., decreasing serum calcium levels) when proteinoid encapsulated calcitonin is compared to the unencapsulated vehicle control group. One hour after dosing, serum calcium concentrations decreased 23 µg/ml in the rats receiving encapsulated calcitonin compared to a decrease of only 6.5 µg/ml in the control group. Furthermore, the responses were dose-dependent (data not shown).

Figure 15:
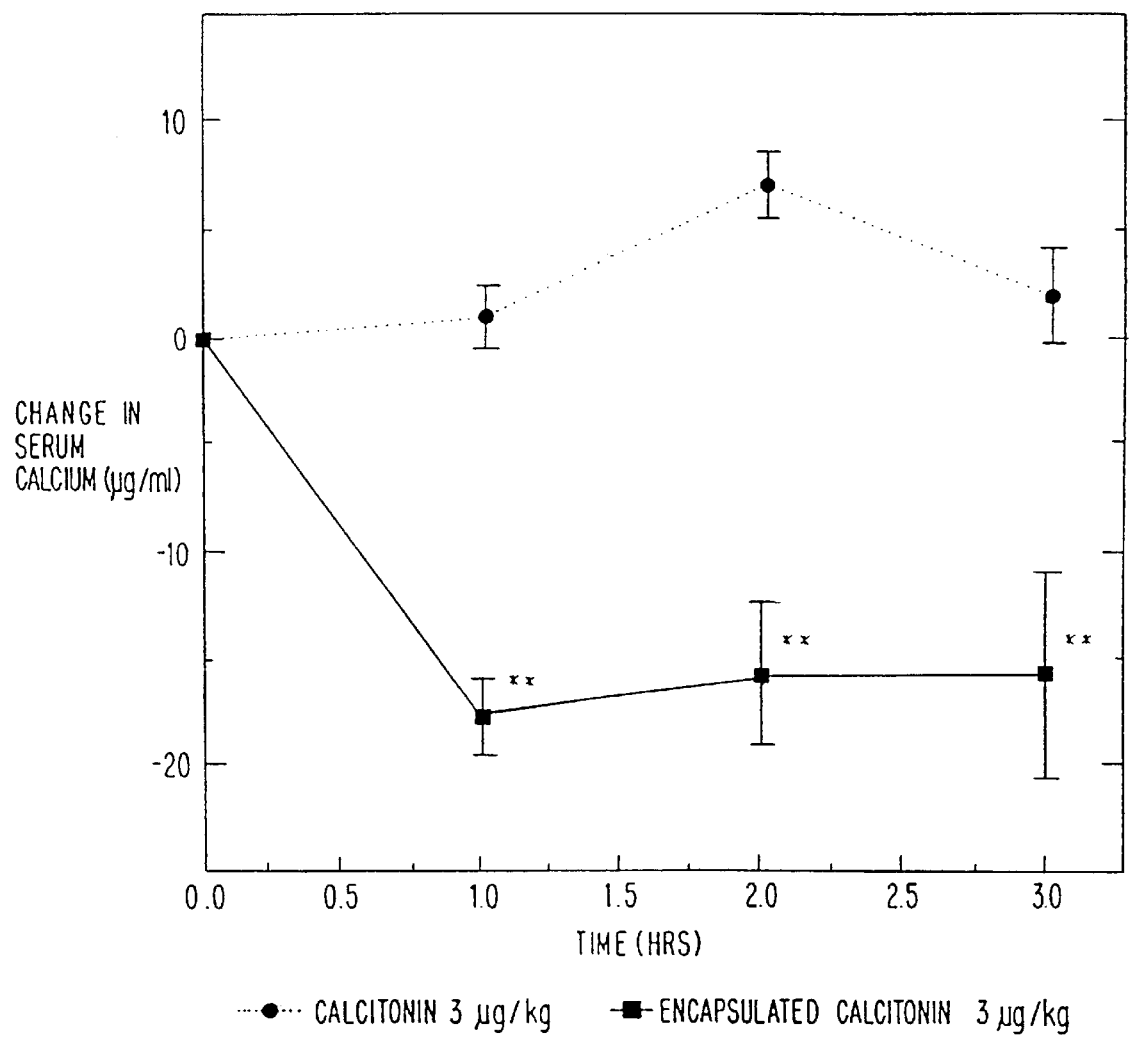
FIG. 15 illustrates serum calcium changes after intraduodenal administration of salmon calcitonin or calcitonin proteinoid carriers (3 ug/kg body weight) in rats as described in Example 18. The results are expressed as absolute change in serum calcium from baseline values. The data represents means +/–SEM. ** Significantly different from the unencapsulated control group at the indicated time points.

The results of intraduodenal injection of encapsulated or unencapsulated calcitonin in rats is shown in FIG. 15. The results demonstrate a time-dependent decrease in serum calcium levels for the encapsulated preparation. The control group showed no response. One hour after intraduodenal administration, serum calcium levels in the calcitonin proteinoid carrier group decreased by 18 µg/ml, whereas unencapsulated calcitonin was unchanged. These results indicate that transmembrane transport of calcitonin is enhanced by proteinoid encapsulation.

The results obtained in this Example and in Example 17 provide evidence that proteinoid encapsulation markedly improves the oral bioavailability of calcitonin. The data also indicate that the oral drug delivery system is not species-dependent.

EXAMPLE 19

Preparation and Evaluation of Factor IX-containing Proteinoid Carrier

Factor IX is a vitamin K-dependent blood coagulation proenzyme, MK 56 kD. Factor IX deficiency, known as hemophilia B, occurs in approximately 1 out of every 25,000 males. To date, treatment of this disorder is accomplished by intravenous administration of Factor IX, although a recent report details efforts to supplement by subcutaneous injection (Thompson (1986) Blood, Vol. 67(3), pages 565–572).

Encapsulation of Factor IX (FIX) in proteinoid carriers was performed, following the procedure described in Example 13, by mixing (1:1 v/v) 100 mg/mL of Glu/Asp/Tyr/Phe proteinoid (1:1:1:1 mole ratio of Glu, Asp, Tyr, and Phe used in the proteinoid reaction mixture) in deionized water and an aqueous solution of EIX. Two proteinoid carrier suspensions were prepared and evaluated in vivo separately as described in Examples 20 and 21

FIX proteinoid carrier suspension A contained 50 mg/ml of proteinoid and 500 U/ml FIX (FIX is available from the American Red Cross, Rockville, Md., USA) solution containing 4% acetic acid, 2% gum acacia, 0.2% PEG 14 (available from Union Carbide, Danbury, Conn., USA), 14 mM $CaCl_2$, final pH 3.81.

The second suspension, FIX proteinoid carrier suspension B, contained 50 mg/ml proteinoid and 116 U/ml FIX solution containing 3.8% acetic acid, 1.5% gum acacia, 0.15% PEG 14, 11 mM $CaCl_2$, final pH 4.58.

The stability of FIX proteinoid carrier preparations was assessed over a short time course in vitro. The protein carriers encapsulating FIX were examined by optical microscopy and laser light scattering. Aliquots of proteinoid carrier suspension were withdrawn every 30 minutes for 1.5 hours, FIX proteinoid carriers were isolated by centrifugation at 4500×g and dissolved in activated partial thromboplastin time (APTT) assay buffer (0.05M histidine-0.01M NaCl-0.1% bovine serum albumin-0.01% TWEEN-40, pH 7.47) to release soluble FIX and proteinoid. Quantitation of FIX activity by APTT employed both FIX standards (0.025, 0.05, and 0.1 U/ml) and "empty" proteinoid carrier suspension as control. APTT assay kits are commercially available, e.g. Sigma Diagnostics (St. Louis, Mo., USA).

Based on the above analysis, it was determined that FIX proteinoid carriers of greater stability are obtained by encapsulating FIX at a higher pH, e.g., pH 4.9. Furthermore, the efficiency of encapsulation is approximately 20% of available FIX units and activity levels remain constant for at least 1.5 hours when FIX proteinoid carrier pellets are stored at about 4° C.

EXAMPLE 20

Evaluation of FIX-containing Proteinoid Carriers (A) in Rats

In this Example, FIX proteinoid carrier suspension A, prepared as described in Example 19, were evaluated in male Sprague Dawley rats (ave. weight 300 g). Appropriate aliquots of suspension were centrifuged at 4500×g to pellet the FIX protein carriers, which were subsequently resuspended in the same buffer for animal dosing. The rats are divided into two groups as follows:

1. Oral FIX proteinoid carriers (FIX sph PO): 2709 U FIX/kg body weight by intragastric gavage (4 rats);
2. Intravenous FIX (no proteinoid carriers) (FIX IV): 200 U/kg body weight by intravenous injection. 32 rats received 0.7 ml FIX in 0.11 NaCl-0.02 M sodium citrate, pH 6.85 by tail vein injection.

The FIX proteinoid carrier suspension and solution are prepared immediately prior to dosing. One ml of blood was withdrawn from each rat just prior to dosing ("0" time) and 1 h, 2 h and 4 h (post-dosing)., a citrate anticoagulant was added to the blood, and plasma from the blood samples were stored at −70° C.

Figure 16:
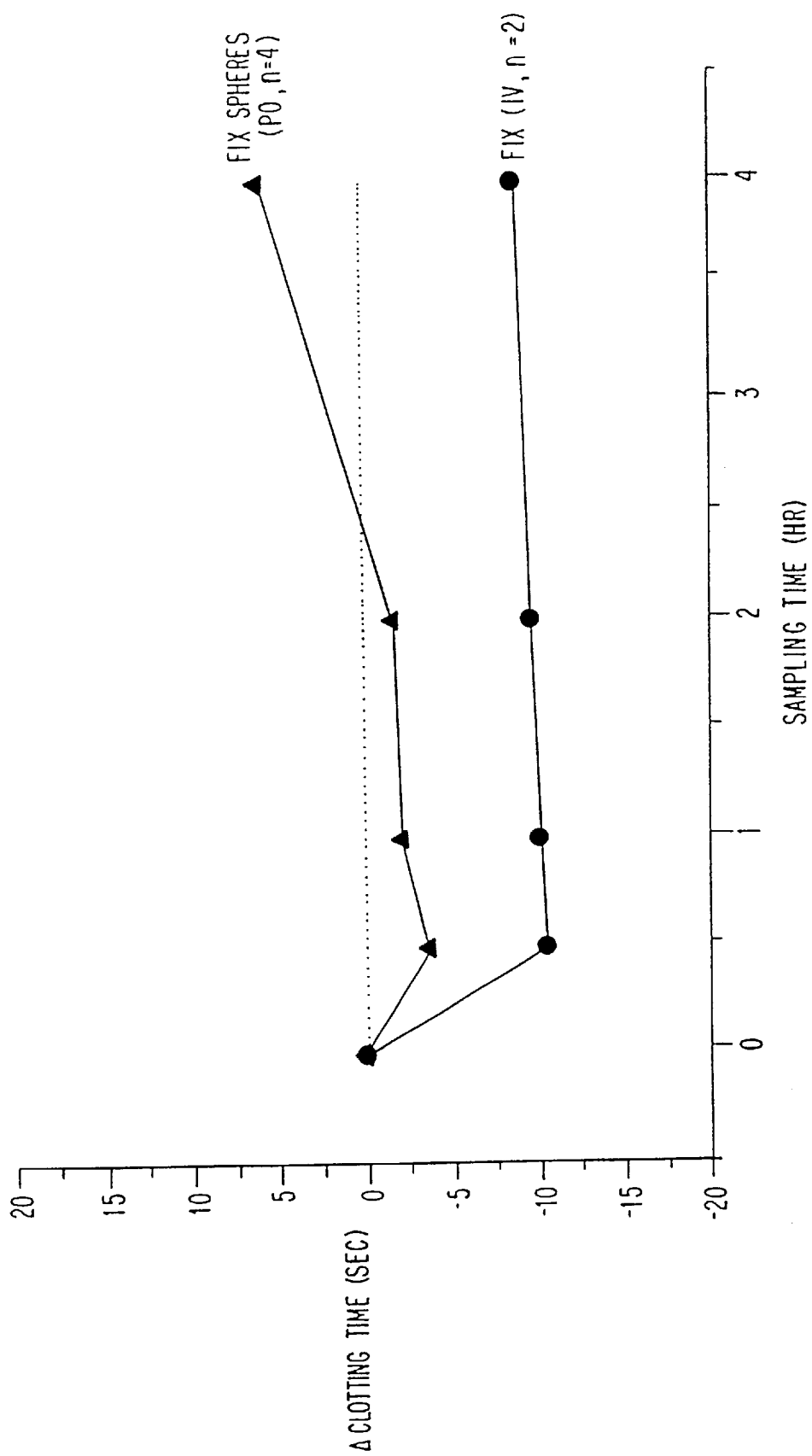
FIG. 16 illustrates clotting times after oral administration of proteinoid carrier encapsulated Factor IX (FIX sph PO) and IV administration of FIX solution (FIX IV) as described in Example 20.

Plasma samples were assayed by a modified APTT assay using FIX coagulated deficient plasma (assay kit is available from Ortho Diagnosis (Raritan, N.J., USA). Changes in clotting times were calculated by subtracting individual baseline (0 hr) values from subsequent clotting time values. The data shown in FIG. 16 are the mean values for a given group. Values below baseline indicate the presence of exogenous FIX.

As shown in FIG. 16, significant amounts of FIX was delivered to blood via oral administration of FIX proteinoid carriers. The relative plasma level is lower in the FIX proteinoid carriers group, however the dimunition in clotting time at 0.5, 1.0 and 2.0 hours is notable. This is achieved by oral dosing with approximately 14 times the IV dose. Moreover, these results are particularly interesting since Factor IX is an acid labile protein whose half-life is approximately less than one hour at 37° C. at pH 5.0. The FIX proteinoid carriers in this experiment were at pH 3.81 and encapsulated 14.8% of the available FIX units during preparation. The results support that FIX proteinoid carriers remain viable in the GI tract to facilitate delivery.

EXAMPLE 21

Evaluation of FIX-containing Proteinoid Carriers (B) in Rats

In this Example, FIX proteinoid carrier suspension B, prepared as described in Example 19, were evaluated in male Sprague Dawley rats (ave. weight 300 g). Resuspended FIX proteinoid carriers were prepared as described in Example 20. The rats are divided into two groups as follows:

1. Oral FIX proteinoid carriers (FIX sph PO): 1006 U FIX/kg body weight by intragastric gavage (5 rats).
2. Intravenous FIX (no proteinoid carriers) (FIX IV): 185 U/kg body weight by intravenous injection. 3 rats received 0.3 ml FIX in 0.11 NaCl-0.02 M sodium citrate, pH 6.85 by tail vein injection.
3. Oral FIX (no proteinoid carriers) (FIX unencap PO): 2760 U FIX/kg body weight by intragastric gavage. 4 rats received 1.0 ml of FIX in saline solution containing 3.86 acetic acid, pH 6.85.

Figure 17:
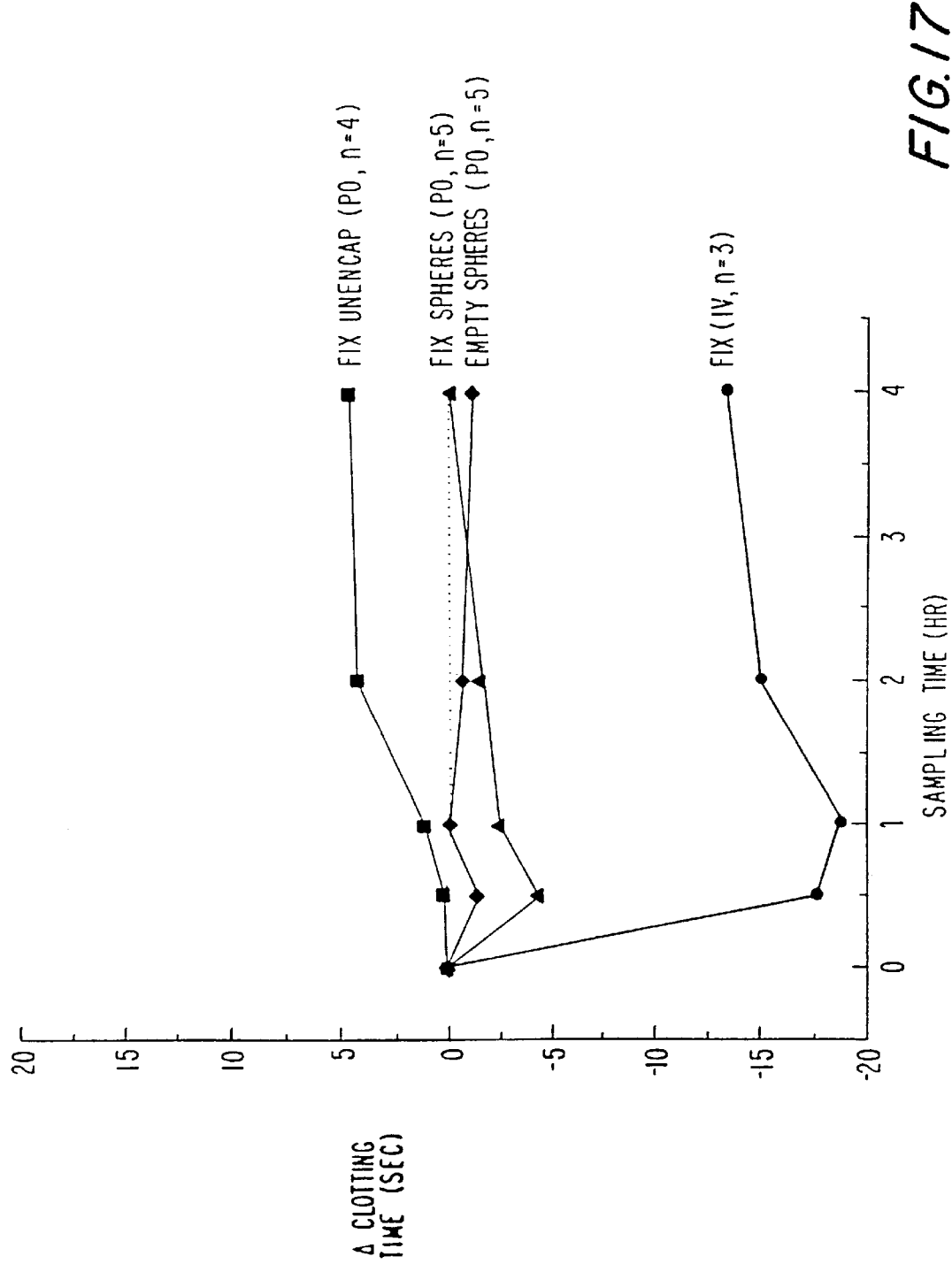
FIG. 17 illustrates clotting times after oral administration of proteinoid carrier encapsulated Factor IX (FIX sph PO) and FIX solution (FIX unencap PO) or IV administration of FIX solution (FIX IV) as described in Example 21.

The FIX proteinoid carrier suspension and solutions were prepared immediately prior to dosing. Plasma samples were obtained and assayed as described in Example 20. Changes in clotting times were calculated by subtracting individual baseline (0 hr) values from subsequent clotting time values. The data shown in FIG. 17 are the mean values for a given group. Values below baseline indicate the presence of exogenous FIX. The FIX proteinoid carriers, prepared at pH 4.58, encapsulated 23.1% of the FIX units.

As shown in FIG. 17, at oral dose levels of only 5 times that of the IV dose, significant oral delivery was observed. In addition, native FIX (pH 6.85) dosed at 15 times the IV dose level resulted in no detectable levels of exogenous FIX in the plasma.

Thus, the results shown in this Example and in Example 20 support that oral delivery of FIX can be accomplished via the use of FIX proteinoid carriers. These proteinoid carriers appear to adequately protect FIX during transit through the GI tract and deliver FIX to the blood stream.

EXAMPLE 22

Preparation of alpha-Interferon (IFN)-containing Proteinoid Carrier

In this Example, a study was undertaken to evaluate the protective capability of proteinoid carriers on enzymatic degradation under simulated gastrointestinal conditions. The in vitro stability of IFN in proteinoid carriers was examined in simulated gastric fluid (SGF) containing pepsin in 0.08 N HCl and simulated intestinal fluid (SIF) containing pancreatin in phosphate buffer. The reagents and stability assay procedure are described in the "United States Pharmacopocia" (Vol. XXII, 1990, pages 1788 and 1789).

Preparation of IFN-containing Proteinoid Carriers

Encapsulation of IFN in proteinoid carriers was performed in the same manner described in Example 13.

Alpha-IFN is available from a number of commercial sources. One commercial IFN product includes Roferon-A (Hoffman LaRoche). IFN proteinoid carriers were prepared with an aqueous solution of Glu/Asp/Tyr/Phe proteinoid (1:1:1:1 mole ratio of Glu, Asp, Tyr and Phe used in the proteinoid reaction mixture), and an IFN solution containing 1.7 N citric acid solution with 5% gelatin. The IFN proteinoid carrier suspension contained 80 mg/ml proteinoid, 600 ug/ml IFN, 0.6N citric acid, and 2.5% gelatin, pH 3.0.

Stability of IFN Proteinoid Carriers in SGF

SGF (2 ml) was added into 1 ml of IFN proteinoid proteinoid carrier suspension. The solution was incubated at 40° C. with shaking, and aliquots were taken serially after SGF addition as described in the "U.S. Pharmacocopia" (ibid). An equal volume of stopper solution (pepstatin A in phosphate buffer, was added to each aliquot immediately after sampling to stop the enzymatic degradation and to open the proteinoid carriers. The IFN concentration in all samples was then determined by HPLC. As a comparison, the stability of IFN alone in SGF was evaluated. The experiment were performed as described above, without the proteinoid carriers. As another control, the stability of IFN proteinoid carriers was evaluated in 0.08 N HCl.

Stability of IFN-containing Proteinoid Carriers in SIF

SIF (2 ml) was added into 1 ml IFN proteinoid carriers. The solution was incubated at 40° C. with shaking and samples were taken serially as described in the "United States Pharmacocopia" (ibid). An equal volume of stopper solution (aprotinin and trypsin/chymotrypsin inhibitor in phosphate buffer) was added to each aliquot immediately after sampling to stop the enzymatic degradation. The IFN concentration was analyzed by HPLC.

To study the study the stability of IFN alone in SIF, 600 ug of IFN was dissolved in 0.85 N citric acid or 0.01 M phosphate buffer. SIF (2 ml) was added to 1 ml IFN solution. The solution was sampled and analyzed as described above.

Results and Discussion
(a) Protective Effects of Proteinoid Carriers in SGF

Figure 18:
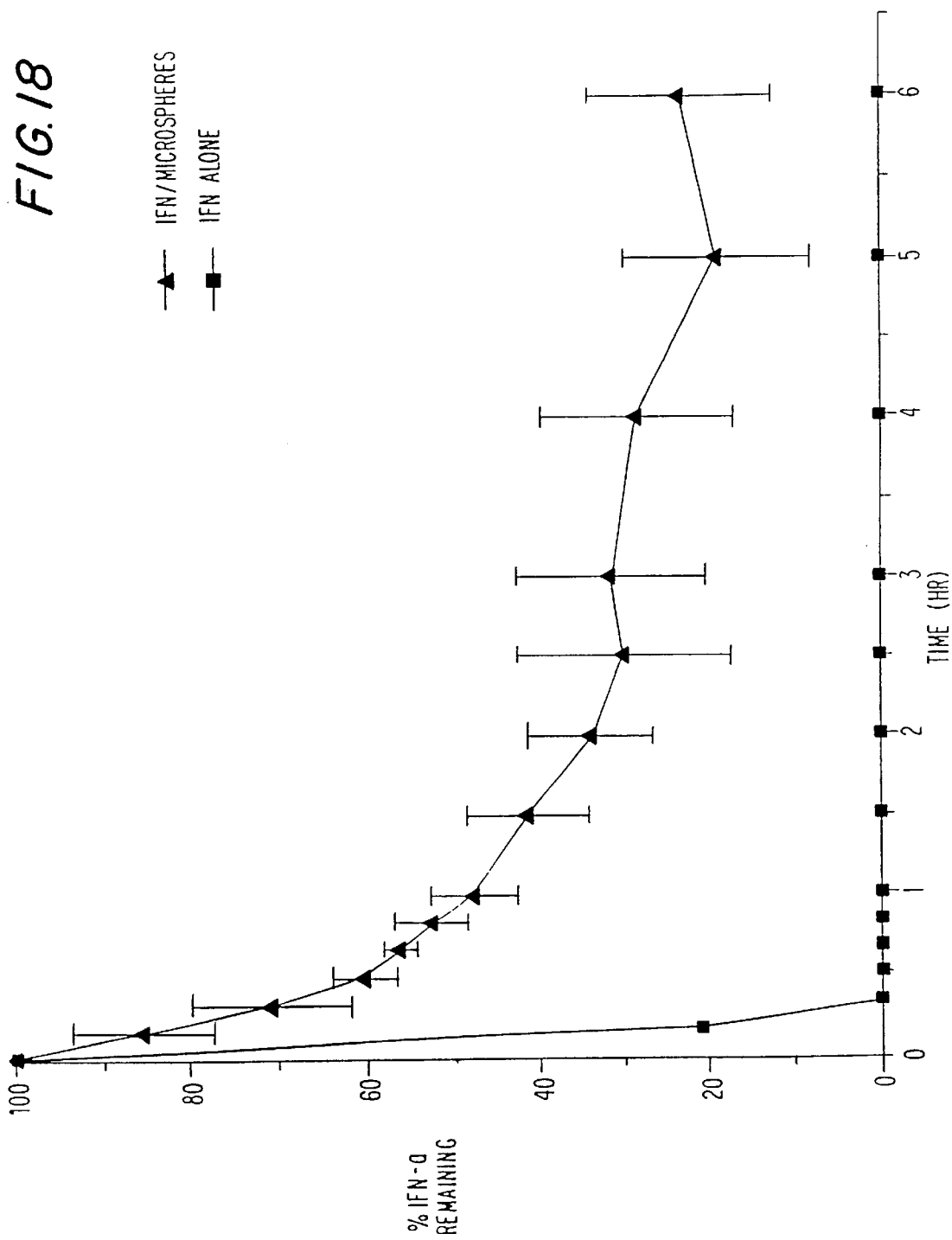
FIG. 18 illustrates the percentage of intact alpha-interferon (IFN) remaining after incubating IFN and IFN proteinoid carriers in simulated gastric fluid (SGF).

As shown in FIG. 18, after 1 hour of SGF incubation, approximately 50% of IFN remained intact. After incubation in SGF for 6 hours, approximately 20% of IFN was not degraded. As expected, IFN alone (in the absence of proteinoid carriers), was found to be completely destroyed by pepsin in SGF within 20 minutes.

Figure 19:
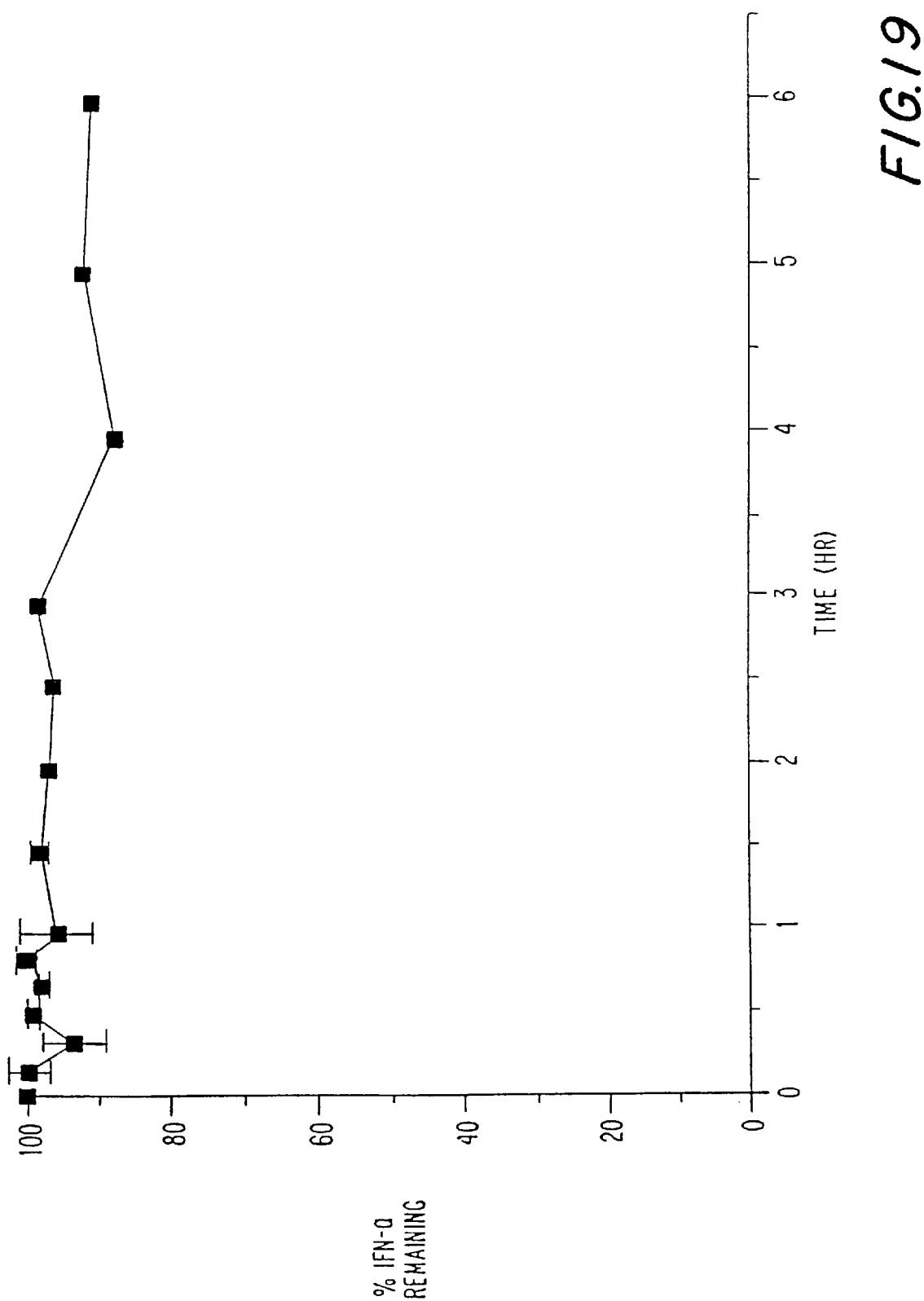
FIG. 19 illustrates the percentage of intact IFN remaining after incubating IFN and IFN proteinoid carriers in 0.08N HCl.

Another control was performed using IFN alone in 0.08 N HCl. IFN alone was stable in SGF without pepsin (0.08 HCl). There was only a slight decrease after 2 hour incubation. This suggests that IFN was rather stable in HCl at pH 1.2 up to six hours (FIG. 19).

Figure 20:
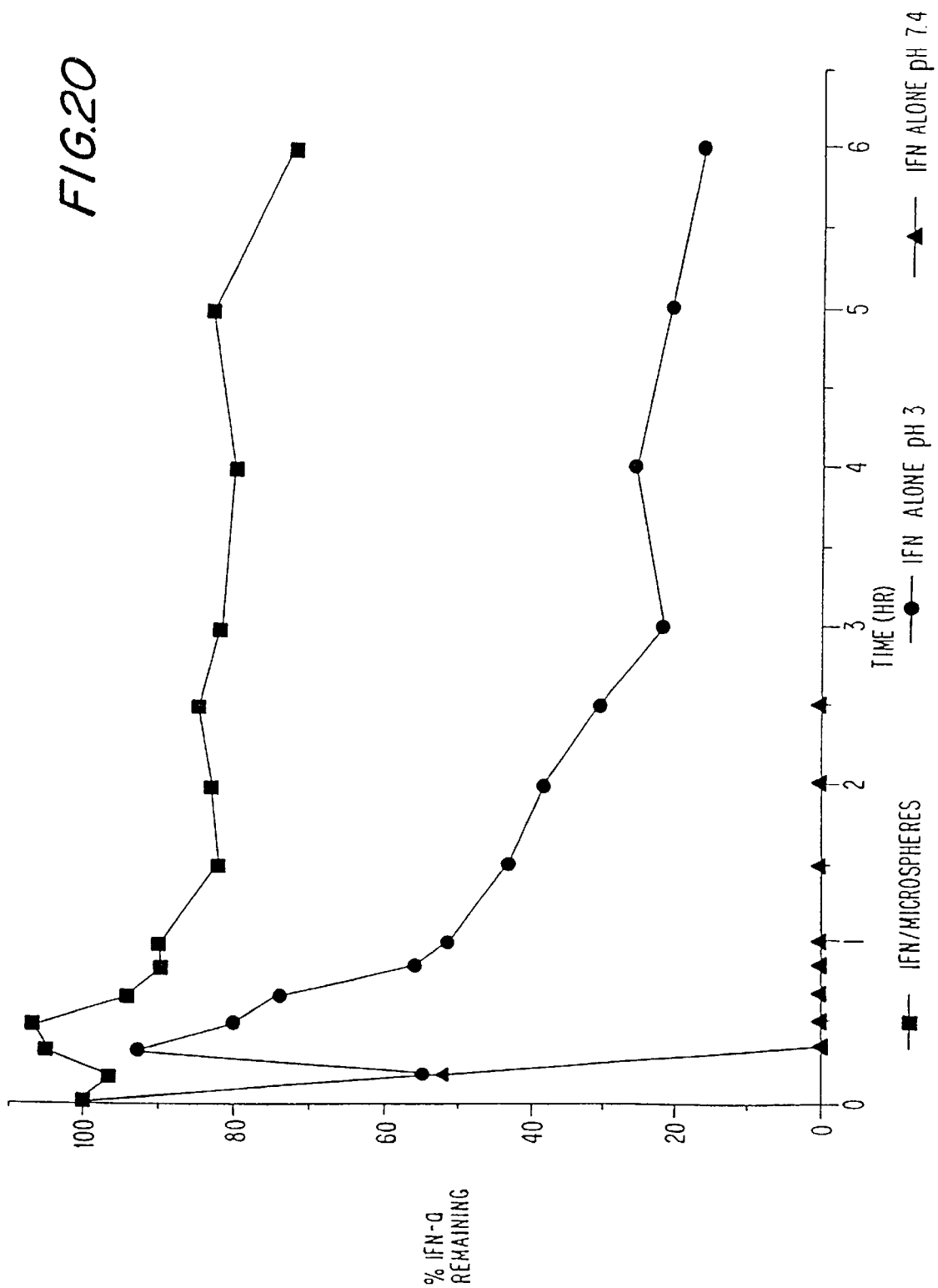
FIG. 20 illustrates the percentage of intact IFN remaining after incubating IFN and IFN proteinoid carriers in simulated intestinal fluid (SIF).

The results suggest that proteinoid carriers can retard IFN from pepsin digestion, while IFN alone cannot survive in the stomach for more than 20 minutes. These observations demonstrate the protective ability of proteinoid carriers on enzymatic digestion of protein drugs in the stomach.
(b) Protective Effects of Proteinoid Carriers in SIF As shown in FIG. 20, IFN proteinoid carriers were much more stable than IFN alone (in the absence of proteinoid) in SIF. IFN alone at pH 7.4 was completely degraded within 10 minutes when incubated with SIF. However, approximately 70% of the IFN/proteinoid carriers survived after 6 hours in SIF, indicating that considerable stability is provided by the proteinoid proteinoid carrier.

IFN alone was slightly more stable in SIF at pH 3 than at pH 7.4. After 6 hr incubation in SIF at pH 3, there was approximately 10% of the IFN remaining. The stability of IFN in SIF at pH 3 is attributed to the low pH, which appears to suppress enzymatic activity of the intestinal proteases.

EXAMPLE 23

Evaluation of Heparin-containing Proteinoid Carriers in Rats

In this Example, a study was undertaken to ascertain whether proteinoid carriers are required for protective capability or whether (1) proteinoids (soluble proteinoids—not in carrier form) may be used and whether (2) alternative methods of carrier, loading, such as incubating the therapeutic compound with preformed proteinoid carriers, are useful.

Preparation of Heparin-containing Proteinoid Carriers

Encapsulation of heparin in proteinoid carriers was performed in the same manner described in Example 12. Heparin (USP grade) was used and this material is available from a variety of commercial sources including Eli Lilly (Indianapolis, USA). Heparin proteinoid carriers were prepared, following the procedure of Example 12, using a 1:1 volume ratio of 150 mg/ml of Glu/Asp/Tyr/Phe/Orn$_{0.5}$ (1:1:1:1:0.5 mole ratio of Glu, Asp, Tyr, Phe, and Orn used in the proteinoid reaction mixture) proteinoid in deionized water, and an 20 mg/mL aqueous heparin solution containing 1.7 N citric acid solution and 0.5% gum acacia. The heparin proteipoid carrier suspension was dialyzed in acetic acid solution as described in Example 12. Heparin proteinoid carriers were then centrifuged at 4800×g (15 minutes) and total heparin was measured by assaying the pellet and the supernatant with a modification of the Azure A method (Gundry et al. *Amer. J. of Surgery* (1984) Vol. 148, pages 191–194). Proteinoid was assayed by dissolving the proteinoid carriers with 0.1 N NaOH and measuring absorbance at 294 nm.

Preparation of Heparin-spiked Empty Proteinoid Carriers

Empty proteinoid carriers were prepared following the same procedure described above for the heparin proteinoid carriers, with the modification being that no heparin was present. The lyophilized empty proteinoid carriers were resuspended in 0.85N citric acid and 0.5% gum containing heparin at a concentration of 20 mg/ml. The amount of heparin co-isolated with the proteinoid carriers was measured as described above.

Experimental Procedure

Male Spaque Dawley rats weighing approximately 350 g were dosed by oral gavage or intraduodenal (ID) injection (just anterior to the pyloric sphincter and into the duodenum). Rats were dosed orally or ID with one of the following: lyophilized heparin proteinoid carriers, heparin-spiked empty proteinoid carriers, proteinoid/heparin in water, heparin in 0.85N citric acid and 0.5% gum and heparin alone in water. In both oral and ID injection experiments, weight ratios of heparin:proteinoid were constant. The total heparin dose in the oral studies was 100 mg/kg body weight; in ID injections studies, it was 50 mg/kg. The proteinoid dose was 40 mg/kg for oral gavages and 20 mg/kg for ID injections. The dosing volume was approximately 0.3 to 0.5 ml. Approximately 0.5 ml of blood is serially withdrawn from the tail artery of each rat just prior to dosing ("0" time) and 1 h, 2 h and 4 h post-dosing. Serum from the blood samples are stored at −20° C. for heparin activity determination.

Results and Discussion

Figure 21:
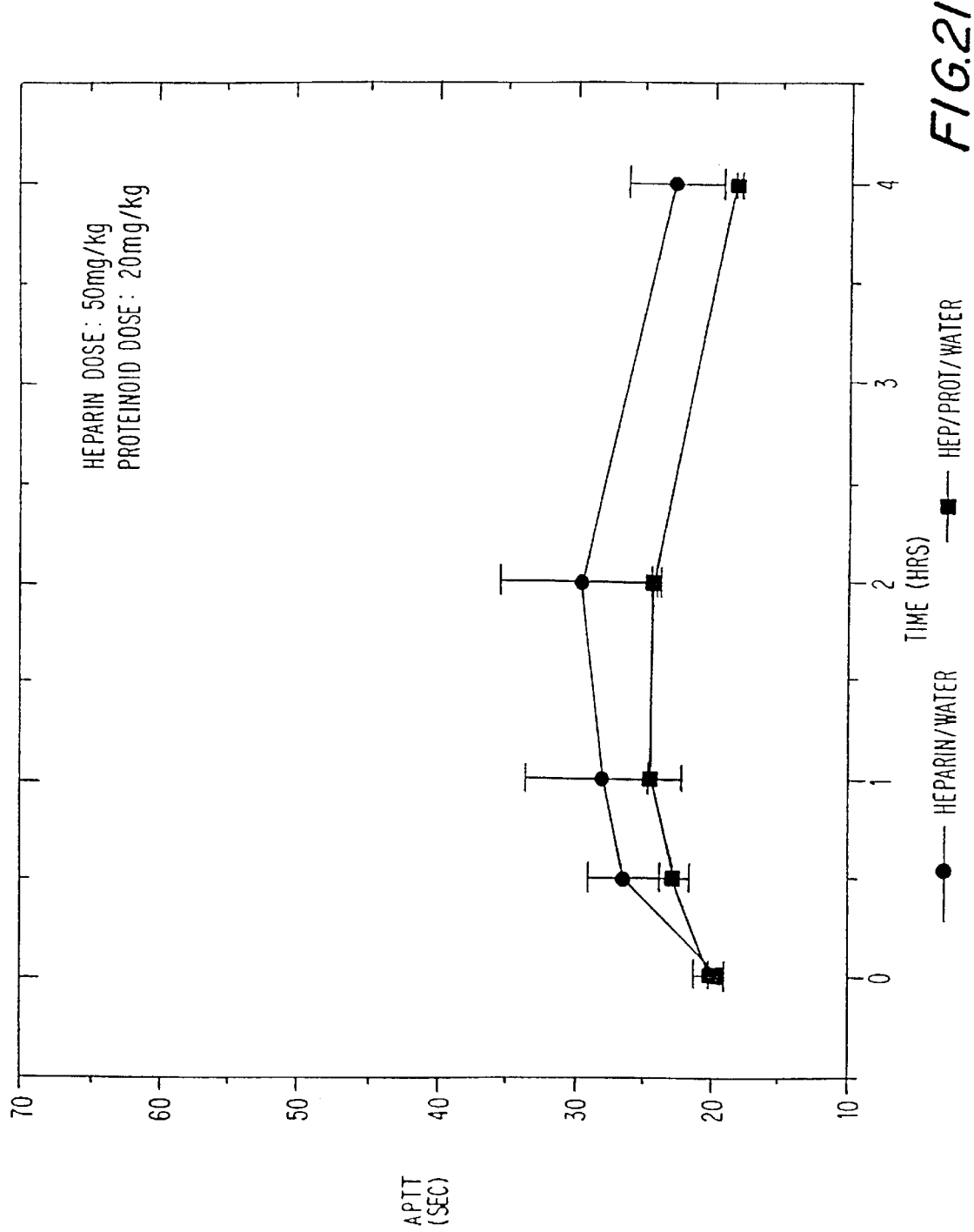
FIG. 21 illustrates the clotting times in rats dosed with heparin or proteinoid/heparin, both in water. The data represents an average of 6 rats. The data represents means +/−SEM.

The results obtained suggest that heparin alone as well as soluble proteinoid and heparin (both in water, dosed orally or by ID injection) did not appear to be absorbed from the GI tract in amounts sufficient to increase APTT values (FIG. 21). Heparin in citric acid elicited some increase in APTT values, but only when dosed directly into the duodenum.

Figure 22:
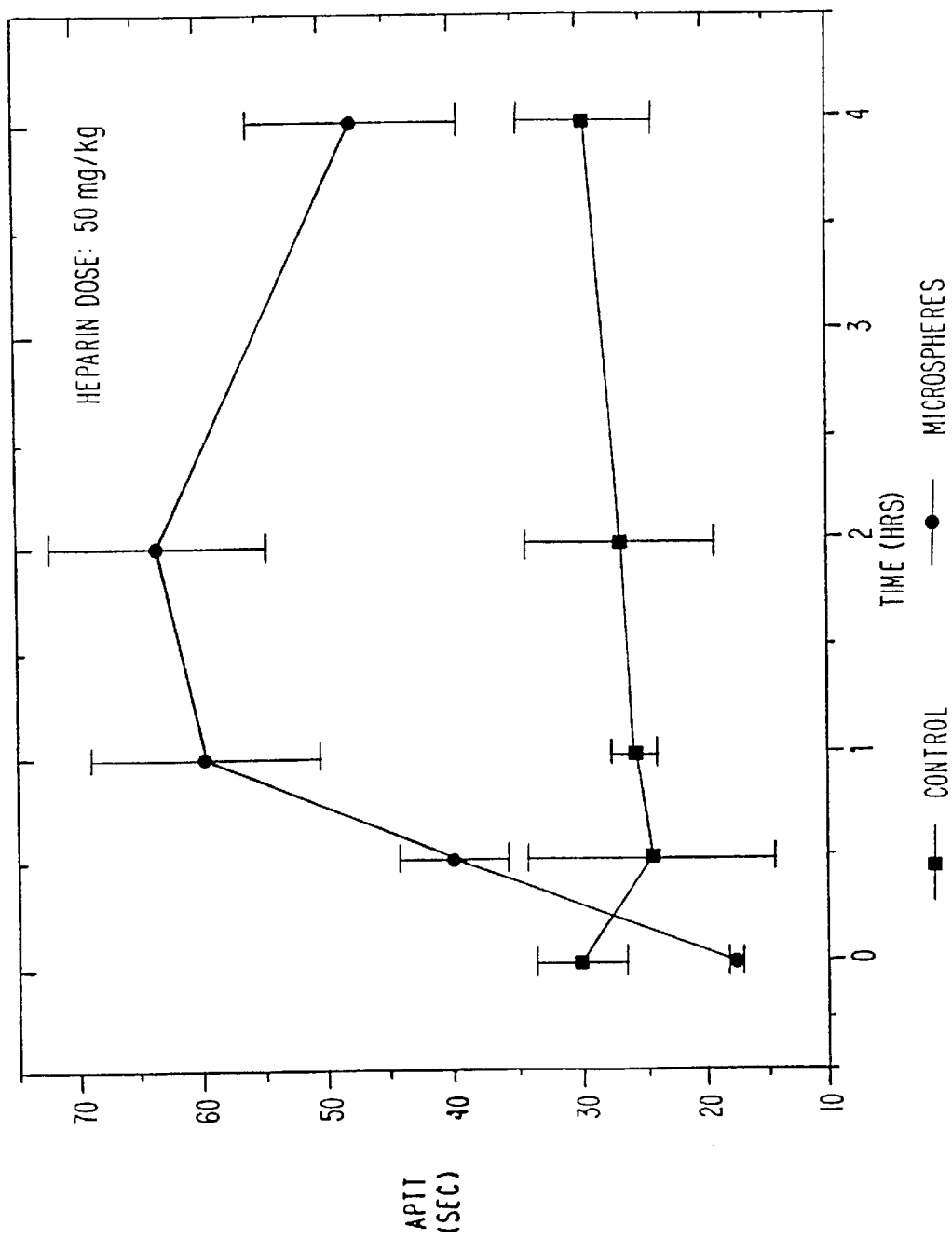
FIG. 22 illustrates clotting times in rats dosed ID with USP heparin or heparin proteinoid carriers, both in citric acid. Each time point is an average of 12 rats. The data represents means +/−SEM.
Figure 23:
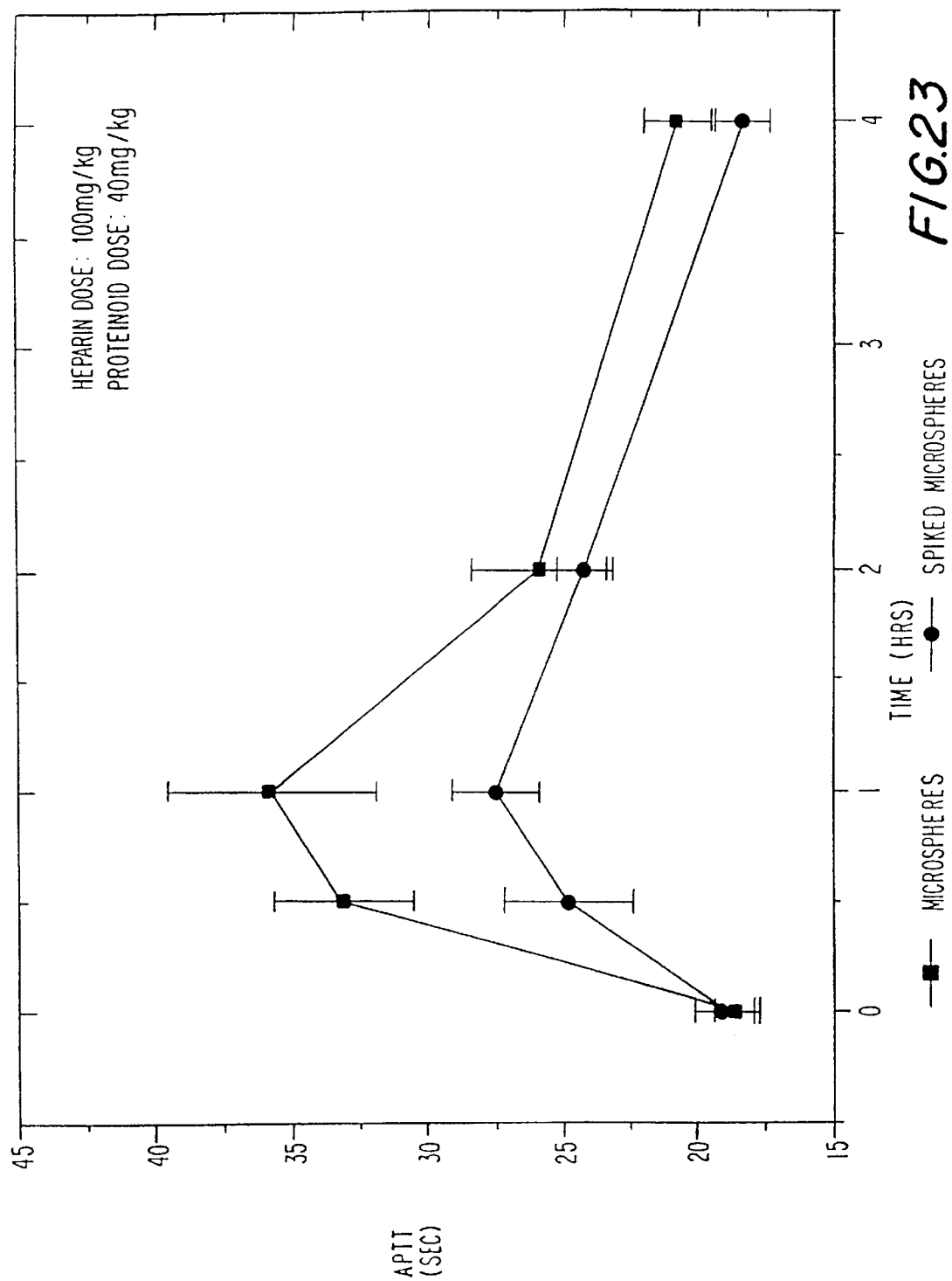
FIG. 23 illustrates clotting times in rats dosed orally with heparin-spiked empty proteinoid carriers or heparin proteinoid carriers. Each time point is an average of 12 rats. The data represents means +/−SEM.
Figure 24:
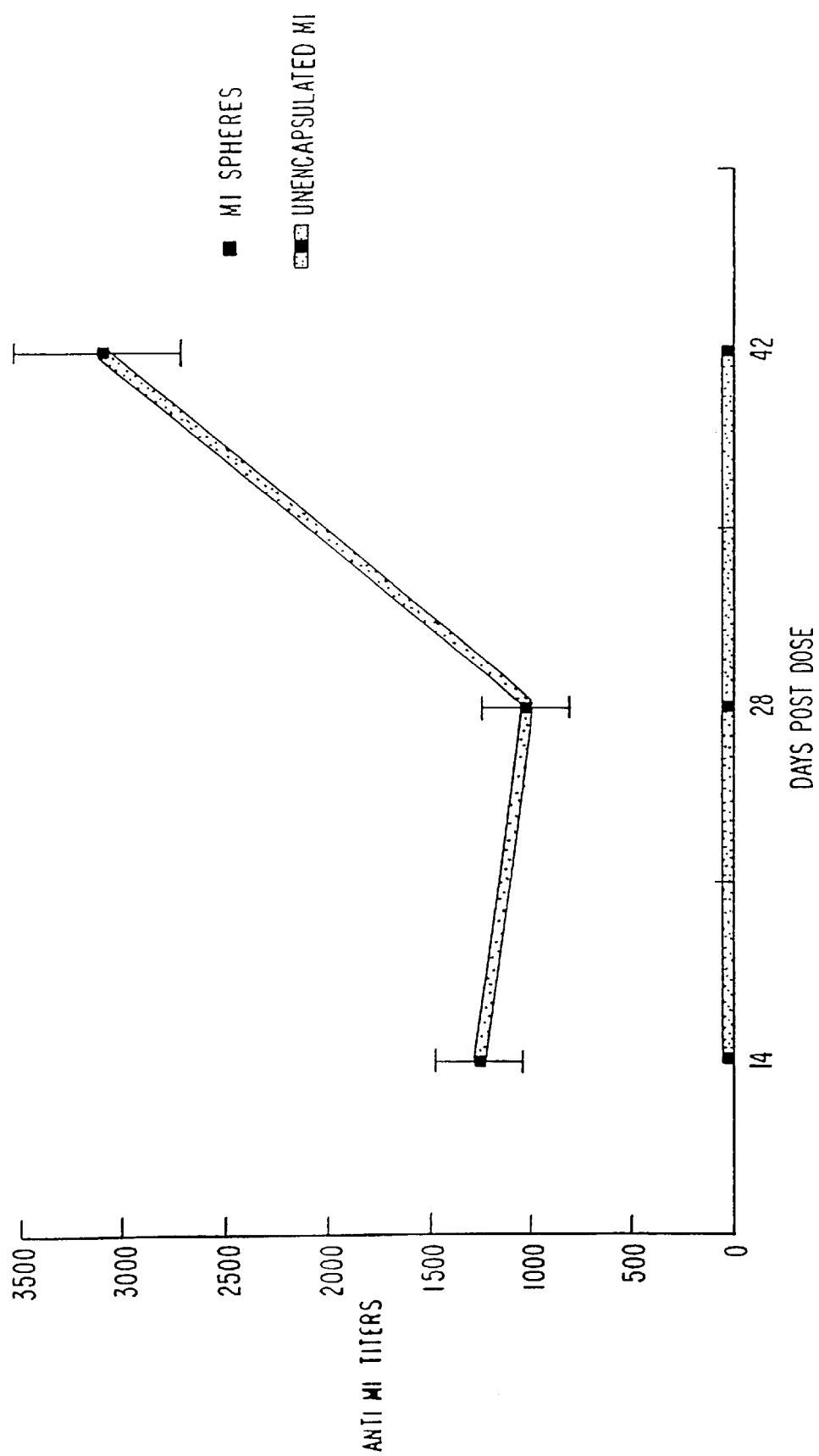
FIG. 24 illustrates the average titers of rats immunized orally with M1 proteinoid carriers versus unencapsulated M1. Only responders in each group were averaged.

Heparin proteinoid carriers gave the highest APTT values, indicated increased absorption of heparin when dosed orally, as well as when directly injected into the duodenum (FIGS. 22 and 23). While the observed activity was lower than observed with heparin proteinoid carriers (FIG. 23), heparin-spiked empty proteinoid carriers showed increased APTTs over baselines. Both types of proteinoid carriers showed a much greater increase in APTT values than that observed with citric acid/heparin.

The results obtained in this Example suggest that, in the proteinoid system, proteinoid carriers are necessary for the observed increase in heparin absorption, as soluble proteinoid did not show detectable activity within the experimental limits.

EXAMPLE 24

Preparation and Evaluation of M1-containing Proteinoid Carrier

In this Example, influenza virus antigen-containing proteinoid carriers were prepared and evaluated in rats.

Preparation of M1 Proteinoid Carriers

Figure 25:
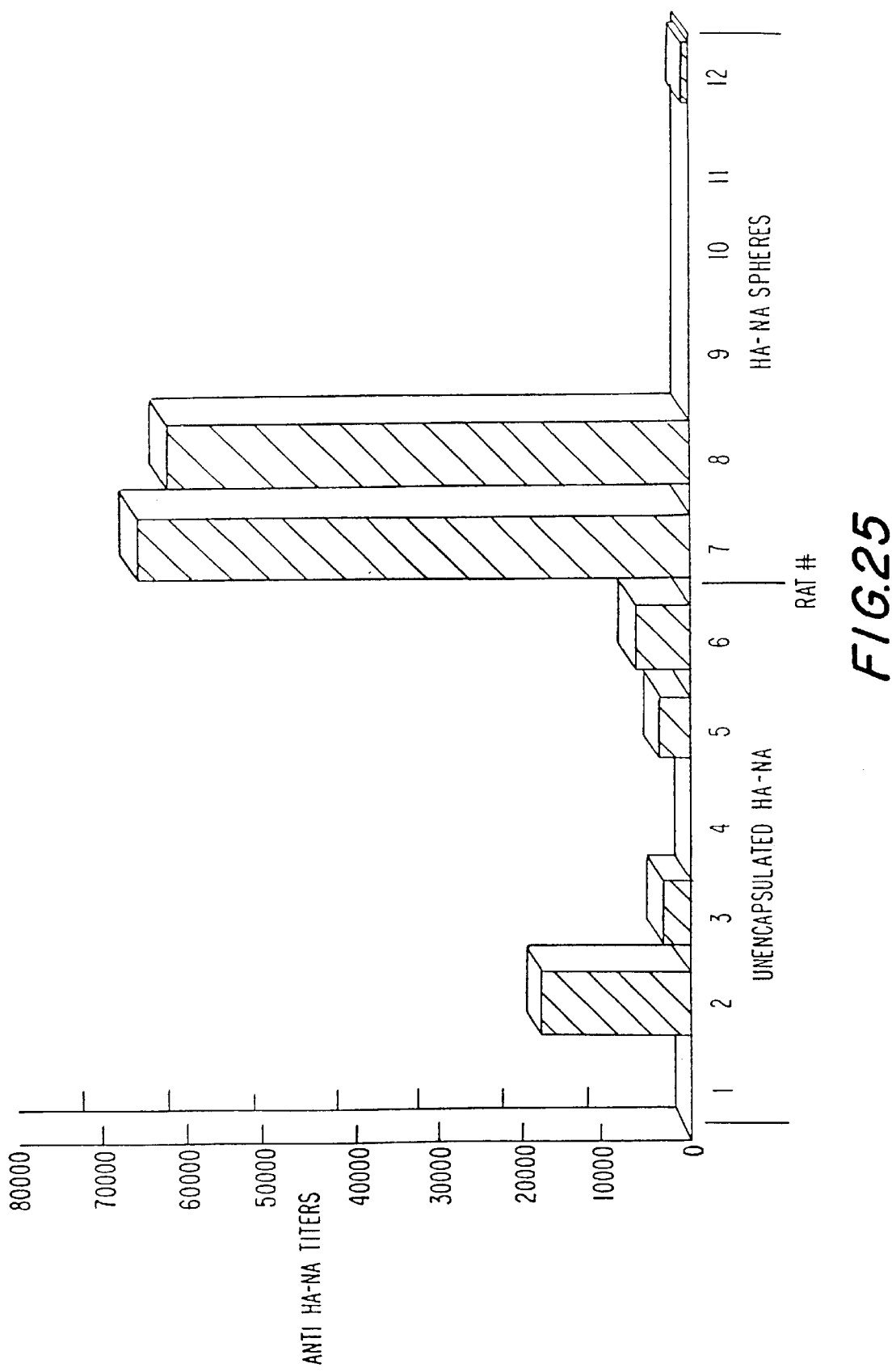
FIG. 25 illustrates HA-NA titers of rats immunized orally with HA-NA micropspheres versus unencapsulated HA-NA.

Encapsulation of M1 in proteinoid carriers was performed in the same manner described in Example 13. M1 protein, a major internal component of influenza virus, was obtained by purification of a swine influenza vaccine donated by Drug Directorate, Health Protection Branch, Bureau of Biologics, Ottawa, Ontrario Cannada. The vaccine was prepared with the high-yielding recombinant strain X-53 Aa, which derives its HA and NA from the parent strain A/NJ/11/76(H1N1) and its internal proteins, including M1, from the parent strain A/PR/8/34 (R. B. Couc et al. (1983) *Ann. Rev. Microbiol.*, Vol. 37, pages 529–549 and B. R. Murphy (1982) *Infec. Immun.*, Vol. 36, pages 1102–1108). M1 was purified as described by Khan et al ((1982) *J. Clin. Microbiol.*, Vol. 16, pages 813–820). M1 proteinoid carriers were prepared, by mixing (at 40° C.), equivolumes of an aqueous solution of 100 mg/ml of Glu/Asp/Tyr/Phe proteinoid in deionized water and a 10 mg/mL solution of M1 protein in 17 N citric acid and 5% gum arabic (pH 2.0). The final M1 concentration in the suspension was 1.0 mg/ml.

Preparation of HA-NA-containing Proteinoid Carriers and Unencapsulated Antigens

HA-NA antigen was isolated according to the procedure of Gallagher et al. ((1984) *J. Clin. Microbiol.*, Vol. 20, pages 80–93). Influenza virus (A/PR8/34) was centrifuged at 90,000 G for 60 min. The viral pellet was solubilized with 0.05M acetate buffer (pH 7.0) containing 7.5% octylglucoside and re-centrifuged under the same conditions. The resulting supernatant contained approximately 90% HA and 10% NA as determined by SDS-PAGE.

HA-NA proteinoid carriers were prepared following the same protocol as for the M1 proteinoid carriers but substituted M1 for HA-NA. The final concentration of HA-NA in the suspension was also 1.0 mg/ml.

"Empty" proteinoid carriers were prepared following the sampe procedure described for the M1, proteinoid carriers, with the only modification being that a 1.7 N citric acid/gum solution was used in place of the M1/citric acid/gum solution.

Unencapsulated antigens, M1 and HA-NA, was diluted in 1.7 N citric acid, 10 mg/ml gum arabic to the same final 1 mg/ml concentration.

Experimental Procedure

Male Spraque Dawley rats (about 350 g weight) were used in this experiment. Oral dosage was by gavage. Four groups of five rats each (the subcutaneous control group had 4) were dosed as follows: Group 1 was dosed orally with 1 mg of M1 proteinoid carriers per rat (1 ml), Group 2 was dosed orally with 1 mg per rat of "empty" proteinoid carrier, Group 3 was dosed with 1 mg of unencapsulated M1 per rat of "empty" carrier, Group 3 was dosed with 1 mg of unencapsulated M1 per rat in 1 ml and Group 4 was dosed subcutaneously (SC) with 25 ug per rat of M1 in 0.3 ml. Blood samples (300 ul) were taken from each rat by tail bleeeding before dosing and at 1, 2, 3 and 4 hours post-dose (to assay for antigen) and at 14, 28, and 42 days post-dose (for antibody assay). Solutions for subcutaneous control-M1 in TRIS (no SDS) was diluted to a concentration of 167 ug/mL. An equal amount of Freunds Complete Adjuvant (FCA, Sigma) was added and the mixture was thoroughly homogenized. The final concentration of M1 in the mixtue was 83.3 ug/ml. HA-NA solutions for subcutaneous administration were prepared in the same manner except that phosphate buffered saline replaced TRIS-SDS buffer.

The same immunization and bleeding schedule was follwed when dosing with HA-NA proteinoid carrier, with the following modifications: all rats received an oral booster with HA-NA proteinoid carrier (250 ug/rat) 42 days after the first oral dose and blood samples were again taken 14 days after the booster dose. Serum derived from the samples were stored at −20° C. until assayed.

Serum anti-M1 and anti-HA-NA specific IgGs were assayed by an ELISA method as described Khan et al. ((1982) *J. Clin. Microbiol.*, vol. 16, pages 813–820).

Results and Discussion

Attempts to measure antigen in plasma samples were unsuccessful. M1 antigen could not be detected in rat plasma samples taken 1–4 hours post-dosing in all groups, including the subcutaneous control.

Plasma samples from rats dosed orally with "empty" proteinoid carriers showed no significant antibody titer against either M1 or HA-NA antigens when assayed by ELISA (Table 8). As expected, rats dosed with 25 ug of either M1 or HA-NA antigen (with FCA) subcutanouesly developed a vigorous antibody response with titers that ranged from 54,000–330,000 in the case of M1 and 176, 750–909,000 in the case of HA-NA (Table 8).

Plasma samples from three of the five rats dosed with M1 proteinoid carriers showed a signficant primary response to M1 antigen. All three rats had titers ranging from 760 to 2150 as early as 14 days post-dosing, compared to <30 in all rats that received the amount of unencapsulated M1 (Table 8). Titers in the group that received proteinoid carriers increased to 1150–5200 by 42 days (FIG. 24).

Four out of six rats immunized with unencapsulated HA-NA did show a moderate anti-HA-NA IgG response, with titers of 3400–17,675, while two of six rats dosed with HA-NA proteinoid carrier showed a significant response (FIG. 25). The rats that did respond, however, reached titers at least eight times higher than those obtained in the controls. Although several rats showed higher titers after the oral booster with HA-NA proteinoid carriers given 42 days post-dose, most did not show a significant increase in titers.

The results support that a single dose of M1 proteinoid carriers was capable of inducing a significant IgG response to M1 as early as two weeks post-dosing, while rats dosed with same M1 (no proteinoid carriers) total dose showed no detectable antibody response. Similarly, a single dose of HA-NA proteinoid carriers induced a response in 33 of the rats used in the study. This response was up to eight times greater than rats dosed with unencapsulated HA-NA.

TABLE 8

ANTI M PROTEIN ANTIBODY TITERS IN SERUM FROM RATS DOSED WITH M PROTEINOID CARRIERS VS CONTROLS

| Dosing | rat # | 14 day titer | 28 day titer | 42 day titer |
|---|---|---|---|---|
| oral M protein unencapsulated 1 mg/rat | 197 | <30 | <30 | <30 |
| | 198 | <30 | <30 | <30 |
| | 199 | <30 | <30 | <30 |
| | 200 | <30 | <30 | 35 |
| | 201 | <30 | <30 | 56 |
| empty carrier | 203 | <30 | <30 | 82 |
| | 204 | <30 | <30 | 70 |
| | 205 | <30 | <30 | 60 |
| | 206 | <30 | <30 | 86 |
| | 207 | <30 | <30 | 45 |
| M proteinoid carriers 1 mg/rat total | 209 | <30 | <30 | 64 |
| | 210 | 2,150 | 820 | 5,200 |
| | 211 | 860 | 430 | 1,150 |
| | 212 | 760 | 1,850 | 3,000 |
| | 213 | <30 | <30 | 62 |
| subcut. control 0.025 mg/rat in FCA | 215 | 40,000 | 62,000 | 330,000 |
| | 217 | 34 | 8,000 | 54,000 |
| | 218 | 430 | 8,000 | 125,000 |
| | 219 | 270 | 6,600 | 78,000 |

PROTEINOID BATCHES

| Bt. No. | /AA COMPOSITION | ADDITIVE | TEMP C. | TIME (hr) | SPHERE RATING | BATCH SIZE molar | Operator Date |
|---|---|---|---|---|---|---|---|
| 085 | 3 GLU2 ASP2 ILEU | — | 170 | 3.0 | INS5 MT1 | 0.0 | |
| 086 | 3 GLU2 ASP2 VAL | — | 170 | 3.0 | INS4 MT0 HEP0 | 0.0 | |
| 087 | 3 GLU ASP LEU | — | 170 | 3.0 | INS5 MT3 REPS | 0.0 | |
| 088 | 2 GLU2 ASP2 EQU | SEE | MEMO | 0.0 | 0.0 | | |
| 089 | 2 GLU2 ASP2 EQU | — | 170 | 3.0 | INS5 MT0 | 0.0 | |
| 090 | 3 GLU2 ASP2 VAL | — | 170 | 3.0 | INS3 MT0 HEPI | 0.0 | |
| 091 | 3 GLU ASP LEU | — | 170 | 3.0 | INS2 MT1 | 0.0 | |
| 092 | 3 GLU ASP THR | — | 170 | 3.0 | INS2 MT0 | 0.0 | |
| 093 | 4 GLU2 ASP2 VAL PRO | — | 170 | 3.0 | INS2 MT2 | 0.0 | |
| 094 | 3 GLU ASP CYS-H | — | 170 | 3.0 | INS1 MT1 | 0.0 | |
| 095 | 4 PRO SER THR CYS | — | 170 | 3.0 | | 0.0 | |
| 096 | 3 GLU ASP VAL2 | — | 170 | 3.0 | INS3 MT0 HEP4 | 0.0 | |
| 097 | 3 GLU ASP VAL | — | 170 | 3.0 | INS2 MT1 | 0.0 | |
| 098 | 3 GLU ASP CYS-H | — | 170 | 3.0 | INS4 MT1 | 0.0 | |
| 099 | 2 GLU2 ASP2 EQU | — | 170 | 3.0 | INS4 | 0.0 | |
| 186 -cp | 4 PYGLU ASP TYR PHE | PA | 176 | 4.0 | INS0 MT4 HEP5 | 0.3 | |
| 199 -cp | 4 GLU ASP TYR PHE | H20 | 100 | 99.0 | MT0 INS0 HEP0 | 0.0 | |
| 202A-cp | 4 GLU2.4 ASP2 VAL2 GLY | — | 170 | 4.0 | INS3 MT0 | 0.6 | |
| 202B-cp | 4 GLU2.4 ASP2 VAL2 GLY | — | 170 | 4.0 | MT0 INS3 | 0.6 | |
| 206A-cp | 4 GLU ASP-TYR PHE | SULFA | 175 | 4.5 | INS4 MT4 HEP3 | 0.6 | |
| 206B-cp | 4 GLU ASP-TYR PHE | SULFA | 175 | 4.5 | | 0.6 | |
| 206C>3K | 4 GLU ASP-TYR PHE | SULFA | 175 | 4.5 | | 0.6 | |
| 207A-cp | 4 GLU ASP-TYR PHE | SULFA | 175 | 10.0 | INS5 MT4 HEP4 | 2.0 | |
| 207B-cp | 4 GLU ASP-TYR PHE | SULFA | 175 | 10.0 | MT5 INS4 HEP4 | 2.0 | |
| 211A-cp | 4 GLU ASP-VAL LYSFB | SULFA | 190 | 4.3 | INS5 MT5 HEP5 W | 0.3 | |
| 211B-cp | 4 GLU ASP-VAL LYSFB | SULFA | 190 | 4.5 | | 0.3 | |
| 212A-cp | 3 GLU2-TYR.PHE | SULFA | 185 | 5.0 | INS4 MT3 HEP4 | 0.3 | |
| 212B-cp | 3 GLU2-TYR PHE | SULFA | 185 | 5.0 | | 0.3 | |
| 214 -cp | 3 GLU LYSFB-ARG | SULFA | 180 | 7.0 | INS0 MT0 HEP0 | 0.0 | |
| 223 -cp | 4 LYSFB2 ARG2 LEU PGLU | SULFA | 180 | 8.0 | INS0 MT0 HEP2 | 0.3 | |
| 227A-cp | 2 VAL2 GLY2 | SULF | 180 | 1.5 | INS0 MT0 HEP0 | 0.1 | |
| 227B-cp | 2 VAL2 GLY2 | SULFA | 180 | 1.5 | MT0 INS0 HEP0 | 0.1 | |
| 228A-cp | 3 VAL2 GLY2 PGLU | SULF | 180 | 2.5 | INS0 MT0 HEP0 | 0.1 | |
| 228B-cp | 3 VAL2 GLY2 PGLU | SULFA | 180 | 2.5 | MT0 INS0 HEP0 | 0.1 | |
| 248 -cp | 3 GLU ASP LEU | — | 190 | 4.0 | INS3 MT0 HEPa | 0.0 | |

-continued

PROTEINOID BATCHES

| Bt. No. | /AA COMPOSITION | ADDITIVE | TEMP C. | TIME (hr) | SPHERE RATING | BATCH SIZE molar | Operator Date |
|---|---|---|---|---|---|---|---|
| 265A-cp | 4 GLU ASP-TYR PHE | SUL | 155 | 4.0 | INS4 MT4 HEP5 | 1.0 | |
| 265B | 4 GLU ASP -TYR PHE | SULFOLANE | 155 | 4.0 | | 1.0 | |
| 265C | | | | | .0 | .0 | |
| 296A-cp | 4 GLU LYSH PHE ASP | SUL-H | 180 | 3.0 | INS4 MT2 HEP0 | 0.6 | |
| 296B-cp | 4 GLU LYSH PHE ASP | SUL-H | 180 | 3.0 | | 0.6 | |
| 298 -cp | 4 GLU ASP-TYR PHE | SUL-H | 190 | 1.5 | INS1a MT3 HEP4 | 0.5 | |
| 301 -cp | 4 GLU ASP-TYR PHE | SUL | 175 | 8.0 | INS4 MT2 HEP3 | 2.0 | |
| 302 -cp | 4 GLU ASP-TYR PHE | HMePO | 190 | 1.5 | INS4 MT2 HEP3 | 0.3 | |
| 308 -cp | 4 GLU ASP TYR PHE | HMP | 170 | 1.0 | INS4 MT4 HEP4 | 0.3 | |
| 309 -cp | 4 -GLU1.3 ASP1.3 TYR PHE1.3 | SULFOLANE | 190 | 1.5 | INS4aMT3oaHEP4a | 0.3 | |
| 310 -cp | 4 -GLU ASP TYR PHE | SULFALANE | 190 | 4.0 | INS4 MT2 HEP5 | 1.0 | |
| 038 | 2 GLU2 ASP2 EQU | — | 160 | 1.5 | | 0.0 | |
| 039 | 3 ASP2 ARG ILEU | — | 170 | 0.0 | MT0 | 0.0 | |
| 040 | 2 GLU2 ASP2 EQU | — | 175 | 3.0 | | 0.0 | |
| 041 | 2 GLU2 ASP2 EQU | PA | 170 | 3.0 | | 0.0 | |
| 042 | 2 GLU2 ASP2 EQU | GLYC | 170 | 3.0 | MT0 | 0.0 | |
| 043 | 2 GLU2 ASP2 EQU | GLYC | 170 | 3.0 | INS4 MT4 | 0.0 | |
| 044 | 2 GLU2 ASP2 EQU | GLYC | 170 | 3.0 | MT0 | 0.0 | |
| 045 | 2 GLU2 ASP2 EQU | PA | 170 | 3.0 | MT1 | 0.0 | |
| 046 | 2 GLU2 ASP2 EQU | GLYC | 190 | 6.0 | MT0 | 0.0 | |
| 047 | 2 GLU2 ASP2 EQU | PA | 190 | 6.0 | MT0 | 0.0 | |
| 048 | 2 GLU2 ASP2 EQU | — | 190 | 6.0 | MT0 | 0.0 | |
| 049 | 2 GLU2 ASP2 EQU | — | 190 | 3.0 | MT0 | 0.0 | |
| 050 | 2 GLU2 ASP2 EQU | — | 170 | 3.0 | MT0 | 0.0 | |
| 051 | 2 GLU2 ASP2 EQU | — | 170 | 6.0 | | 0.0 | |
| 052 | 2 GLU2 ASP2 EQU | — | 170 | 6.0 | MT0 | 0.0 | |
| 053 | 2 GLU2 ASP2 EQU | — | 170 | 4.0 | INS0 MT0 | 0.0 | |
| 054 | 2 GLU2 ASP2 EQU | — | 200 | 3.5 | INS4 MT0 | 0.0 | |
| 055 | 2 GLU2 ASP2 EQU | — | 150 | 3.5 | MT-VERY SM | 0.0 | |
| 056 | 2 GLU2 ASP2 EQU | — | 110 | 4.3 | MT0 | 0.0 | |
| 057 | 2 GLU2 ASP2 EQU | — | 150 | 3.5 | MT0 | 0.0 | |
| 058 | 2 GLU2 ASP2 EQU | — | 180 | 5.0 | | 0.0 | |
| 059 | 2 GLU2 ASP2 EQU | — | 150 | 3.0 | INS0 MT0 | 0.0 | |
| 060 | 2 GLU2 ASP2 EQU | — | 160 | 3.0 | MT3 | 0.0 | |
| 061 | 2 GLU2 ASP2 EQU | — | 165 | 3.0 | MT & HO AM | 0.0 | |
| 062 | 2 GLU2 LEU | — | 170 | 3.0 | MT0 | 0.0 | |
| 063 | 2 GLU2 ASP2 EQU | — | 170 | 3.0 | | 0.0 | |
| 064 | 2 GLU2 LEU | — | 170 | 3.0 | INS2 MT0 | 0.0 | |
| 065 | 3 GLU2 ASP2 LEU | — | 170 | 3.0 | INS5 HEP0 H | 0.0 | |
| 066 | 2 GLU2 GLY | — | 170 | 3.0 | MT0 | 0.0 | |
| 067 | 2 ASP2 LEU | — | 165 | 3.0 | | 0.0 | |
| 068 | 2 ASP2 LEU | — | | 0.0 | | 0.0 | |
| 069 | 2 GLU2 ASP2 EQU | — | 170 | 3.0 | INS5 & AMORPHOU | 0.0 | |
| 070 | 3 GLU2 ASP2 LEU | — | 170 | 6.0 | HE | 0.0 | |
| 071 | 3 GLU ASP3 LEU | — | 170 | 2.6 | | 0.0 | |
| 072 | 2 GLU2 ASP2 EQU | — | 170 | 3.0 | INS0 MT0 | 0.0 | |
| 073 | 3 GLU ASP PRO | — | 170 | 4.0 | INS0 MT0 HEP0 | 0.3 | |
| 074 | 2 GLU2 ASP2 EQU | — | 170 | 3.0 | INS5 | 0.0 | |
| 076 | 2 GLU2 ASP2 EQU | — | 170 | 3.0 | MT3 N0 AM0 | 0.0 | |
| 077 | 2 GLU2 ASP2 EQU | — | 170 | 4.5 | INS5 | 0.0 | |
| 078 | 2 GLU2 ASP2 EQU | — | 170 | 4.0 | INS5 | 0.0 | |
| 079 | 4 GLU ASP PR0 LYS3 | — | 170 | 4.5 | LOST BATCH | 0.0 | |
| 080 | 3 GLU2 ASP2 ILEU | — | 170 | 4.0 | INS4 MT0 HEP0 | 0.0 | |
| 081 | 2 ARG LYS EQU | — | 170 | 3.0 | | 0.0 | |
| 082 | 2 GLU2 ASP2 EQU | — | 170 | 4.0 | INS4 MT3 | 0.0 | |
| 083 | 3 GLU2 ASP2 ILEU | — | 170 | 6.0 | INS4 MT1 HEP4 | 0.0 | |
| 084 | 3 GLU2 ASP2 ILEU | — | 170 | 3.0 | INS4 MT3 | 0.0 | |
| 311 -cp | 4 -GLU2 LYSH2 PHE2 ASP | SULFALANE | 190 | 1.7 | IND4o MT3o HEP3 | 1.7 | |
| 312 -cp | 4 -GLU2 LYSH2 PHE2 ASP | SULFALANE | 190 | 0.7 | INS4 MT2 HEP4a | 17.9 | |
| 313 -cp | 4 -GLU2 LYSH2 PHE2 ASP | SULFALANE | 180 | 3.0 | INS3 MT3 HEP3ao | 0.6 | |
| 314 -cp | 4 -ASP TYR PHE PGLU | SULFALANE | 190 | 2.5 | INS2a MT4aHEP4a | 0.6 | |
| 315 -cp | 4 GLU ASP-VAL LYSFB | sulfolane | 190 | 4.0 | INS4 MT4 HEP3 | 0.3 | |
| 316 -cp | 4 GLU ASP-TYR PHE | sulfolane | 180 | 21.0 | INS4 MT3a HEPa | 0.3 | |
| 317 -cp | 4 GLN-ASP TYR PHE | SULFOLANE | 175 | 4.0 | INS5 MT5 HEP5 | 0.3 | |
| 318 -cp | 5 GLU2 ASP2 TYR2 PHE2 ORN | sulfalane | 180* | .0 | MT1 INS4 HEP3a | 1.0 | |
| 319 -cp | 4 -TYR PHE ASP PGLU | SULFALANE | 190 | 2.5 | INS4aMT4 HEP4a | 0.3 | |
| 320 -cp | 4 -TYR PHE PGLU ASP | Sulfolane | 190 | 1.5 | INS4aMT4 HEP4 | 0.3 | |
| 321 -cp | 5 GLU2 ASP2 TYR2 PHE2 ORN | SULFOLANE | 180* | 3.0 | INS3aMT2aHEP4a | 1.0 | |
| 322 -cp | 4 GLU2 LYSH2 PHE2 ASP- | SULFOLANE | 192 | 1.2 | INS2 MT2 HEP2 | 0.6 | |
| 323 -cp | 4 GLU ASP TYR PHE- | SULFOLANE | 190 | .0 | ABORT | 16.0 | |
| 324 -cp | 4 -GLU ASP TYR PHE | SULFOLANE | 190 | 3.0 | INS4 MT4 HEP5a | 2.0 | |
| 325 -cp | 5 GLU2 ASP2 TYR2 PHE2 ORN | SULFOLANE | 180* | 3.0 | INS5a MT2a HEP | 1.0 | |
| 326 -CP | 4 -GLU ASP TYR PHE | SULFOLANE | 190 | 6.5 | INS3a MT0a HEP3 | 16.0 | |
| 326 -CP | 4 -GLU ASP TYR PHE | SULFOLANE | | .0 | INS4a MT4 HEP4a | .0 | |

-continued

PROTEINOID BATCHES

| Bt. No. | | /AACOMPOSITION | ADDITIVE | TEMP C. | TIME (hr) | SPHERE RATING | BATCH SIZE molar | Operator | Date |
|---|---|---|---|---|---|---|---|---|---|
| 327 | -CP | 4 -GLU ASP TYR PHE | SULFOLANE | 190 | 4.0 | INS4a MT5a HEP3 | 17.0 | | |
| 328 | -CP | 4 -GLU ASP TYR PHE | SULFOLANE | 190 | 3.0 | INS5a MT3aHEP3a | 17.0 | | |
| 328 | -7e | 4 -GLU ASP TYR PHE | SULFOLANE | | .0 | INS3a MT0a HEP4 | .0 | | |
| 329 | -cp | 4 -GLN ASP TYR PHE | SULFOLANE | 175 | 6.5 | INS5a MT3a HEPS | 1.0 | | |
| 330 | -cp | 2 ASP PHE | SULFOLANE | 180 | 3.0 | INS0a MT1a HEP0 | 0.5 | | |
| 331 | -CP | 2 ASP2 PHE | SULFOLANE | 180 | 3.0 | INS0a MT0a HEP0 | 0.5 | | |
| 332 | 332 | 2 ASP3 PHE | SULFOLANE | 180 | 3.0 | INS3aMTIaHEP0c | 0.5 | | |
| 333 | -7a | 4 -GLU ASP TYR PHE | SULFOLANE | 190 | 5.0 | INS2aMT4a HEP5a | 17.0 | | |
| 334 | -7ov | 4 -GLU ASP TYR PHE | SULFOLANE | 190 | 5.0 | INS4aMT5a HEP4a | 17.0 | | |
| 335 | -CP | 2 -ASP PHE2 | SULFOLANE | 180 | 3.0 | INS1aMT2aHEP1a | 0.5 | | |
| 336 | -11 | 5 -GLU2 ASP2 TYR2 PHE2 ORN | SULFOLANE | 180 | .0 | INS3a MT3a HEP4 | 2.0 | | |
| 337 | 337 | 2 -ASP2 TYR | SULFOLANE | 180 | 6.5 | INS2aMT0cHEP0c | 0.5 | | |
| 338 | -CP | 2 -ASP TYR | SULFOLANE | 180 | 3.0 | INS0 MT0 HEP0 | 1.0 | | |
| 339 | -CP | 2 -ASP3 TYR | SULFOLANE | 180 | 3.0 | INS0a MT0 HEP0 | 0.5 | | |
| 340 | | 4 -GLU ASP TYR PHE | SULFOLANE | | .0 | | 1.5 | | |
| 341 | | 4 -GLU ASP TYR PHE | | | .0 | | 17.0 | | |
| 342 | 342 | 2 -ASP TYR2 | SULFOLANE | | .0 | INS0MT0HEP0 | 0.5 | | |
| 342 | -CP | 2 -ASP TYR2 | SULFOLANE | | .0 | INS0a MT0 HEP0 | 0.5 | | |
| 343 | | 4 -GLU ASP TYR PHE | SULFOLANE | | .0 | | 17.0 | | |
| 344 | | 4 -GLU ASP TYR PHE | SULFOLANE | | .0 | | 2.0 | | |
| 345 | -CP | 2 - ASP2 PHE | SULFOLANE | | .0 | INS0a MT0 HEP0 | .0 | | |
| 346 | -CP | 4 -GLN ASP TYR PHE | SULFOLANE | | .0 | INS0aMT1aHEP2A | .0 | | |
| 347 | | 4 -GLU2 ASP2 TYR5 PHE5 | SULFOLANE | | .0 | | .0 | | |
| 348 | | 2 -ASP2 PHE | SULFOLANE | | .0 | | .0 | | |
| 349 | | 2 -PHE ASP2 | SULFOLANE | | .0 | | .0 | | |
| 350 | | 2 -ASP2 PHE | SULFOLANE | | .0 | | .0 | | |
| 351 | 351 | 3 -GLU2 TYR PHE | SULFOLANE | | .0 | INS3aMT2aHEP3a | .0 | | |
| 352 | | 5 -GLU2 ASP2 TYR2 PHE2 ORN | SULFOLANE | | .0 | | .0 | | |
| 353 | | 5 -GLU2 ASP2 TYR2 PHE2 ORN | SULFOLANE | | .0 | | .0 | | |
| 295 | -CP | 1 ASP | SUL-H | 180 | 1.5 | INS2aMT2aHEP3oa | 0.3 | | |
| 297 | -cp | 4 GLU ASP-TYR PHE | SUL-H | 190 | 1.5 | INS5 MT4a HEP2 | 0.5 | | |
| 299 | -cp | 4 GLU LYS PHE ASP | SUL-H | 190 | 1.7 | INS5 MT4 HEP2 | 0.6 | | |
| 300 | -cp | 5 GLU ORN ASP LYS PHE | — | 180 | 3.0 | INS3 MT3 HEP3 | 0.3 | | |
| 303 | -cp | 4 GLU ASP-TYR PHE | SUL-H | 175 | 8.0 | INS4 MT2 HEP3a | 2.0 | | |
| 304 | -cp | 5 GLU ASP-TYR PHE ORN0.5 | SUL-H | 180 | 3.0 | INS4 MT2 HEP3 | 2.0 | | |
| 305 | | 4 -PGLU ASP.5TYR PHE | SUL | | 0.0 | INS3 MT2 HEP3 | 0.3 | | |
| 306 | -cp | 4 -GLU ASP .5TYR PHE | SUL | | 0.0 | INS3aMT2aHEP2a | 0.3 | | |
| 307 | -cp | 4 GLN ASP TYR PHE | SULFOLANE | 175 | 4.0 | INS4o MT4 HEP4o | 0.3 | 1 | |
| - | | | | | .0 | | .0 | | |
| 000 | | | | | .0 | | | | |
| 001 | | 2 GLU2 ASP2 EQU | — | 170 | 4.0 | | 0.0 | | |
| 002 | | 2 GLU ASP EQU | — | 149 | 0.0 | | 0.0 | | |
| 003 | | 2 GLU ASP EQU | — | 163 | 0.0 | | 0.0 | | |
| 004 | | 0 | — | 204 | 0.0 | | 0.0 | | |
| 005 | | 2 GLU ASP EQU | — | 176 | 3.0 | | 0.0 | | |
| 006 | | 2 GLU ASP EQU | — | 154 | 3.0 | | 0.0 | | |
| 007 | | 2 GLU ASP EQU | — | 196 | 2.0 | | 0.0 | | |
| 008 | | 2 GLU ASP EQU | — | 154 | 3.6 | | 0.0 | | |
| 009 | | 2 GLU2 ASP2 EQU | — | 192 | 3.0 | | 0.0 | | |
| 010 | | 2 GLU2 ASP2 EQU | — | 163 | 4.0 | | 0.0 | | |
| 011 | | 2 GLU2 ASP2 EQU | — | 160 | 5.0 | | 0.0 | | |
| 012 | | 2 GLU2 ASP2 EQU | — | 154 | 4.0 | | 0.0 | | |
| 013 | | 2 GLU2 ASP2 EQU | — | 176 | 4.0 | | 0.0 | | |
| 014 | | 2 GLU2 ASP2 EQU | — | 174 | 3.5 | | 0.0 | | |
| 016 | | 2 GLU2 ASP2 EQU | — | 170 | 3.5 | | 0.0 | | |
| 017 | | 2 GLU2 ASP2 EQU | — | 170 | 3.5 | | 0.0 | | |
| 018 | | 2 GLU2 ASP2 EQU | — | 170 | 3.5 | | 0.0 | | |
| 019 | | 2 GLU ASP EQU | — | 180 | 3.5 | | 0.0 | | |
| 020 | | 2 GLU2 ASP2 EQU | — | 180 | 4.5 | HT | 0.0 | | |
| 021 | | 2 GLU2 ASP2 EQU | — | 180 | 3.5 | | 0.0 | | |
| 022 | | 2 GLU2 ASP2 EQU | — | 180 | 3.5 | | 0.0 | | |
| 023 | | 2 GLU2 ASP2 EQU | — | 180 | *3.3 | | 0.0 | | |
| 024 | | 2 GLU2 ASP2 EQU | — | 175 | 3.3 | | 0.0 | | |
| 025 | | 2 GLU2 ASP2 EQU | — | 175 | 3.0 | | 0.0 | | |
| 026 | | 3 GLU2 ASP2 ASPG | — | 175 | 3.0 | | 0.0 | | |
| 027 | | 3 GLU2 ASP2 SER | — | 195 | 5.0 | | 0.0 | | |
| 028 | | 2 GLU2 ASP2 EQU | — | 175 | 3.5 | | 0.0 | | |
| 029 | | 2 GLU2 ASP2 EQU | — | 175 | 3.5 | | 0.0 | | |
| 031 | | 2 GLU2 ASP2 EQU | — | 170 | 3.3 | | 0.0 | | |
| 032 | | 2 GLU2 ASP2 EQU | — | 170 | 3.5 | MT0 | 0.0 | | |
| 033 | | 2 GLU2 ASP2 EQU | — | 175 | 3.0 | MT0 | 0.0 | | |
| 034 | | 2 GLU2 ASP2 EQU | — | 180 | 0.0 | MT0 | 0.0 | | |
| 035 | | 2 GLU2 ASP2 EQU | — | | 3.0 | MT0 | 0.0 | | |
| 036 | | 2 GLU2 ASP2 EQU | — | 175 | 3.6 | MT0 | 0.0 | | |

-continued

PROTEINOID BATCHES

| Bt. No. | /AACOMPOSITION | ADDITIVE | TEMP C. | TIME (hr) | SPHERE RATING | BATCH SIZE molar | Operator Date |
|---|---|---|---|---|---|---|---|
| 037 | 2 GLU2 ASP2 EQU | — | 175 | 21.0 | INS0 MT0 HEP0 | 0.0 | |
| 249 >3K | 4 GLU2LEU2LYSH2PGLU | — | 180 | 3.0 | INS0 MT0 HEP0 | 0.1 | |
| 250 >3K | 5 PGLUARGH2LYS2LEUASP2 | — | 180 | 3.0 | INS0 MT0 HEP0 | 0.1 | |
| 251 >3K | 4 GLU2ASP2TYR5-PHE5 | SUL-H | 180 | 3.0 | INS4 MT4 HEP2 | 0.1 | |
| 252 -cp | 4 (GLU+ASP)VAL LYS | — | 170 | 3.0 | INS1 MT2 HEP1 | 0.0 | |
| 253 -cp | 4 GLU ASP-TYR PHE | SUL-H | 180 | 4.5 | INS1 MT0 HEP0 | 2.0 | |
| 253 | 4 GLU ASP-TYR PHE | SUL-H | 180 | 10.0 | INS4 MT4 HEP4 | 1.0 | |
| 254 -cp | 5 GLU2ASP2-TYR2PHE2ORN | SUL-H | 180 | 8.5 | INS4 MT4 HEPA | 0.1 | |
| 255 -cp | 5 GLU ASPTYR-PHE ORN | SUL-H | 180 | 3.0 | INS2 MT4 HEP4 | 0.3 | |
| 256 -cp | 4 GLU2LYSH2PHE2PGLU | — | 180 | 3.0 | INS0 MT0 HEP0 | 0.1 | |
| 257 -cp | 4 GLU ASP ARGH ORNH | — | 180 | 3.0 | INS0 MT0 HEP0 | 0.0 | |
| 258 >3K | 3 GLU ASP ARGH | — | 180 | 3.0 | INS1 MT1 HEP0 | 0.0 | |
| 259 >3K | 4 GLU ASP-TYR PHE | SUL-H | 180 | 3.0 | INS3 MT3 HEP3 | 0.3 | |
| 260 >3K | 4 GLU ASP-TYR PHE | SUL-H | 180 | 2.5 | INS2 MT3 HEP2 | 0.3 | |
| 261 -cp | 4 GLU ASP-TYR PHE | SUL-H | 180 | 3.0 | INS0 MT0 HEP0 | 0.3 | |
| 262 -cp | 4 GLU LORN ASP LYSFB | SUL-H | 180 | 3.5 | INS0 MT1 HEP4 | 0.3 | |
| 263 -cp | 4 GLU2 LYSH2 PHE2 ASP | — | 190 | 3.0 | INS3 MT3 HEP0 | 0.3 | |
| 264 -cp | 4 GLU2 LYSH2 PHE2 ASP | — | 180 | 3.2 | INS5 MT3 HEP4 | 0.3 | |
| 266 -cp | 4 GLU2 LYSH2 PHE2 ASP | — | 180 | 3.0 | INS4 MT4 HEP4 | 0.3 | |
| 267 -cp | 3 GLU LYSFB ASP LYSFB | SUL-H | 180* | 3.0 | INSa MTC HEPc | 0.3 | |
| 268 | 4 GLU ASP-TYR PHE | SUL-H | 190 | 2.5 | INS0 MT0 HEP0 | 0.3 | |
| 269 -cp | 4 GLU ORNH ASP-LYSFB | SUL-H | 180 | 4.0 | INSc MTc HEPc | 0.1 | |
| 270 -cp | 4 GLU ASP-TYR PHE | SUL-H | 180 | 1.5 | INS5 MT4 HEP0 | 1.5 | |
| 271 | 3 GLU LYSFB-PHE | SUL-H | 190 | 1.5 | INS3aMT4oHEP4o | 0.0 | |
| 272 -cp | 4 GLU2 LEU2 LYSH2 TYR1 | — | 180 | 3.0 | INSc MT1 HEP4 | 0.1 | |
| 273 -cp | 4 GLU2 LEU2 LYSH2 PHE1 | — | 180 | 3.0 | INS2aMT2 HEP2,a | 0.1 | |
| 274 -cp | 3 GLU LEU ARG TYR | — | 180 | 3.0 | INSc MTc HEPc | 0.1 | |
| 275 -cp | 4 GLU ARGH-TYR | SUL | 190 | 1.5 | INSc MTc HEPc | 0.3 | |
| 276 -cp | 4 GLU2 LEU2 ARG2 PHE | — | 180 | 3.0 | INS3 MT3 HEP4 | 0.1 | |
| 277 -cp | 3 GLU LYS TYR | SUL-H | 190 | 1.5 | INSc MTc HEP4o | 0.3 | |
| 278 -cp | 3 GLU LYS PHE | SUL-H | 190 | 1.5 | INSc MTC HEP4 | 0.3 | |
| 279 -cp | 3 GLU LYS ALA | — | 190 | 1.5 | INSc MTc HEPc | 0.3 | |
| 280 -cp | 4 GLUGLUASPGLUTYRGLPHE | SUL-H | 190 | 1.5 | INS4 MT3 HEP4 | 0.4 | |
| 281 -cp | 4 GLU1 ASP1 TYR2.5-PHE2.5 | SUL-H | 180 | 3.0 | INS4 MTa HEP2a | 1.0 | |
| 282 -cp | 3 GLU2 LYS5 PHE2 | — | 190 | 1.5 | INS0 MT0 HEP2 | 0.3 | |
| 283 -cp | 4 GLU2 LYS5 PHE5 TYR2 | — | 190 | 1.5 | INS0 MTD HEP3 | 0.1 | |
| 284 | 5 GLU2ASP2-TYR2PHE2ORN | SUL-H | 180 | 3.0 | INS4aMT4oHEP2a | 1.0 | |
| 285 -cp | 2 GLU(2X) ASP(2X) | — | 180 | 3.0 | INSc MTc HEPc | 0.3 | |
| 286 -cp | 2 GLU ASP(2X) | — | 180 | 2.5 | INSc MTc HEPc | 0.3 | |
| 287 -cp | 2 GLU PHE | — | 180 | 3.5 | INS3 MT2 HEP3 | 0.3 | |
| 288 -cp | 3 GLU ORN PHE | — | 180 | 3.0 | INSc MTc HEPc | 0.3 | |
| 289 | 2 GLU ARG | — | 180 | 1.0 | | 0.3 | |
| 290 -cp | 3 GLU ARG PHE | — | 180 | 3.0 | INS2 MT2 HEP2 | 0.3 | |
| 291 -CP | 3 GLU LYS PHE | SUL-H | 190 | 1.5 | INS4 MT3o HEP4o | 0.3 | |
| 292 -cp | 5 GLU ASP ARG ORN PHE | SUL-H | 180 | 3.0 | INS0 MT0 HEP0 | 0.3 | |
| 293 -cp | 4 GLU ASP ARG ORN PHE | SUL-H | 180 | 3.0 | INS3 MT3 HEP3 | 0.3 | |
| 294 -cp | 4 GLU2 LYSH2 PHE2 ASP | — | 180 | 3.0 | INS3 ML4 HEP4 | 0.3 | |
| 192 -cp | 3 GLU LYSFB ASP | — | 180 | 3.0 | INS4 MT0 | 0.3 | |
| 193 >6K | 4 (GLU+ASP) TYR PHE | PA | 175 | 4.0 | MT0 HEP0 | 0.3 | |
| 194 -cp | 3 GLU LYSFB ASP | TRIGL | 195 | 3.0 | INS1 MT0 HEP2 | 0.3 | |
| 195 -cp | 3 GLU ASP VAL2 | — | 170 | 3.2 | INS2 MT1 HEP0 | 0.3 | |
| 196 -cp | 4 GLU ASP TYR PHE | PA | 175 | 4.2 | INS2 MT5 HEP4 | 1.0 | |
| 197 -cp | 4 GLU ASP TYR PHE | SUL | 175 | 2.7 | INS2 MT5 HEP5 | 0.3 | |
| 198 -cp | 3 GLU LYSFB ASP | — | 195 | 3.2 | INS3 | 1.0 | |
| 200 -cp | 3 GLU LYSH ASP | PA | 185 | 3.0 | INS4 MT0 HEP0 | 0.3 | |
| 201 -cp | 3 GLU LYSFB ASP | SULFA | 195 | 3.0 | INS4 MT0 HEP3 | 0.3 | |
| 203 -cp | 4 GLU ASP VAL LYS | — | 170 | 3.0 | INS5 MT5 HEP | 0.3 | |
| 204 -cp | 3 GLU LYS ASP | — | 185 | 3.0 | INS4 MT0 HEP0 | 0.3 | |
| 205 -cp | 4 GLU ASP-TYR PHE | SULFA | 175 | 3.7 | INS4 MT0 | 0.6 | |
| 208 | 3 GLUM LYSH ASPH | NaHCO&MeOH | 80 | 8.0 | INS0 MT0 HEP0 | 0.0 | |
| 209 -cp | 4 GLU ASP-VAL LYS | SULFA | 170 | 3.2 | INS4 MT4 HEP3 W | 0.3 | |
| 210 -cp | 4 GLU ASP-VAL LYSFB | SULFA | 170 | 3.0 | INS4 MT4 HEP3 | 2.0 | |
| 213 -cp | 3 GLU-LYS HIS | SULFA | 180 | 3.0 | INS0 MT0 HEP0 | 0.3 | |
| 215 -cp | 3 GLU ASP GLY2 | — | 180 | 5.5 | INS3 MT0 HEP0 | 0.3 | |
| 216 -cp | 4 GLU ASP-TYR PHE | SULFA | 175 | 3.0 | INS4 MT4 HEP4 | 2.0 | |
| 217 | 3 GLUASPLYS(DIETESTER) | HEOH/Et3H | 75 | 29.0 | | 0.0 | |
| 218 -cp | 4 GLU ASP-TYR PHE | SULFA | 175 | .0 | INS0 MT0 HEP0 A | 0.3 | |
| 219 -cp | 3 GLU-LYS-LEU | sul/P0C13 | 180* | 8.5 | INS2 MT0 HEP2 | 0.3 | |
| 220 -cp | 4 GLU ASP-TYR PHE | SULFA | 180 | 20.5 | INS4 MT4 HEP5 | 0.3 | |
| 221 -cp | 3 -ASP2 TYR PHE | SULFA | 180 | 22.0 | INS4 MT4 HEP4 | 0.3 | |
| 222 -cp | 3 -LYSFB2 ARG2 LEU | SULFA | 180 | 4.0 | INS0 MT0 HEP2 | 0.3 | |
| 224 -cp | 4 GLU ASP-TYR PHE- | SU/PA | 180 | 6.0 | INS3 MT0 HEP0 | 0.3 | |
| 225 -cp | 3 PRO-SER TYR | SULF | 180 | 3.5 | INS2 MT0 HEP0 | 0.3 | |
| 226 >3K | 4 GLU ASP TYR PHE | SULF | 180 | 4.0 | INS3 MT4 HEP3 | 0.3 | |

-continued

PROTEINOID BATCHES

| Bt. No. | | /AACOMPOSITION | ADDITIVE | TEMP C. | TIME (hr) | SPHERE RATING | BATCH SIZE molar | Operator Date |
|---|---|---|---|---|---|---|---|---|
| 229 | >3K | 4 -GLU ASP TYR PHE | SULF | 380 | 5.5 | INS3 MT0 HEP0 | 0.3 | |
| 230 | -cp | 2 GLU TYR | — | 180 | 4.0 | INS4 MT0 HEP0 | 0.3 | |
| 231 | -cp | 3 GLU LYSFB PHE | SULF | 180 | 3.5 | INS2 MT0 HEP0 | 0.3 | |
| 232 | -cp | 3 GLU LEU ARG | — | 180 | 4.0 | INS0 MT0 HEP0 | 0.3 | |
| 233 | -cp | 3 GLU LEU LYSH | — | 180 | 4.0 | INS4 MT0 HEP0 | 0.3 | |
| 234 | -cp | 4 -(GLU ASP TYR PHE) | SULF | 150 | 27.0 | INS3 MT0 HEP0 | 0.3 | |
| 235 | -cp | 4 -(GLU ASP)TYR1OPHE1O | SULF | 180 | 22.0 | INS0 MT0 HEP0 | 0.0 | |
| 236 | -cp | 3 GLU TYR LYSHCL | — | 180 | 2.0 | INS0 MT0 HEP0 | 0.3 | |
| 237 | >3K | 4 GLU2 LEU2 LYSH2 ASP | — | 180 | 3.0 | INS0 MT0 HEP0 | 0.1 | |
| 238 | >3K | 4 GLU ASP TYR5 PHE5 | SULF | 180 | 3.0 | INS0 MT0 HEP0 | 0.1 | |
| 239 | -cp | 3 -GLU ASP LEU | SUL-H | 190 | 1.0 | INS3 MT0 HEP0- | 0.0 | |
| 240 | -cp | 3 -(GLU ASP) LEU | SUL-H | 170 | 4.0 | INS4 MT0 HEP0 | 0.0 | |
| 241 | >3K | 3 -(GLU ASP) LEU | SUL-H | 190 | 5.0 | INS3 MT0 HEP0 | 0.0 | |
| 242 | -cp | 3 (GLU ASP) LEU | SUL-H | 170 | 2.5 | INS0 MT0 HEP0 | | 0.0 |
| 243 | -cp | 5 PGLU2ASPARG2LYS2LEU | — | 180 | 3.0 | INS0 MT0 HEP0 | 0.1 | |
| 244 | -cp | 3 (GLU ASP) LEU | — | 190 | 2.5 | INS0 MT0 HEP0 | 0.0 | |
| 245 | -cp | 3 (GLU ASP) LEU | — | 170 | 1.0 | INS3 MT1 HEP0 | 0.0 | |
| 246 | >3K | 5 GLU2 LYSH2 PHE2 ASP | — | 180 | 6.0 | INS4 MT4 HEP4 | 0.0 | |
| 247 | -cp | 3 GLU ASP LEU | — | 170 | 5.0 | INS0 MT0 HEP0 | 0.0 | |
| 145 | | 3 GLU ASP LYSFB | PPA | 185 | 6.0 | MT0 | 0.0 | |
| 146 | | 3 GLU ASP VAL2 | PPA | 170 | 3.5 | INS2 MT0 | 0.0 | |
| 147 | | 4 GLU ASP PHE ALA | — | 170 | 3.0 | 1NS4 MT3 HEP4 | 0.0 | |
| 148 | | 4 GLU ASP TYR PHE | PA | 170 | 3.0 | MT0 HEP4 | 0.0 | |
| 149 | | 3 GLU ASP PHE2 | — | 170 | 3.0 | | 0.0 | |
| 150 | | 4 GLU ASP LEU PHE | PA | 170 | 24.0 | MT0 HEP0 | 0.0 | |
| 151 | | 4 GLU ASP TYR PHE | PA | 170 | 6.0 | INS4 MT4 HEP4 | 0.0 | |
| 152 | | 4 GLU ASP TYR PHE | PA | 170 | 5.0 | | 0.0 | |
| 153 | | 3 GLU LYSFB PHE | PA | 170 | 24.0 | | 0.0 | |
| 154 | | 4 GLU ASP TYR PHE | PA | 170 | 4.0 | | 0.0 | |
| 155 | | 3 GLU2 TYR PHE | PA | 170 | 4.0 | INS4 MT5 HEP3 | 0.0 | |
| 156 | | 3 GLU4 LYS2 PHE | — | 170 | 6.0 | INS0 MT0 HEPc | 0.0 | |
| 157 | | 3 GLU2 TYR LEU | PA | 170 | 5.0 | INS2 MT1 HEP0 | 0.0 | |
| 158 | | 3 GLU2 PHE LEU | PA | 175 | 5.0 | INS4 MT0 HEP4 | 0.0 | |
| 159 | | 3 GLU3 PHE TYR | PA | 175 | 5.0 | INS4 MT4 HEP4 | 0.0 | |
| 160 | | 4 GLU6 LYS2 PHE TYR | PA | 170 | 6.0 | INSa MTc HEPc | 0.0 | |
| 161 | | 4 GLU4 PHE2 TYR2 CYS | PA | 170 | 4.0 | INS4 MT HEP | 0.0 | |
| 162 | | 3 GLU2 TYR PHE | PA | 170 | 5.5 | INS3 MT0 HEP2 | 0.0 | |
| 163 | | 3 GLU2 PHE TYR | PA | 170 | 5.0 | INS3 MT2 HEP3 | 0.0 | |
| 164 | | 3 GLU2 PHE TYR | PA | 170 | 5.0 | INS4 MT4 HEP4 | 0.0 | |
| 165 | | 4 GLU3 ASP PHE2 TYR2 | PA | 170 | 3.0 | INS3 MT0 HEP0 | 0.0 | |
| 166 | | 3 GLU LYSFB PGLU | PA | 170 | 7.0 | | 0.0 | |
| 167 | | 4 GLU ASP TYR PHE | PA | 170 | 6.5 | | 0.0 | |
| 168 | | 3 GLU ASP LYSFB | PPA | 185 | 72.0 | MT0 | 0.0 | |
| 169 | | 3 GLU ASP LYSFB | PPA | 185 | 72.0 | MT0 | 0.0 | |
| 170 | | 3 GLU ASP LYSFB | — | 195 | 7.0 | MT5 | 0.0 | |
| 171 | | 3 GLU LSYHCL ASP | H.OIL | 180 | 7.0 | MT0 | 0.0 | |
| 172 | | 4 GLU ASP TYR PHE | PA | 170 | 6.0 | MT1 | 0.0 | |
| 173 | | 3 GLU LYS ASP | mineral o. | 185 | 3.0 | ABORT | 0.0 | |
| 174 | >6K | 3 GLU LYS ASP | GLycerin | 185 | 3.0 | INS2 MT1 HEP3 | 0.3 | |
| 175 | >6K | 4 GLUPA ASP TYR PHE | | 172 | 3.5 | | 1.0 | |
| 176 | >6K | 3 GLU2 LYS2 LYS | — | 180 | 3.0 | INS0 MT0 HEP0 | 0.3 | |
| 177 | >6K | 3 GLU ARG ASP | — | 180 | 3.2 | INS0 MT2 HEP0 | 0.3 | |
| 178 | >6K | 3 GLU LYS ASP | — | 190 | 3.2 | INS0 MT0 HEP1 | 0.3 | |
| 179 | >6K | 4 GLU ASP TYR PHE | PA | 175 | 4.0 | | 1.0 | |
| 180 | >6K | 4 GLU ASP TYR PHE | PA | 175 | 7.0 | See Notes. | 1.0 | |
| 181 | >6K | 3 GLU LYS ASP | — | 185 | 3.0 | INS0 MT0 | 0.3 | |
| 182 | >6K | 4 GLU ASP TYR PHE | PA | 175 | 3.7 | MT1 HEP1 | 0.3 | |
| 183 | | 4 PGLU ASP TYR PHE | PA | 175 | 4.0 | ABORT-RETRY | 0.3 | |
| 184 | -cp | 4 GLU ASP TYR PHE | PA | 175 | 3.5 | MT2 HEP4 | 0.3 | |
| 185 | -cp | 4 GLU ASP TYR PHE | PA | 176 | 4.2 | INS MT4 HEP4 | 1.0 | |
| 187 | | 3 ASP TYR PHE | PA | 170 | .0 | ABORT | 0.3 | |
| 188 | -cp | 3 ASP TYR PHE | PA | 150 | 21.2 | INS0 MT0 HEP0 | 0.3 | |
| 189 | -cp | 4 GLU ASP TYR PHE | PA | 176 | 4.0 | MT4 HEP5 | 1.0 | |
| 190 | -cp | 4 GLU ASP TYR PHE | PA | 175 | 4.0 | MT5 HEP4 | 1.0 | |
| 191 | -cp | 3 ASP2 TYR PHE | PA | 150 | 24.0 | MT0 HEP0 | 0.3 | |
| 015 | | 2 GLU2 ASP2 EQU | — | 170 | 2.5 | | 0.0 | |
| 100 | | 3 GLU ASP VAL2 | — | 170 | 3.0 | | 0.0 | |
| 101 | | 3 GLU ASP VAL2 | — | 170 | 3.0 | | 0.0 | |
| 102 | | 3 GLU ASP VAL2 | — | 170 | 3.0 | | 0.0 | |
| 103 | | 4 GLU ASP GLY VAL | — | 170 | 3.5 | INS4 | 0.0 | |
| 104 | | 4 GLU ASP VAL LEU | — | 170 | 3.5 | INS4 MT2 HEP5 | 0.0 | |

-continued

PROTEINOID BATCHES

| Bt. No. | /AACOMPOSITION | ADDITIVE | TEMP C. | TIME (hr) | SPHERE RATING | BATCH SIZE molar | Operator | Date |
|---|---|---|---|---|---|---|---|---|
| 105 | 3 GLU ASP GLY2 | — | 180 | 4.0 | INS4 MT2 | 0.0 | | |
| 106 | 4 GLU ASP VAL LEU | — | 170 | 5.0 | | 0.0 | | |
| 107 | 4 GLU2 ASP2 GLY VAL2 | — | 170 | 3.0 | INS5 | 0.0 | | |
| 108 | 4 GLU2 ASP2 GLY VAL2 | — | 170 | 4.0 | INS4 NO AMORPHO | 0.0 | | |
| 109 | 4 GLU2 ASP2 GLY VAL2 | — | 170 | 4.0 | INS4 MT1 | 0.0 | | |
| 110 | 4 GLU2 ASP2 GLY2 VAL | — | 170 | 3.5 | | 0.0 | | |
| 111 | 5 GLU ASP GLY VAL CYS | — | 170 | 3.0 | | 0.0 | | |
| 112 | 4 GLU ASP GLY PHE | — | 170 | 4.0 | INS4 MT3 HEP4 | 0.0 | | |
| 113 | 4 GLU ASP VAL2 GLY | — | 170 | 3.9 | INS2 MT0 | 0.0 | | |
| 114 | 3 GLU ASP VAL | — | 170 | 3.0 | INS4 MT0 | 0.0 | | |
| 115 | 3 GLU VAL TYR | — | 170 | 4.0 | | 0.0 | | |
| 116 | 4 GLU ASP VAL LYS | — | 170 | 4.0 | | 0.0 | | |
| 117 | 3 GLU VAL TYR | — | 170 | 3.0 | INS5 | 0.0 | | |
| 118 | 2 GLU TYR | — | 170 | 3.5 | INS5 MT0 HEP0 | 0.0 | | |
| 119 | 2 GLU2 ASP2 EQU | — | 170 | 3.5 | INS5 MT1 | 0.0 | | |
| 120 | 3 GLU ASP TYR | — | 170 | 4.5 | INS0 MT0 HEP0 | 0.0 | | |
| 121 | 4 GLU ASP TYR PHE | — | 170 | 4.0 | INS5 MT3 HEP4 | 0.0 | | |
| 122 | 4 GLU ASP VAL TYR | — | 170 | 3.0 | INS3 MT0 HEP0 | 0.0 | | |
| 123 | 1 GLU | — | 170 | 4.5 | CAN'T DRY | 0.0 | | |
| 124 | 3 GLU TYR VAL | — | 170 | 3.5 | INS4 MT3 HEP3 | 0.0 | | |
| 125 | 3 PGLU VAL TYR | — | 170 | 3.5 | INS3 MT2 | 0.0 | | |
| 126 | 4 GLU ASP VAL2 GLY | — | 170 | 4.0 | INS1 | 0.0 | | |
| 127 | 4 GLU2 ASP2 VAL2 PHE | — | 170 | 4.0 | INS3 MT2 HEP4 | 0.0 | | |
| 128 | 2 GLU2 ASP2 EQU | — | 170 | 3.5 | MT0 | 0.0 | | |
| 129 | 2 GLU2 ASP2 EQU | — | VARY | 4.0 | INS3 MT0 | 0.0 | | |
| 130 | 2 GLU2 ASP2 EQU | — | 220 | 3.0 | INS5 MT0 | 0.0 | | |
| 131 | 2 GLU2 LYSFB | — | 185 | 3.0 | INS1 MT0 | 0.0 | | |
| 132 | 3 GLU ASP LYSFB | — | 185 | 3.0 | INS3 MT2 HEP2 | 0.0 | | |
| 133 | 3 GLU ASP LYSFB | PA | 180 | 6.2 | INS5 MT1 HEP2 | 0.0 | | |
| 134 | 4 GLU ASP LYS VAL | PA | 185 | 3.0 | | 0.0 | | |
| 135 | 3 GLU ASP LYSFB | GLYC | 185 | 6.5 | INS1 MT1 | 0.0 | | |
| 136 | 2 GLU2 ASP2 EQU | — | 155 | 3.0 | MT0 | 0.0 | | |
| 137 | 5 GLU2ASP2LEU THY VAL | — | 185 | 4.0 | INS0 MT0 | 0.0 | | |
| 138 | 4 GLU ASP VAL TYR | — | 185 | 4.5 | INS1 MT3 | 0.0 | | |
| 139 | 4 GLU ASP VAL TYR | PPA | 160* | 72.0 | INS2 MT3 | 0.0 | | |
| 140 | 3 GLU ASP LYSFB | PPA | 120 | 72.0 | INS5 MT2 HEP4 | 0.0 | | |
| 141 | 3 GLU LYSFBSYNPEPaggp | — | 185 | 6.0 | | 0.0 | | |
| 142 | 3 GLU ASP LYSFB | PPA | 120* | 72.0 | INS1 MT1 | 0.0 | | |
| 143 | 3 GLU VAL TYR | — | 170 | 3.0 | INS2 MT2 | 0.0 | | |
| 144 | 4 GLU2 ASP2 GLY VAL2 | — | 170 | 3.0 | INS1 MT1 | 0.0 | | |
| 354 | 5 -(GLU ASP TYR PHE)2 ORN | SULFOLANE | | .0 | | .0 | | |

Sphere rating: 0 =worst 5 =best
INT = insulin
MT = empty microsphere
HEP = heparin
Sul-M = sulfolane, medical grade
Sulfa = Sulf = Sul = Sulfolane
PA = phosphoric acid
Equ = equilents
GLYC = glycerol
TRIGL = triglyme
PPA = polyphosphoric acid
M.Oil = mineral o. = mineral oil
Glossary:
a = amorphous
o = oil
* = varying temperature
+ = cook time change

APPENDIX B

IEF TABLES
Proteinoid sorting, pKa and composition
Chemical basis for microsphere ODS

| Run No. | Material ID No. | Composition ->(* no amp) | Sphere frac number | Sphere pH range | Sphere IEF rating | Sphere Matrix rating | | | Max UV Frac. No. | Max UV pH |
|---|---|---|---|---|---|---|---|---|---|---|
| 202B | | Glu2.4 Asp2Val2Gly * | no spher | 13 | — | INS4 | HT0 | HEP3 | 14-19 | 4.4-3.0 |
| 210>1k | | Glu Asp Val Lys | 14-20 | 2.3-4.4 | 2-3 | INS4 | HT4 | HEP3 | 11-16 | 7.6-2.1 |
| 213>1k | | Glu LysFb HisFB | 16-19 | 1.7-2.1 | 2 | INS0 | HT0 | HEP0 | 1-7 | 12.2-9.3 |
| 218<3k | | Glu Asp Tyr Phe | 18-20 | 3.2-2.7 | 2 | INS0 | HT0 | HEP0 | 15-18 | 2.9-2.5 |
| 129 | | Glu Asp Equ | 10-18 | 2.5-4.4 | 3 | INS3 | HT0 | HEP0 | 1-4 | 11.8-9.2 |
| 214>1k | | Glu LysFB Arg | no spher | — | — | INS0 | HT0 | HEP0 | 5-6 | 9-8.6 |
| 176 | | Glu LysFB2 LysEB | no spher | — | — | INS0 | HT0 | HEP2 | 2-6 | 8.5-11.5 |
| 222-cp | | Arg2 LysFB2 Leu | 21-4? | 9.9-11.7 | 2? | INS4 | HT0 | HEP3 | 8-12 | 5-3.3 |
| 202B | | Glu2.4 Asp2 Val2 Gly | 8-12 | 3.3-5 | 2.1-2 | INS0 | HT0 | HEP2 | 1 | 10.3 |
| 223-cp | | Arg2 LysFB2 Leu pGlu | 1 | 10.3 | 2-3 | INS0 | HT0 | HEP2 | 3 | 10.7 |
| 223-cp | | Arg2 LysFB2 Leu pGlu | 1-5 | 9.0-12 | 2-3 | HT5 | | | 16-20 | 5-2.3 |
| 170a | | Glu Asp LysFB | 16-20 | 2.3-5.0 | 2 | INS4 | HT4 | HEP4 | 14-17 | 3.9-2.8 |
| 216>3K | | Glu Asp Tyr Phe(sul) | 14-20 | 2.4-3.9 | 1-2 | INS3 | HT2 | | 9-13 | 3.2-2.7 |
| 125 | | pGlu Val Tyr | 13-20 | 2.7-3.6 | | INS0 | HT0 | HEP0 | 14-20 | 5-3.4 |
| 228-B20 | | sul Val2 Gly2 pGlu | no spher | — | 2-3 | INS0 | HT0 | HEP0 | 16-18 | 3.8-3.3 |
| 228-AB | | sul Val2 Gly2 pGlu | no spher | — | 1-2 | INS0 | HT2 | HEP0 | 14-19 | 5.2-3.9 |
| 177 | | Glu Asp Arg | 14-19 | 5.2-3.9 | | INS0 | HT0 | HEP0 | 12-19 | 6-4.2 |
| 118 | | Glu Tyr | 12-14 | 5.2-6.0 | | INS5 | HT0 | HEP0 | 8-9 | 9.1-10.2 |
| 153 | | Glu LysEB Phe | no spher | — | 2-3 | INS1 | HT0 | | 14-17 | 4.3-3.6 |
| 131 | | Glu2 Lys | no spher | — | | INS3 | HT0 | HEP0 | 16-17 | 4.1-3.7 |
| 162 | | Glu2 Tyr Phe | 16-17 | 4.1-3.7 | 2-3 | INS0 | | | 20 | 4.5 |
| 156 | | Glu4 Lys2 Phe | no spher | — | | INS4 | HT4 | HEP4 | 13-14 | 3.7-3.5 |
| 124 | | Glu Val Tyr | no spher | — | 1-2 | INS4 | HT4 | HEP3 | 12-19 | 3.6-3.2 |
| 210>1K | | Glu Asp Lys Val * | 12-20 | 3.6-3.1 | 2 | INS0 | | | 14 | 3.6 |
| 156 | | Glu4 Lys2 Phe | 14-17 | 3.6-3.1 | | INS2 | HT0 | HEP3 | 18 | 9.1 |
| 231 | | Glu Lys Phe sul | no spher | — | 1-2 | INS0 | HT0 | HEP2 | 6 | 10.9 |
| 232 | | Glu Leu Lys | no spher | — | 2 | INS0 | HT0 | HEP2 | 9 | 10 |
| 233 | | Glu Leu Arg | no spher | — | | | | | | |
| blank | | 2% ampholytes | — | — | — | | | | — | — |
| 236>3k | | Glu Asp sul Tyr Phe | 14-20 | 4.1-2.6 | 2 | INS4 | HT4 | HEP4 | 18-20 | 3-2.6 |
| 230>1k | | Glu Tyr | 13-20 | 3.9-3 | 3 | INS4 | HT4 | HEP0 | 15-20 | 3.3-3 |
| 170a | | Glu Asp LysFB | 15-20 | 3.9-2.2 | 2 | HT5 | | | 18-19 | 3.3-2.6 |
| 236-cp | | Glu Tyr Lys-HCl | 19-20 | 3.0 | 0-1 | INS2 | HT0 | HEP0 | 19-20 | 3 |
| 216<3k | | Glu Asp sul TyrPhe * | 14-20 | 3.3-2.2 | 2 | INS4 | HT4 | HEP4 | 20 | 2.2 |
| 216<3k | | Glu Asp sul Tyr Phe | 16-20 | 3.9-2.3 | 1-2 | INS4 | HT4 | HEP4 | 20 | 2-3 |
| 237-cp | | Glu2 Leu2 Lys2 Asp | no spher | — | 2 | INS0 | HT0 | HEP0 | 9-12 | 4.6-4 |
| 243-cs | | pGluArg2Lys2LeuAsp | no spher | — | — | INS4 | HT0 | HEP2 | 15-17 | 8.5-7 |
| 246-cs | | Glu2 LysH2 Phe Asp | 17-20 | 4.1-2.2 | 2-3 | INS4 | HT0 | HEP4 | 17-20 | 4.1-2.2 |
| 250-cs | | pGluArg2LysH2LeuAsp2 | no spher | — | — | INS4 | HT4 | HEP0 | 11-14 | 8-6.8 |
| 249<3K | | Glu2 Leu2 LysH2 pGlu | no spher | — | — | INS0 | HT0 | HEP0 | — | — |
| 254-cp | | GluAspsulTyrPheOrn.5 | 18 | 5.4-2.5 | 2 | INS3 | HT4 | HEP4 | 14-20 | 3.7-2.1 |
| 253-cp | | Glu Asp sul Tyr Phe | 18-20 | 3-4 | 2 | INS0 | HT0 | HEP0 | 1-4, 19-20 | 11.5, 3-3.5 |
| 235<3k | | GluAspsulTyr10Phe10 | 18-20P | 2.6-3.2 | 1-2 | INS0 | HT0 | HEP0 | 1-3 | 11 |
| 256-cp | | Glu2 LysH2 Phe2 pGlu | 13-20 | 3.7-4.0 | 1-2 | INS0 | HT0 | HEP0 | 2-5, 14-20 | 2.7-4, 7-10 |

APPENDIX B-continued

IEF TABLES
Proteinoid sorting, pKa and composition
Chemical basis for microsphere ODS

| Run No. | Material ID No. | Composition —>(* no amp) | Sphere frac number | Sphere pH range | Sphere IEF rating | Sphere Matrix rating | Max UV Frac. No. | Max UV pH |
|---|---|---|---|---|---|---|---|---|
| 47 | 238<3K | GluAspsulTyr5Phe5 | no spher | — | — | INS1 HT3 HEP4 | 2 | 11.4 |
| 48 | 255-CP | Glu AspTyrsulPheOrn | 13–20 | 5.3–3.1 | 2 | INS1 HT3 HEP4 | 1–6, 19–20 | 11–9.3.6–3 |
| 49 | 251<3K | Glu2Asp2sulTyr5Phe5 | 16–20 | 5.5–3.3 | 2 | INS4 HT4 HEP4 | 17–20 | 5.8–3.8. |
| 50 | 257-CP | Glu Asp ArgH OrnH | no spher | — | — | INS0 HT0 HEP0 | 19–20 | 5–3 |
| 51 | 257-CP | Glu Asp ArgH OrnH* | no spher | — | — | INS0 HT0 HEP0 | 15–17 | 8.9–8.5 |
| 52 | 258<3K | Glu Asp ArgH | no spher | — | 2 | INS0 HT0 HEP4 | 1, 17–20 | 9.8, 4–2.5 |
| 53 | 262-CP | Glu Orn Asp LysFB | 11–18 | 6.8–3.5 | — | INS0 HT1 HEP4 | 15 | 4.8 |
| 54 | 262-FILT | Glu Orn Asp LysFB | 4–11 | 7.7–5.4 | 1–2 | ins0 ntl hep4 | 1–2, 12–20 | 9.4.6–1.8 |
| 55 | 267-cp | Glu LysFB Asp LysFB | no spher | — | — | INSa HTc HEPc | 14–20 | 6.3–3.8 |
| 56 | 268-cp c | Glu Asp sul Tyr The | 15–20 | 4.5–2.34 | 2–3 | INS4oHToHEP4a | 1–10, 18–20 | 12–2.5 |
| 57 | 269-cp | Glu OrnH Asp LysFB | 17–20 | 2.91–1.4 | 1 | INSc HTc HEPc | 4, 7, 9 | 9–7.5 |
| 58 | 273-cp | Glu Leu LysH Phe | 17–20 | 3–1.2 | 1–2 | INSc HTc HEPc | 19 | 2 |
| 59 | 272/273 | Glu Leu LysH | — | — | — | INS2a HT2 HEP2a | 3–9, 13–15 | 9.8.5, 8–8. |
| 60 | 276 | Glu Leu Arg Phe | 12–18 | 3.57–1.4 | 1–2, 2 | INS2 HTc HEP3 | 1–7, 17–20 | 9–6, 1.5–1. |
| 61 | 274 | Glu Leu Arg Tyr | no spher | — | — | INSc HTc Hepc | 16–20 | 4.14–1.4 |
| 62 | 272 | Glu Leu LysH Tyr | no spher | — | — | INSc HTc HEPc | 1–2 | 9.4–9.3 |
| 63 | 274A | Glu Leu Arg | no spher | — | — | — | all frac. | — |
| 64 | 278 | Glu Lys Phe sul | 16–20 | 4.8–3.5 | 1–2 | INSc HTc HEP4 | all frac. | 3.3–2.1 |
| 65 | 284E | GluAspTyrPhesulOrn | 14–20 | 3.8–2.1 | 1–2 | INS4oHT4oHEP3 | 15–20 | 2.4–2.3, 8 |
| 66 | 287-cp | Glu Phe | 10–20 | 3.55–2.3 | 2 | INS3 HT3 HEP3 | 18–20, 1–7 | 12.3–7.76 |
| 67 | 284-H | Glu2Asp2Tyr2Phe2Orn | 14–20 | 3.95–1.6 | 2 w/oil | INS4a HT4aHEP2a | 3–8 | 2.7–1.02 |
| 68 | 288-cp | Glu Orn Phe | no spher | — | — | INSc HTc HEPc | 17–20 | |
| 69 | 293-cp | Glu Asp sul Tyr Phe | 1–8 | 1.9–3.9 | 1–2 | INS1 HT2 HEP1a | 18–20 | 12.1–12.6 |
| 70 | 290-cp | Glu Arg Phe | 1–7 | 1.05–3.8 | 1–2 | INS1 HT1 HEP1 | 16–20 | 3.19–1.5 |
| 71 | 292-cp | Glu Asp Arg | no spher | — | — | INS HT HEP | all frac. | |
| 72 | 300-cp | Glu Orn Asp Lys Phe | 15–19 | 4.05–1.5 | 1–2 | INS3 HT3 HEP3? | 1–2 | 2.38–2 |
| 73 | 297-cp | GLU ASP SUL TYR PHE | 1–7 | 2.38–4.15 | 2–3 | INS3 HT4 HEP | 1–20 | |
| 74 | 301<3K | GLU ASP SUL TYR PHE | — | — | — | INS4 MT2 HEP3 | 1–3, 18–20 | 2.88/1 |
| 75 | 303 | GLU ASP SUL TYR PHE | 1–6 | 2.83–3.76 | 2–3 | INS4 HT2 HEP3a | 3–7 | 1.58–3 |
| 76 | 299 | GLU2 LYS2 PRE2 ASP | 1–7 | 1.13–3.82 | 1 | INS4a HT2 HEP2a | 11–20 | 5.54–1 |
| 77 | 305 | PGLU ASP.5 TYR PHE | 1–12 | 2.12–4.20 | 2–3 | INS3 HT2 HEP3 | 1–13 | 2.43–7.0 |
| 78 | 307 | GLN ASP TYR PHE | 1–9 | 2.43–4.48 | 2–3 | INS4o HT4 HEP4a | 4–7 | 3.3–7.0 |
| 79 | 305 | PGLU ASP.5 TYR PHE | 1–6 | 2.05–5.56 | — | INS3 HT2 HEP3 | 1 | 10.58 |
| 80 | 124/156 | GLU TYR VAL/GLU2 LYS2 PHE | — | — | — | INS0 HT0 HEP2 | | |
| 81 | 223-CP | LYS APG LEU PGLU | 1–10 | 2.28–5.3 | 2–3o | INS4aHT4hEP4a | 2–8, 19–20 | 2.3–4,12 |
| 82 | 319-CP | SUL-U TYR PHE ASP PGLU | 1–11 | 1.93–5.30 | 2 | INS2aHT4aHEP4a | 18 | 8.95 |
| 83 | 314-CP | SUL TYR PRE ASP PGLU | 3–7 | 2.12–4.4 | 2a | INS4aHT4HEP4 | 16–20 | 9.3–10.25 |
| 84 | 320-CP | SUL TYR PRE PGLU ASP | 1–6 | 1.85–5 | 0a | INS0HT0HEP0 | 18–20 | 12–12.5 |
| 85 | 188>6K | ASP2 TYR PHE | — | — | PARTICLES | INSCHTCHEPC | 14–18 | 2.38 |
| 86 | 286-CP | GLU ASP | 14–18 | 2.38–2.02 | 1–2 | INSCHTCHEPC | 17–19 | 3.1–1.65 |
| | 288/188 | ASP2 TYR PRE/GLU ORH PHE | 14–17 | 4.9–3.1 | — | HTO | 16–19 | 2.85–2.55 |
| | 66 | GLU2 GLY | — | — | 1, 0–1 | INS5aHT3aHEP3a | 14, 2 | 9.20, 3.32 |
| | 0112-2A | GLU ASP TYR PRE | 1–10 | 3.17–13.48 | | | | |

APPENDIX C

Sphere Testing of Externally Prepared Proteinoids

| SOI No. | Composition | pH | | 0.85 CA | 5% AA | 0.85 CA + GH | 5% AA + GH | IHS/CA GH/GL/CD | IHS/AA GH/GL/CD | HEP/CA + GH |
|---|---|---|---|---|---|---|---|---|---|---|
| 91EHIP001P20B1SA08 | GLU ASP TYR PHE | — | Rating | 1–2 | 1–2 | 3 | 2–3 | 2–3 | 0 | 2–3 |
| | | | Desc. | a | a | — | a | a | a | a |
| | | | pH | — | — | — | — | — | — | — |
| 91EHIP001P21B1SA07 | GLU ASP TYR PHE | — | Rating | 2–3 | 2–3 | 3–4 | 3–4 | 2–3 | 4 | 4–5 |
| | | | Desc | a, ag | a, ag | a | a | a, p | a, ag | a, p |
| | | | pH | — | — | — | — | — | — | — |
| 91EHIP001F21B1SA07 | GLU ASP TYR PHE | — | Rating | 3 | 3 | 4–5 | 3 | 3–4 | 3–4 | 4–5 |
| | | | Desc. | ag, a | a | a | ag ,p | ag, p | ag, p | a, p |
| | | | pH | — | — | — | — | — | — | — |
| 91EHIP001F22B1SA7 | GLU ASP TYR PHE | — | Rating | 2–3 | 2–3 | 3 | 4–5 | 0 | 3–4 | 4–5 |
| | | | Desc. | — | a | — | a, o | a | o | a |
| | | | pH | — | — | — | — | — | — | — |
| 91EHIP011F23B1SA8 | GLU ASP TYR PHE ORN | — | Rating | 2–3 | 3 | 4 | 4 | 0–1 | 4 | 3–4 |
| | | | Desc. | a, p | a | — | — | a | a, o | a, o |
| | | | pH | — | — | — | — | — | — | — |
| 91EHIP011P24SA7 | GLU ASP TYR PHE ORN | — | Rating | 2 | 2 | 2–3 | 3 | 4 | 0–1 | 5 |
| | | | Desc. | a | a | o | — | a | a, o | p |
| | | | pH | — | — | — | — | — | — | — |
| 91EHIP001P25B1SA2A | GLU ASP TYR PHE | — | Rating | 0–1 | 0 | 3–4 | 0 | 3–4 | 4–5 | 4–5 |
| | | | Desc. | — | a, p | a | a | a | a | a |
| | | | pH | — | — | — | — | — | — | — |
| 91EHIP001P25B1SA5 | GLU ASP TYR PHE | — | Rating | 0–1 | 1 | 2–3 | 2–3 | 0–1 | 3–4 | 2–3 |
| | | | Desc* | a | a | a | — | a | a, o | a |
| | | | pH | — | — | — | — | — | — | — |
| 91EMIP001P26B1SA2A | GLU ASP TYR PHE | — | Rating | 2–3 | 2–3 | 3 | 3–4 | 2 | 2–3 | 3–4 |
| | | | Desc. | — | a | — | — | a | — | o |
| | | | pH | — | — | — | — | — | — | — |
| | | | Rating | | | | | | | |
| | | | Desc. | | | | | | | |
| | | | pH | | | | | | | |
| 91CTAP001P014B02 | GLU ASP TYR PHE | — | Rating | 2–3 | 3 | 5 | 4–5 | 4–5 | 2–3 | 3 |
| | | | Desc. | a | a | a | — | a | a | a |
| | | | pH | — | — | — | — | — | — | — |
| 91CTAP001P014B02 | GLU ASP TYR PHE | — | Rating | 2 | 4–5 | 5 | 5 | 5 | 5 | 5 |
| | | | Desc. | — | a | — | — | — | — | — |
| | | | pH | — | — | — | — | — | — | — |
| 91CTAP001P014B02 | GLU ASP TYR PHE | — | Rating | 2–3 | 3 | 5 | 4–5 | 4–5 | 2–3 | 3 |
| | | | Desc. | a | a | a | — | a | a | a |
| | | | pH | — | — | — | — | — | — | — |
| 91CTAP001P014B03 | GLU ASP TYR PHE | — | Rating | 2 | 2 | 3–4 | 3–4 | 5 | 3 | 3–4 |
| | | | Desc. | a | a | a | a | a | a | a |
| | | | pH | — | — | — | — | — | — | — |
| 91CTAP001P014B03 | GLU ASP TYR PHE | — | Rating | 0–1 | 0–1 | 5 | 5 | 5 | 2–3 | 4 |
| | | | Desc. | a, aq | a, aq | a, ag | a, ag | a, ag | a | — |
| | | | pH | — | — | — | — | — | — | — |
| 91CTAP001P014B03 | GLU ASP TYR PHE | — | Rating | 2–3 | 2–3 | 5 | 5 | 5 | 3 | 5 |
| | | | Desc. | ag | ag | a, ag | — | a, aq ,o | ag, a | — |
| | | | pH | — | — | — | — | — | — | — |
| 91CTAP001P014B03 | GLU ASP TYR PHE | — | Rating | 2 | 2 | 3–4 | 3–4 | 5 | 3 | 3–4 |
| | | | Desc. | a | a | a | a | a | a | a |
| | | | pH | — | — | — | — | — | — | — |
| 91CTAP001P014B04 | GLU ASP TYR PHE | — | Rating | 0–1 | 0–1 | 4 | 5 | 2–3 | 0 | 5 |
| | | | Desc. | a | a | a | a | a | a | a |
| | | | pH | — | — | — | — | — | — | — |
| 91CTAP001P014B05 | GLU ASP TYR PHE | — | Rating | 3 | 3–4 | 5 | 4–5 | 4 | 4 | 4 |
| | | | Desc. | — | a | a | — | a | a | a |
| | | | pH | — | — | — | — | — | — | — |
| 91CTAP001F014B04 | GLU ASP TYR PHE | — | Rating | 3 | 3–4 | 5 | 4–5 | 4 | 4 | 4 |
| | | | Desc. | — | a | a | — | a | a | a |
| | | | pH | — | — | — | — | — | — | — |
| 91EHIP011P15B1 | GLU2ASP2TYR2PHE2ORN | — | Rating | 2–3 | 3 | 4 | 3–4 | 0 | 3–4 | 4 |
| | | | Desc. | a, ag | ag | — | a, o | a | — | — |
| | | | pH | — | — | — | — | — | — | — |
| 91EHIP001P20B1SA07 | GLU ASP TYR PHE | — | Rating | 2 | 2–3 | 3 | 2–3 | 4 | 3 | 4 |
| | | | Desc. | ag | ag | — | — | a, o | a, o | — |
| | | | pH | — | — | — | — | — | — | — |
| | | | Rating | | | | | | | |
| | | | Desc. | | | | | | | |
| | | | pH | | | | | | | |
| 91EH1P00IF25B1SA3a | | 6.52 | Rating | 2–3 | 2–3 | 3–4 | 4 | 3–4 | 4 | 5 |
| | | | Desc. | ag, a | ag | — | — | a, p | o | — |
| | | | pH | — | — | — | — | — | — | — |
| 91CTAP001P012B01 | GLU ASP TYR PHE | 7.5 | Rating | 2–3 | 2 | 5 | 5 | 4 | 5 | 5 |
| | | | Desc. | a | a | — | — | a | — | a |

APPENDIX C-continued

Sphere Testing of Externally Prepared Proteinoids

| SOI No. | Compostion | pH | | 0.85 CA | 5% AA | 0.85 CA + GH | 5% AA + GH | IHS/CA GH/GL/CD | IHS/AA GH/GL/CD | HEP/CA + GH |
|---|---|---|---|---|---|---|---|---|---|---|
| P005-B01 | GLU2 LYSH2 PHE2 ASP | 9.0 | pH | — | — | — | — | — | — | — |
| | | | Rating | — | — | 3–4 | — | 4 | 3 | 3 |
| | | | Desc. | — | — | a, o | — | a, o | a, o | a, o |
| 91CTAPR001P010B01 | GLU2 LYSH2 PHE2 ASP | — | pH | — | — | — | — | — | — | — |
| | | | Rating | 2–3 | 2 | 4 | 4 | 4 | 4 | 4 |
| | | | Desc. | a | a | — | — | a | a | a |
| P003-B01 | GLU2 LYSH2 PHE2 ASP | — | pH | — | — | — | — | — | — | — |
| | | | Rating | — | — | 4 | 3–4 | 3 | 4–5 | 3 |
| | | | Desc. | — | — | a | o | a | a | a, o |
| P004-B01 | GLU2 LYSH2 PHE2 ASP | — | pH | — | — | — | — | — | — | — |
| | | | Rating | — | — | 3–4 | 2–3 | 2–3 | 4 | 2–3 |
| | | | Desc. | — | — | a, o | a | a | a | a |
| 91CTAP001P011B01 | GLU ASP TYR PHE ORN | — | pH | — | — | — | — | — | — | — |
| | | | Rating | — | — | — | — | — | — | — |
| | | | Desc. | — | — | — | — | — | — | — |
| 91CTAP001P013B01 | GLU ASP TYR PHE | 7.9 | pH | — | — | — | — | — | — | — |
| | | | Rating | 2–3 | 2–3 | 4–5 | 4–5 | 4–5 | 4 | 5 |
| | | | Desc. | — | a | — | a, o | a, o | a, o | a |
| 91CTAP001P014B01 | GLU ASP TYR PHE | 8.0 | pH | — | — | — | — | — | — | — |
| | | | Rating | 0 | 0–1 | 4–5 | 4–5 | 4–5 | 3–4 | 4 |
| | | | Desc. | a | a | a | — | a | a | a |
| 91CTAP001P014B01 | GLU ASP TYR PHE | — | pH | — | — | — | — | — | — | — |
| | | | Rating | 0–1 | 0–1 | 5 | 4 | 4 | 3 | 3–4 |
| | | | Desc. | a | a | a, o | a, o | a, o | a, o | a, o |
| 91CTAP001P014B01 | GLU ASP TYR PHE | — | pH | — | — | — | — | — | — | — |
| | | | Rating | 2 | 2 | 5 | 5 | 5 | 3 | 5 |
| | | | Desc | ag | ag, a | ag | — | ag, a | ag, a | — |
| | | | pH | — | — | — | — | — | — | — |

CA = citric acid
INS = insulin
GM = gum acacia
HEP = heparin
GL = gelatin
CD = cyclodextrin
a = amorphous
o = oil
P = particulate
aq = aggregate
eating: 0 = worst 5 = best

What is claimed is:

1. A proteinoid carrier comprising a proteinoid comprising
   i) a monomer selected from the group consisting of tyrosine, phenylalanine, and a mixture thereof;
   ii) a monomer selected from the group consisting of glutamic acid, pyroglutamic acid, glutamine, aspartic acid, and a mixture thereof; and
   iii) optionally a monomer selected from the group consisting of lysine, arginine, ornithine, and a mixture thereof,
       said proteinoid being a microsphere or microcapsule forming proteinoid and being soluble within a selected pH range and said proteinoid having a molecular weight ranging from 250 to 600 daltons.

2. The proteinoid carrier of claim 1, wherein said proteinoid carrier comprises a proteinoid microsphere.

3. The proteinoid carrier of claim 1, wherein said proteinoid carrier comprises a proteinoid microcapsule.

4. The proteinoid carrier of claim 1, wherein said proteinoid comprises a monomer selected from the group consisting of lysine, arginine, ornithine, and a mixture thereof and said proteinoid is acid-soluble.

5. The proteinoid carrier of claim 1, wherein said proteinoid is a base-soluble proteinoid.

6. The proteinoid carrier of claim 1, wherein said proteinoid carrier having a diameter equal to or less than 10 microns.

7. The proteinoid carrier of claim 1, further encapsulating a cargo.

8. The proteinoid carrier of claim 7, wherein said cargo comprises a fragrance, cosmetic agent, dye, and water soluble vitamin.

9. The proteinoid carrier of claim 7, wherein said cargo is a biologically active agent.

10. The proteinoid carrier of claim 9, wherein said biologically active agent comprises an antigen, monoclonal antibody, calcitonin, erythropoietin, alpha interferon, heparin, insulin, growth hormone, atrial naturetic factor, factor IX, an antimicrobial agent, aspirin, or interleukin-II.

11. A composition comprising a biologically active agent encapsulated within a proteinoid microcapsule, said microcapsule comprising a proteinoid comprising
    i) a monomer selected from the group consisting of tyrosine, phenylalanine, and a mixture thereof;
    ii) a monomer selected from the group consisting of glutamic acid, pyroglutamic acid, glutamine, aspartic acid, and a mixture thereof; and
    iii) optionally a monomer selected from the group consisting of lysine, arginine, ornithine, and a mixture thereof,
        said proteinoid being a microcapsule forming proteinoid and being soluble within a selected pH range and said proteinoid having a molecular weight ranging from 250 to 600 daltons.

12. The composition of claim 11, wherein said proteinoid comprises a monomer selected from the group consisting of lysine, arginine, ornithine, and a mixture thereof and said proteinoid is acid-soluble.

13. The composition of claim 11, wherein said proteinoid is a base-soluble proteinoid.

14. The composition of claim 11, wherein said biologically active agent comprises an antigen, monoclonal antibody, calcitonin, erythropoietin, alpha interferon, heparin, insulin, growth hormone, atrial naturetic factor, factor IX, an antimicrobial agent, aspirin, or interleukin-II.

15. A pharmaceutical preparation comprising an oral dosage form of calcitonin encapsulated within a proteinoid microcapsule, said microcapsule comprising a proteinoid comprising
- i) a monomer selected from the group consisting of tyrosine, phenylalanine, and a mixture thereof;
- ii) a monomer selected from the group consisting of glutamic acid, pyroglutamic acid, glutamine, aspartic acid, and a mixture thereof; and
- iii) optionally a monomer selected from the group consisting of lysine, arginine, ornithine, and a mixture thereof,
  - said proteinoid being a microcapsule forming proteinoid and being soluble within a selected pH range and said proteinoid having a molecular weight ranging from 250 to 600 daltons.

16. A pharmaceutical preparation comprising an oral dosage form of a monoclonal antibody encapsulated within a proteinoid microcapsule, said microcapsule comprising a proteinoid comprising
- i) a monomer selected from the group consisting of tyrosine, phenylalanine, and a mixture thereof;
- ii) a monomer selected from the group consisting of glutamic acid, pyroglutamic acid, glutamine, aspartic acid, and a mixture thereof; and
- iii) optionally a monomer selected from the group consisting of lysine, arginine, ornithine, and a mixture thereof,
  - said proteinoid being a microcapsule forming proteinoid and being soluble within a selected pH range and said proteinoid having a molecular weight ranging from 250 to 600 daltons.

17. A pharmaceutical preparation comprising an oral dosage form of erythropoietin encapsulated within a proteinoid microcapsule, said microcapsule comprising a proteinoid comprising
- i) a monomer selected from the group consisting of tyrosine, phenylalanine, and a mixture thereof;
- ii) a monomer selected from the group consisting of glutamic acid, pyroglutamic acid, glutamine, aspartic acid, and a mixture thereof; and
- iii) optionally a monomer selected from the group consisting of lysine, arginine, ornithine, and a mixture thereof,
  - said proteinoid being a microcapsule forming proteinoid and being soluble within a selected pH range and said proteinoid having a molecular weight ranging from 250 to 600 daltons.

18. A pharmaceutical preparation comprising an oral dosage form of Factor IX encapsulated within a proteinoid microcapsule, said microcapsule comprising a proteinoid comprising
- i) a monomer selected from the group consisting of tyrosine, phenylalanine, and a mixture thereof;
- ii) a monomer selected from the group consisting of glutamic acid, pyroglutamic acid, glutamine, aspartic acid, and a mixture thereof; and
- iii) optionally a monomer selected from the group consisting of lysine, arginine, ornithine, and a mixture thereof,
  - said proteinoid being a microcapsule forming proteinoid and being soluble within a selected pH range and said proteinoid having a molecular weight ranging from 250 to 600 daltons.

19. A method for delivering calcitonin to a mammal which comprises orally administering the pharmaceutical preparation according to claim 15.

20. A method for delivering erythropoietin to a mammal which comprises orally administering the pharmaceutical preparation according to claim 17.

21. A method for delivering Factor IX to a mammal which comprises orally administering the pharmaceutical preparation according to claim 18.

* * * * *